(12) United States Patent
Maahs et al.

(10) Patent No.: US 7,736,378 B2
(45) Date of Patent: Jun. 15, 2010

(54) APPARATUS AND METHODS FOR POSITIONING AND SECURING ANCHORS

(75) Inventors: Tracy D. Maahs, Rancho Santa Margarita, CA (US); Richard C. Ewers, Fullerton, CA (US); Jesus Flores, Perris, CA (US); Alexander Khairkhahan, Palo Alto, CA (US); Ruey-Feng Peh, Mountain View, CA (US); Vahid Saadat, Atherton, CA (US); Cang C. Lam, Irvine, CA (US)

(73) Assignee: USGI Medical, Inc., San Clemente, CA (US)

( * ) Notice: Subject to any disclaimer, the term of this patent is extended or adjusted under 35 U.S.C. 154(b) by 837 days.

(21) Appl. No.: 10/841,245

(22) Filed: May 7, 2004

(65) Prior Publication Data

US 2005/0251206 A1 Nov. 10, 2005

(51) Int. Cl.
A61B 17/04 (2006.01)
(52) U.S. Cl. ..................................................... 606/232
(58) Field of Classification Search ................ 606/232, 606/233, 213, 220, 72, 74, 103; 227/66, 227/67; 24/115 R, 127, 128, 130, 131 R, 24/129 B, 129 C, 136 R; 411/29, 37
See application file for complete search history.

(56) References Cited

U.S. PATENT DOCUMENTS

| | | | |
|---|---|---|---|
| 2,201,610 A | 5/1940 | Dawson, Jr. | |
| 2,413,142 A | 12/1946 | Jones et al. | |
| 3,143,916 A * | 8/1964 | Rice | 411/37 |
| 3,150,379 A | 9/1964 | Brown | |
| 3,166,072 A | 1/1965 | Sullivan, Jr. | |
| 3,316,796 A * | 5/1967 | Young | 411/29 |
| 3,494,006 A | 2/1970 | Brumlik | |
| 3,646,615 A | 3/1972 | Ness | |

(Continued)

FOREIGN PATENT DOCUMENTS

EP 0 847 727 A1 6/1998

(Continued)

OTHER PUBLICATIONS

Angiolink, The Expanding Vascular Staple [brochure], 1 page total.

(Continued)

Primary Examiner—Julian W Woo
(74) Attorney, Agent, or Firm—Levine Bagade Han LLP; Charles C. Fowler

(57) ABSTRACT

Apparatus and methods for positioning and securing anchors are disclosed herein. The anchors are adapted to be delivered and implanted into or upon tissue, particularly tissue within the gastrointestinal system of a patient. The anchor is adapted to slide uni-directionally over suture such that a tissue plication may be cinched between anchors. A locking mechanism either within the anchor itself of positioned proximally of the anchor may allow for the uni-directional translation while enabling the anchor to be locked onto the suture if the anchor is pulled, pushed, or otherwise urged in the opposite direction along the suture. This uni-directional anchor locking mechanism facilitates the cinching of the tissue plication between the anchors and it may be utilized in one or several anchors in cinching a tissue fold.

33 Claims, 36 Drawing Sheets

U.S. PATENT DOCUMENTS

| | | |
|---|---|---|
| 3,664,345 A | 5/1972 | Dabbs et al. |
| 3,753,438 A | 8/1973 | Wood et al. |
| 3,867,944 A | 2/1975 | Samuels |
| 3,874,388 A | 4/1975 | King et al. |
| 3,910,281 A | 10/1975 | Kletschka et al. |
| 3,976,079 A | 8/1976 | Samuels et al. |
| 4,006,747 A | 2/1977 | Kronenthal et al. |
| 4,007,743 A | 2/1977 | Blake |
| 4,060,089 A | 11/1977 | Noiles |
| 4,069,825 A | 1/1978 | Akiyama |
| 4,235,238 A | 11/1980 | Ogiu et al. |
| 4,367,746 A | 1/1983 | Derechinsky |
| 4,414,720 A | 11/1983 | Crooms |
| 4,462,402 A | 7/1984 | Burgio |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kumak et al. |
| 4,592,356 A | 6/1986 | Gutierrez |
| 4,595,007 A | 6/1986 | Mericle |
| 4,610,250 A | 9/1986 | Green |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs et al. |
| 4,765,335 A | 8/1988 | Schmidt et al. |
| 4,828,439 A * | 5/1989 | Giannuzzi .................... 411/37 |
| 4,832,055 A | 5/1989 | Palestrant |
| 4,841,888 A | 6/1989 | Mills et al. |
| 4,873,976 A | 10/1989 | Schreiber |
| 4,881,302 A * | 11/1989 | Lee .......................... 24/136 R |
| 4,890,615 A | 1/1990 | Caspari et al. |
| 4,923,461 A | 5/1990 | Caspari et al. |
| 4,929,240 A | 5/1990 | Kirsch et al. |
| 4,957,498 A | 9/1990 | Caspari et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| RE34,021 E | 8/1992 | Mueller et al. |
| 5,176,691 A | 1/1993 | Pierce |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,258,015 A * | 11/1993 | Li et al. ..................... 606/232 |
| 5,261,916 A | 11/1993 | Engelson |
| 5,268,001 A | 12/1993 | Nicholson et al. |
| 5,269,809 A * | 12/1993 | Hayhurst et al. ............ 606/232 |
| 5,282,827 A | 2/1994 | Kensey et al. |
| 5,284,488 A | 2/1994 | Sideris |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,330,503 A | 7/1994 | Yoon |
| 5,334,217 A | 8/1994 | Das |
| 5,342,376 A | 8/1994 | Ruff |
| 5,350,399 A * | 9/1994 | Erlebacher et al. ........... 606/213 |
| 5,354,298 A | 10/1994 | Lee et al. |
| 5,366,459 A | 11/1994 | Yoon |
| 5,366,479 A | 11/1994 | McGarry et al. |
| 5,370,661 A * | 12/1994 | Branch ....................... 606/232 |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,383,905 A * | 1/1995 | Golds et al. .................. 606/232 |
| 5,403,329 A | 4/1995 | Hinchcliffe |
| 5,417,691 A | 5/1995 | Hayhurst et al. |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,727 A | 7/1995 | Sideris |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,549,618 A | 8/1996 | Fleenor et al. |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,119 A | 11/1996 | Atala |
| 5,573,540 A | 11/1996 | Yoon |
| 5,573,548 A | 11/1996 | Nazre et al. |
| 5,578,045 A | 11/1996 | Das |
| 5,582,616 A | 12/1996 | Bolduc et al. |
| 5,584,835 A | 12/1996 | Greenfield |
| 5,584,859 A | 12/1996 | Brotz |
| 5,601,557 A | 2/1997 | Hayhurst |
| 5,603,718 A | 2/1997 | Xu |
| 5,613,974 A | 3/1997 | Andreas et al. |
| 5,613,975 A | 3/1997 | Christy |
| 5,626,614 A | 5/1997 | Hart |
| 5,630,540 A | 5/1997 | Blewett |
| 5,632,752 A | 5/1997 | Buelna |
| 5,643,274 A | 7/1997 | Sander et al. |
| 5,643,295 A | 7/1997 | Yoon |
| 5,643,317 A | 7/1997 | Pavcnik et al. |
| 5,643,320 A | 7/1997 | Lower et al. |
| 5,658,312 A | 8/1997 | Green et al. |
| 5,658,313 A | 8/1997 | Thal |
| 5,662,654 A | 9/1997 | Thompson |
| 5,662,662 A | 9/1997 | Bishop et al. |
| 5,662,663 A | 9/1997 | Shallman |
| 5,665,109 A | 9/1997 | Yoon |

| Patent | Date | Inventor |
|---|---|---|
| 5,665,112 A | 9/1997 | Thal |
| 5,667,513 A | 9/1997 | Torrie et al. |
| 5,679,005 A | 10/1997 | Einstein |
| 5,683,417 A | 11/1997 | Cooper |
| 5,683,419 A | 11/1997 | Thal |
| 5,690,655 A | 11/1997 | Hart et al. |
| 5,693,060 A | 12/1997 | Martin |
| 5,700,273 A | 12/1997 | Buelna et al. |
| 5,702,397 A | 12/1997 | Goble et al. |
| 5,702,421 A | 12/1997 | Schneidt |
| 5,707,394 A | 1/1998 | Miller et al. |
| 5,709,708 A | 1/1998 | Thal |
| 5,713,903 A | 2/1998 | Sander et al. |
| 5,720,765 A | 2/1998 | Thal |
| 5,724,978 A | 3/1998 | Tenhoff |
| 5,725,552 A | 3/1998 | Kotula et al. |
| 5,732,707 A | 3/1998 | Widder et al. |
| 5,741,297 A | 4/1998 | Simon |
| 5,746,752 A | 5/1998 | Burkhart |
| 5,746,755 A | 5/1998 | Wood et al. |
| 5,752,963 A | 5/1998 | Allard et al. |
| 5,766,189 A | 6/1998 | Matsuno |
| 5,776,150 A | 7/1998 | Nolan et al. |
| 5,779,719 A | 7/1998 | Klein et al. |
| 5,782,865 A | 7/1998 | Grotz |
| 5,792,152 A | 8/1998 | Klein et al. |
| 5,797,929 A | 8/1998 | Andreas et al. |
| 5,797,960 A | 8/1998 | Stevens et al. |
| 5,810,849 A | 9/1998 | Kontos |
| 5,810,851 A | 9/1998 | Yoon |
| 5,810,853 A | 9/1998 | Yoon |
| 5,814,070 A | 9/1998 | Borzone et al. |
| 5,817,107 A | 10/1998 | Schaller |
| 5,817,110 A | 10/1998 | Kronner |
| 5,823,956 A | 10/1998 | Roth et al. |
| 5,824,011 A | 10/1998 | Stone et al. |
| 5,827,298 A | 10/1998 | Hart et al. |
| 5,829,447 A | 11/1998 | Stevens et al. |
| 5,836,955 A | 11/1998 | Buelna et al. |
| 5,840,078 A | 11/1998 | Yerys |
| 5,843,084 A | 12/1998 | Hart et al. |
| 5,843,126 A | 12/1998 | Jameel |
| 5,846,261 A | 12/1998 | Kotula et al. |
| 5,855,614 A | 1/1999 | Stevens et al. |
| 5,860,991 A | 1/1999 | Klein et al. |
| 5,861,003 A | 1/1999 | Latson et al. |
| 5,868,762 A | 2/1999 | Cragg et al. |
| 5,879,371 A | 3/1999 | Gardiner et al. |
| 5,888,247 A | 3/1999 | Benetti |
| 5,891,168 A | 4/1999 | Thal |
| 5,893,856 A | 4/1999 | Jacobs et al. |
| 5,895,404 A | 4/1999 | Ruiz |
| 5,899,920 A | 5/1999 | DeSatnick et al. |
| 5,899,921 A | 5/1999 | Caspari et al. |
| 5,916,224 A | 6/1999 | Esplin |
| 5,925,059 A | 7/1999 | Palermo et al. |
| 5,928,260 A | 7/1999 | Chin et al. |
| 5,928,264 A | 7/1999 | Sugarbaker et al. |
| 5,944,738 A | 8/1999 | Amplatz et al. |
| 5,947,997 A | 9/1999 | Pavcnik et al. |
| 5,948,001 A | 9/1999 | Larsen |
| 5,954,732 A | 9/1999 | Hart et al. |
| 5,961,440 A | 10/1999 | Schweich, Jr. et al. |
| 5,964,765 A | 10/1999 | Fenton, Jr. et al. |
| 5,964,783 A | 10/1999 | Grafton et al. |
| 5,976,127 A | 11/1999 | Lax |
| 5,976,158 A | 11/1999 | Adams et al. |
| 5,976,159 A | 11/1999 | Bolduc et al. |
| 5,980,558 A | 11/1999 | Wiley |
| 5,984,933 A | 11/1999 | Yoon |
| 5,993,476 A | 11/1999 | Groiso |
| 6,013,083 A | 1/2000 | Bennett |
| 6,027,523 A | 2/2000 | Schmieding |
| 6,033,430 A | 3/2000 | Bonutti |
| 6,036,699 A | 3/2000 | Andreas et al. |
| 6,045,497 A | 4/2000 | Schweich, Jr. et al. |
| 6,045,573 A | 4/2000 | Wenstrom, Jr. et al. |
| 6,050,936 A | 4/2000 | Schweich, Jr. et al. |
| 6,053,935 A | 4/2000 | Brenneman et al. |
| 6,059,715 A | 5/2000 | Schweich, Jr. et al. |
| 6,074,401 A | 6/2000 | Gardiner et al. |
| 6,077,214 A | 6/2000 | Mortier et al. |
| 6,077,281 A | 6/2000 | Das |
| 6,077,291 A | 6/2000 | Das |
| 6,079,414 A | 6/2000 | Roth et al. |
| 6,110,183 A | 8/2000 | Cope |
| 6,113,609 A | 9/2000 | Adams et al. |
| 6,113,611 A | 9/2000 | Allen et al. |
| 6,149,658 A | 11/2000 | Gardiner et al. |
| 6,152,935 A | 11/2000 | Kammerer et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,167,889 B1 | 1/2001 | Benetti |
| 6,171,320 B1 | 1/2001 | Monassevitch |
| 6,174,323 B1 | 1/2001 | Biggs et al. |
| 6,183,411 B1 | 2/2001 | Mortier et al. |
| RE37,117 E | 3/2001 | Palermo |
| 6,214,007 B1 | 4/2001 | Anderson |
| 6,231,561 B1 | 5/2001 | Frazier et al. |
| 6,241,748 B1 * | 6/2001 | Adams ....................... 606/220 |
| 6,245,079 B1 | 6/2001 | Nobles et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,270,515 B1 | 8/2001 | Linden et al. |
| 6,283,973 B1 | 9/2001 | Hubbard et al. |
| 6,290,674 B1 | 9/2001 | Roue et al. |
| 6,293,956 B1 | 9/2001 | Crainich et al. |
| 6,296,656 B1 | 10/2001 | Bolduc et al. |
| 6,306,159 B1 | 10/2001 | Schwartz et al. |
| 6,312,437 B1 | 11/2001 | Kortenbach |
| 6,315,789 B1 | 11/2001 | Cragg |
| 6,322,563 B1 | 11/2001 | Cummings et al. |
| 6,322,580 B1 | 11/2001 | Kanner |
| 6,332,468 B1 | 12/2001 | Benetti |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,336,940 B1 | 1/2002 | Graf et al. |
| 6,346,074 B1 | 2/2002 | Roth |
| 6,348,064 B1 | 2/2002 | Kanner |
| 6,355,052 B1 | 3/2002 | Neuss et al. |
| 6,363,938 B2 | 4/2002 | Saadat et al. |
| 6,368,338 B1 | 4/2002 | Konya et al. |
| 6,368,339 B1 | 4/2002 | Amplatz et al. |
| 6,387,104 B1 | 5/2002 | Pugsley, Jr. et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,423,087 B1 | 7/2002 | Sawada |
| 6,425,911 B1 | 7/2002 | Akerfeldt et al. |
| 6,447,533 B1 | 9/2002 | Adams et al. |
| 6,491,714 B1 * | 12/2002 | Bennett ....................... 606/232 |
| 6,508,828 B1 | 1/2003 | Akerfeldt et al. |
| 6,589,208 B2 | 7/2003 | Ewers et al. |
| 6,592,596 B1 | 7/2003 | Geitz |
| 6,656,194 B1 | 12/2003 | Gannoe et al. |
| 6,692,506 B1 | 2/2004 | Ory et al. |
| 6,736,828 B1 | 5/2004 | Adams et al. |
| 6,746,460 B2 | 6/2004 | Gannoe et al. |
| 6,932,834 B2 | 8/2005 | Lizardi et al. |
| 6,986,781 B2 | 1/2006 | Smith |
| 7,160,312 B2 | 1/2007 | Saadat |
| 2001/0016675 A1 | 8/2001 | Mortier et al. |
| 2001/0025171 A1 | 9/2001 | Mortier et al. |

| | | | | | | |
|---|---|---|---|---|---|---|
| 2001/0051815 A1 | 12/2001 | Esplin | | 2005/0251209 A1 | 11/2005 | Saadat et al. |
| 2002/0010490 A1 | 1/2002 | Schaller et al. | | 2005/0251210 A1 | 11/2005 | Westra et al. |
| 2002/0013608 A1 | 1/2002 | ElAttrache et al. | | 2005/0267523 A1 | 12/2005 | Devellian et al. |
| 2002/0019649 A1 | 2/2002 | Sikora et al. | | 2005/0272977 A1 | 12/2005 | Saadat et al. |
| 2002/0022851 A1 | 2/2002 | Kalloo et al. | | 2005/0273135 A1 | 12/2005 | Chanduszko et al. |
| 2002/0029080 A1 | 3/2002 | Mortier et al. | | 2005/0277945 A1 | 12/2005 | Saadat et al. |
| 2002/0049458 A1 | 4/2002 | Singhatat | | 2005/0277966 A1 | 12/2005 | Ewers et al. |
| 2002/0058855 A1 | 5/2002 | Schweich, Jr. et al. | | 2005/0277975 A1 | 12/2005 | Saadat et al. |
| 2002/0068849 A1 | 6/2002 | Schweich, Jr. et al. | | 2005/0277981 A1 | 12/2005 | Maahs et al. |
| 2002/0077524 A1 | 6/2002 | Schweich, Jr. et al. | | 2005/0277983 A1 | 12/2005 | Saadat et al. |
| 2002/0082621 A1 | 6/2002 | Schurr et al. | | 2006/0009789 A1 | 1/2006 | Gambale et al. |
| 2002/0082622 A1 | 6/2002 | Kane | | 2006/0020274 A1 | 1/2006 | Ewers et al. |
| 2002/0107530 A1 | 8/2002 | Sauer et al. | | 2006/0020276 A1 | 1/2006 | Saadat et al. |
| 2002/0116012 A1 | 8/2002 | May et al. | | 2006/0100579 A1 | 5/2006 | Maahs et al. |
| 2002/0183768 A1 | 12/2002 | Deem et al. | | 2006/0135971 A1 | 6/2006 | Swanstrom et al. |
| 2003/0109900 A1 | 6/2003 | Martinek | | 2006/0157067 A1 | 7/2006 | Saadat et al. |
| 2003/0158582 A1 | 8/2003 | Bonutti et al. | | 2006/0161185 A1 | 7/2006 | Saadat et al. |
| 2003/0167062 A1 | 9/2003 | Gambale et al. | | 2006/0178560 A1 | 8/2006 | Saadat et al. |
| 2003/0176890 A1 | 9/2003 | Buckman et al. | | 2006/0178562 A1 | 8/2006 | Saadat et al. |
| 2003/0240205 | 10/2003 | Sauer et al. | | 2006/0183975 A1 | 8/2006 | Saadat et al. |
| 2004/0030347 A1 | 2/2004 | Gannoe et al. | | 2006/0184161 A1 | 8/2006 | Maahs et al. |
| 2004/0088008 A1 | 5/2004 | Gannoe et al. | | 2006/0189845 A1 | 8/2006 | Maahs et al. |
| 2004/0093091 A1 | 5/2004 | Gannoe et al. | | 2006/0217762 A1 | 9/2006 | Maahs et al. |
| 2004/0116949 A1 | 6/2004 | Ewers et al. | | 2006/0237022 A1 | 10/2006 | Chen et al. |
| 2004/0122456 A1 | 6/2004 | Saadat et al. | | 2006/0237023 A1 | 10/2006 | Cox et al. |
| 2004/0122473 A1 | 6/2004 | Ewers et al. | | 2006/0258909 A1 | 11/2006 | Saadat et al. |
| 2004/0122474 A1 | 6/2004 | Gellman et al. | | 2006/0271073 A1 | 11/2006 | Lam et al. |
| 2004/0147958 A1 | 7/2004 | Lam et al. | | 2006/0271074 A1 | 11/2006 | Ewers et al. |
| 2004/0162568 A1 | 8/2004 | Saadat et al. | | 2006/0271101 A1 | 11/2006 | Saadat et al. |
| 2004/0167546 A1 | 8/2004 | Saadat et al. | | 2007/0123840 A1 | 5/2007 | Cox |
| 2004/0176784 A1 | 9/2004 | Okada | | 2007/0142849 A1 | 6/2007 | Ewers et al. |
| 2004/0225183 A1 | 11/2004 | Michlitsch et al. | | | | |
| 2004/0225305 A1 | 11/2004 | Ewers et al. | | | FOREIGN PATENT DOCUMENTS | |
| 2004/0249367 A1 | 12/2004 | Saadat et al. | | EP | 1 031 321 A1 | 8/2000 |
| 2004/0249392 A1 | 12/2004 | Mikkaichi et al. | | EP | 1648279 | 4/2006 |
| 2004/0249395 A1 | 12/2004 | Mikkaichi et al. | | EP | 1699366 | 9/2006 |
| 2005/0065397 A1 | 3/2005 | Saadat et al. | | EP | 1781184 | 5/2007 |
| 2005/0065401 A1 | 3/2005 | Saadat et al. | | EP | 1804680 | 7/2007 |
| 2005/0065536 A1 | 3/2005 | Ewers et al. | | EP | 1804683 | 7/2007 |
| 2005/0075653 A1 | 4/2005 | Saadat et al. | | JP | 2007-513717 | 5/2007 |
| 2005/0075654 A1 | 4/2005 | Kelleher et al. | | WO | WO 95/19140 A1 | 7/1995 |
| 2005/0113640 A1 | 5/2005 | Saadat et al. | | WO | WO 00/40159 A1 | 7/2000 |
| 2005/0119671 A1 | 6/2005 | Reydel et al. | | WO | WO 00/57796 A1 | 10/2000 |
| 2005/0149115 A1 | 7/2005 | Roue et al. | | WO | WO 01/21246 A1 | 3/2001 |
| 2005/0192629 A1 | 9/2005 | Saadat et al. | | WO | WO 01/66001 A2 | 9/2001 |
| 2005/0203488 A1 | 9/2005 | Michlitsch et al. | | WO | WO 01/85034 A1 | 11/2001 |
| 2005/0203489 A1 | 9/2005 | Saadat et al. | | WO | WO 01/89392 A2 | 11/2001 |
| 2005/0203500 A1 | 9/2005 | Saadat et al. | | WO | WO 02/00119 A2 | 1/2002 |
| 2005/0234294 A1 | 10/2005 | Saadat et al. | | WO | WO 02/064012 A2 | 8/2002 |
| 2005/0234296 A1 | 10/2005 | Saadat et al. | | WO | WO 02/085252 A1 | 10/2002 |
| 2005/0245945 A1 | 11/2005 | Ewers et al. | | WO | WO 02/094105 A2 | 11/2002 |
| 2005/0250980 A1 | 11/2005 | Swanstrom et al. | | WO | WO 03/007799 A2 | 1/2003 |
| 2005/0250984 A1 | 11/2005 | Lam et al. | | WO | WO 03/092509 A1 | 11/2003 |
| 2005/0250985 A1 | 11/2005 | Saadat et al. | | WO | WO 2004/019787 A2 | 3/2004 |
| 2005/0250986 A1 | 11/2005 | Rothe et al. | | WO | WO 2004/019788 A2 | 3/2004 |
| 2005/0250987 A1 | 11/2005 | Ewers et al. | | WO | WO 2004/041119 | 5/2004 |
| 2005/0250988 A1 | 11/2005 | Ewers et al. | | WO | WO 2004/056273 A1 | 7/2004 |
| 2005/0251091 A1 | 11/2005 | Saadat et al. | | WO | WO 2004/064600 | 8/2004 |
| 2005/0251157 A1 | 11/2005 | Saadat et al. | | WO | WO 2004/075787 A1 | 9/2004 |
| 2005/0251158 A1 | 11/2005 | Saadat et al. | | WO | WO 2004/103430 | 12/2004 |
| 2005/0251159 A1 | 11/2005 | Ewers et al. | | WO | WO 2004/110285 | 12/2004 |
| 2005/0251160 A1 | 11/2005 | Saadat et al. | | WO | WO 2005/004727 A1 | 1/2005 |
| 2005/0251161 A1 | 11/2005 | Saadat et al. | | WO | WO 2005/011463 | 2/2005 |
| 2005/0251162 A1 | 11/2005 | Rothe et al. | | WO | WO 2005/011519 | 2/2005 |
| 2005/0251165 A1 | 11/2005 | Vaughan et al. | | WO | WO 2005/037152 | 4/2005 |
| 2005/0251166 A1 | 11/2005 | Vaughan et al. | | WO | WO 2005/048815 | 6/2005 |
| 2005/0251176 A1 | 11/2005 | Swanstrom et al. | | WO | WO 2005/050971 | 6/2005 |
| 2005/0251177 A1 | 11/2005 | Saadat et al. | | WO | WO 2005/058239 | 6/2005 |
| 2005/0251189 A1 | 11/2005 | Saadat et al. | | WO | WO 2005/086945 | 9/2005 |
| 2005/0251202 A1 | 11/2005 | Ewers et al. | | WO | WO 2005/104927 | 11/2005 |
| 2005/0251205 A1 | 11/2005 | Ewers et al. | | WO | WO 2005/110244 | 11/2005 |
| 2005/0251206 A1 | 11/2005 | Maahs et al. | | WO | WO 2005/122914 | 12/2005 |
| 2005/0251207 A1 | 11/2005 | Flores et al. | | | | |

| WO | WO 2005/122915 | 12/2005 |
| --- | --- | --- |
| WO | WO 2006/019868 | 2/2006 |
| WO | WO 2006/039199 | 4/2006 |
| WO | WO 2006/039223 | 4/2006 |
| WO | WO 2006/039296 | 4/2006 |
| WO | WO 2006/078429 | 7/2006 |
| WO | WO 2006/089217 | 8/2006 |
| WO | WO 2006/093975 | 9/2006 |
| WO | WO 2006/110275 | 10/2006 |
| WO | WO 2006/127306 | 11/2006 |
| WO | WO 2007/009021 | 1/2007 |

OTHER PUBLICATIONS

Bluett et al., "Experimental Evaluation of Staple Lines in Gastric Surgery," *Arch. Surg.*, vol. 122, (Jul. 1987), pp. 772-776.

Brolin et al., Experimental Evaluation of Techniques of Gastric Paritioning for Morbid Obesity, *Surgery, Gynecology & Obstetrics*, vol. 153, (Dec. 1981), pp. 878-882.

Okudaira et al., "The Healing and Tensile Strength of the Gastroplasty Staple Line," *The American Surgeon*, Oct. 1984, pp. 564-568.

Surgical Dynamics Inc., The S•D•sorb Meniscal Stapler [brochure] (1997), 3 pages total.

Sutura, The Next Generation in Vascular Suturing Devices: SuperStitch [brochure], 2 pages total.

U.S. Appl. No. 10/612,170 filed Jul. 1, 2003, in the name of Saadat et al., Advisory Action mailed Nov. 3, 2006.

U.S. Appl. No. 10/612,170 filed Jul. 1, 2003, in the name of Saadat et al., Final Office Action maile Mar. 29, 2006.

U.S. Appl. No. 10/612,170 filed Jul. 1, 2003, in the name of Saadat et al., Final Office Action mailed Nov. 21, 2007.

U.S. Appl. No. 10/612,170 filed Jul. 1, 2003, in the name of Saadat et al., Non-final Office Action mailed Apr. 3, 2007.

U.S. Appl. No. 10/612,170 filed Jul. 1, 2003, in the name of Saadat et al., Non-final Office Action mailed Apr. 23, 2008.

U.S. Appl. No. 10/612,170 filed Jul. 1, 2003, in the name of Saadat et al., Request for Continued Examination filed Sep. 28, 2008.

U.S. Appl. No. 10/612,170 filed Jul. 1, 2003, in the name of Saadat et al., Response to final Office Action filed Feb. 15, 2008.

U.S. Appl. No. 10/612,170 filed Jul. 1, 2003, in the name of Saadat et al., Response to Non-final Office Action filed Aug. 3, 2007.

U.S. Appl. No. 10/612,170 filed Jul. 1, 2003, in the name of Saadat et al., Response to Non-final Office Action filed Sep. 23, 2008.

U.S. Appl. No. 10/612,491 filed Jul. 1, 2003, in the name of Saadat et al., Appeal Brief filed Feb. 12, 2009.

U.S. Appl. No. 10/612,491 filed Jul. 1, 2003, in the name of Saadat et al., Final Office Action mailed Apr. 15, 2008.

U.S. Appl. No. 10/612,491 filed Jul. 1, 2003, in the name of Saadat et al., Final Office Action mailed Apr. 17, 2007.

U.S. Appl. No. 10/612,491 filed Jul. 1, 2003, in the name of Saadat et al., Non-final Office Action mailed Jul. 9, 2007.

U.S. Appl. No. 10/612,491 filed Jul. 1, 2003, in the name of Saadat et al., Non-final Office Action mailed May 26, 2009.

U.S. Appl. No. 10/612,491 filed Jul. 1, 2003, in the name of Saadat et al., Non-final Office Action mailed Sep. 19, 2006.

U.S. Appl. No. 10/612,491 filed Jul. 1, 2003, in the name of Saadat et al., Notice of Appeal filed Sep. 12, 2008.

U.S. Appl. No. 10/612,491 filed Jul. 1, 2003, in the name of Saadat et al., Request for Continued Examination filed Jun. 19, 2007.

U.S. Appl. No. 10/612,491 filed Jul. 1, 2003, in the name of Saadat et al., Response to Non-final Action filed Feb. 20, 2077.

U.S. Appl. No. 10/612,491 filed Jul. 1, 2003, in the name of Saadat et al., Response to Non-final Office Action filed Nov. 15, 2007.

U.S. Appl. No. 10/612,491 filed Jul. 1, 2003, in the name of Saadat et al., Response to Non-final Office Action filed Nov. 25, 2009.

U.S. Appl. No. 10/612,491 filed Jul. 1, 2003, in the name of Saadat et al., Response to Restriction Requirement filed Sep. 13, 2006.

U.S. Appl. No. 10/612,491 filed Jul. 1, 2003, in the name of Saadat et al., Restriction Requirement mailed Sep. 5, 2006.

U.S. Appl. No. 10/840,950 filed May 7, 2004, in the name of Saadat et al., Request for Continued Examination filed Oct. 21, 2009.

U.S. Appl. No. 10/840,950 filed May 7, 2004, in the name of Saadat et al., Supplemental IDS filed Oct. 21, 2010.

U.S. Appl. No. 10/840,950 filed May 7, 2004, in the name of Saadat et al., Response to Non-final Office Action filed Feb. 4, 2009.

U.S. Appl. No. 10/840,950 filed May 7, 2004, in the name of Saadat et al., Response to Restriction Requirement filed May 5, 2008.

U.S. Appl. No. 10/840,950 filed May 7, 2004, in the name of Saadat et al., Restriction Requirement mailed Apr. 4, 2008.

U.S. Appl. No. 10/840,950 filed May 7, 2004, in the name of Saadat et al., Supplemental IDS filed Dec. 21, 2007.

U.S. Appl. No. 10/840,950 filed May 7, 2004, in the name of Saadat et al., Supplemental IDS filed Jan. 7, 2008.

U.S. Appl. No. 10/840,951 filed May 7, 2004, in the name of Ewers et al., Final Office Action mailed Jun. 25, 2008.

U.S. Appl. No. 10/840,951 filed May 7, 2004, in the name of Ewers et al., Non-final Office Action mailed Apr. 11, 2007.

U.S. Appl. No. 10/840,951 filed May 7, 2004, in the name of Ewers et al., Non-final Office Action mailed Mar. 4, 2009.

U.S. Appl. No. 10/840,951 filed May 7, 2004, in the name of Ewers et al., Non-final Office Action mailed Sep. 18, 2007.

U.S. Appl. No. 10/840,951 filed May 7, 2004, in the name of Ewers et al., Request for Continued Examination filed Nov. 25, 2008.

U.S. Appl. No. 10/840,951 filed May 7, 2004, in the name of Ewers et al., Response to Non-final Office Action filed Aug. 4, 2009.

U.S. Appl. No. 10/840,951 filed May 7, 2004, in the name of Ewers et al., Response to Non-final Office Action filed Jul. 12, 2007.

U.S. Appl. No. 10/840,951 filed May 7, 2004, in the name of Ewers et al., Response to Non-final Office Action filed Mar. 18, 2008.

U.S. Appl. No. 10/840,951 filed May 7, 2004, in the name of Ewers et al., Response to Restriction Requirement filed Jan. 5, 2007.

U.S. Appl. No. 10/840,951 filed May 7, 2004, in the name of Ewers et al., Restriction Requirement mailed Sep. 5, 2006.

U.S. Appl. No. 10/841,411 filed May 7, 2004, in the name of Flores et al., Notice of Panel Decision from Pre-Appeal Brief Review mailed May 5, 2009.

U.S. Appl. No. 10/841,411 filed May 7, 2004, in the name of Flores et al., Final Office Action mailed Aug. 15, 2007.

U.S. Appl. No. 10/841,411 filed May 7, 2004, in the name of Flores et al., Final Office Action mailed Nov. 6, 2008.

U.S. Appl. No. 10/841,411 filed May 7, 2004, in the name of Flores et al., Non-final Office Action mailed Feb. 12, 2007.

U.S. Appl. No. 10/841,411 filed May 7, 2004, in the name of Flores et al., Non-final Office Action mailed Jan. 22, 2008.

U.S. Appl. No. 10/841,411 filed May 7, 2004, in the name of Flores et al., Non-final Office Action mailed Jul. 21, 2009.

U.S. Appl. No. 10/841,411 filed May 7, 2004, in the name of Flores et al., Appeal Brief Request and Notice of Appeal filed Mar. 6, 2009.

U.S. Appl. No. 10/841,411 filed May 7, 2004, in the name of Flores et al., Request of Continued Examination filed Oct. 29, 2007.

U.S. Appl. No. 10/841,411 filed May 7, 2004, in the name of Flores et al., Response to Non-final Office Action filed Dec. 21, 2009.

U.S. Appl. No. 10/841,411 filed May 7, 2004, in the name of Flores et al., Response to Non-final Office Action filed Jul. 22, 2008.

U.S. Appl. No. 10/841,411 filed May 7, 2004, in the name of Flores et al., Response to Non-final Office Action filed May 11, 2007.

U.S. Appl. No. 10/841,411 filed May 7, 2004, in the name of Flores et al., Response to Restriction Requirement filed Jan. 8, 2007.

U.S. Appl. No. 10/841,411 filed May 7, 2004, in the name of Flores et al., Restriction Requirement mailed Oct. 19, 2006.

U.S. Appl. No. 10/841,411 filed May 7, 2004, in the name of Flores et al., Supplemental IDS filed Dec. 27, 2007.

U.S. Appl. No. 10/841,411 filed May 7, 2004, in the name of Flores et al., Supplemental IDS filed Jan. 7, 2008.

U.S. Appl. No. 10/869,472 filed Jun. 15, 2004, in the name of Elmer et al., Non-final Office Action mailed Dec. 24, 2008.

U.S. Appl. No. 10/869,472 filed Jun. 15, 2004, in the name of Elmer et al., Non-final Office Action mailed Mar. 26, 2008.

U.S. Appl. No. 10/869,472 filed Jun. 15, 2004, in the name of Elmer et al., Response to Non-final Office Action filed Jun. 24, 2009.

U.S. Appl. No. 10/869,472 filed Jun. 15, 2004, in the name of Elmer et al., Response to Non-final Office Action filed Sep. 26, 2008.

U.S. Appl. No. 10/869,472 filed Jun. 15, 2004, in the name of Elmer et al., Supplemental IDS filed Dec. 24, 2007.

U.S. Appl. No. 10/869,472 filed Jun. 15, 2004, in the name of Elmer et al., Supplemental IDS filed Jan. 7, 2008.
U.S. Appl. No. 10/954,665 filed Sep. 29, 2004, in the name of Ewers et al., Non-final Office Action mailed Dec. 24, 2008.
U.S. Appl. No. 10/954,665 filed Sep. 29, 2004, in the name of Ewers et al., Non-final Office Action mailed Mar. 26, 2008.
U.S. Appl. No. 10/954,665 filed Sep. 29, 2004, in the name of Ewers et al., Response to Non-final Office Action filed Jan. 27, 2010.
U.S. Appl. No. 10/954,665 filed Sep. 29, 2004, in the name of Ewers et al., Response to Restriction Requirement filed Jun. 2, 2009.
U.S. Appl. No. 10/954,665 filed Sep. 29, 2004, in the name of Ewers et al., Restriction Requirement mailed Apr. 2, 2009.
U.S. Appl. No. 10/954,665 filed Sep. 29, 2004, in the name of Ewers et al., Supplemental IDS filed Dec. 26, 2007.
U.S. Appl. No. 10/954,665 filed Sep. 29, 2004, in the name of Ewers et al., Supplemental IDS filed Jan. 7, 2008.
U.S. Appl. No. 10/036,866 filed Jan. 14, 2005, in the name of Saadat et al., Final Office Action mailed Mar. 24, 2008.
U.S. Appl. No. 10/036,866 filed Jan. 14, 2005, in the name of Saadat et al., Non-final Office Action mailed Apr. 21, 2009.
U.S. Appl. No. 10/036,866 filed Jan. 14, 2005, in the name of Saadat et al., Non-final Office Action mailed Jun. 29, 2007.
U.S. Appl. No. 10/036,866 filed Jan. 14, 2005, in the name of Saadat et al., Request for Continued Examination filed Jan. 26, 2009.
U.S. Appl. No. 10/036,866 filed Jan. 14, 2005, in the name of Saadat et al., Response to Non-final Office Action filed Dec. 28, 2007.
U.S. Appl. No. 10/036,866 filed Jan. 14, 2005, in the name of Saadat et al., Response to Non-final Office Action filed Sep. 21, 2009.
U.S. Appl. No. 10/036,866 filed Jan. 14, 2005, in the name of Saadat et al., Response to Restriction Requirement filed May 29, 2007.
U.S. Appl. No. 10/036,866 filed Jan. 14, 2005, in the name of Saadat et al., Restriction Requirement mailed Apr. 27, 2007.
U.S. Appl. No. 10/036,866 filed Jan. 14, 2005, in the name of Saadat et al., Supplemental IDS filed Dec. 26, 2007.
U.S. Appl. No. 10/036,866 filed Jan. 14, 2005, in the name of Saadat et al., Supplemental IDS filed Jan. 7, 2008.
U.S. Appl. No. 10/036,946 filed Jan. 14, 2005, in the name of Westra et al., Notice of Allowance mailed Sep. 11, 2007.
U.S. Appl. No. 10/036,946 filed Jan. 14, 2005, in the name of Westra et al., Request for Continued Examination filed Oct. 30, 2007.
U.S. Appl. No. 10/036,946 filed Jan. 14, 2005, in the name of Westra et al., Response to Restriction Requirement filed Jul. 2, 2007.
U.S. Appl. No. 10/036,946 filed Jan. 14, 2005, in the name of Westra et al., Restriction Requirement mailed May 30, 2007.
U.S. Appl. No. 10/036,946 filed Jan. 14, 2005, in the name of Westra et al., Supplemental IDS filed Dec. 26, 2007.
U.S. Appl. No. 10/404,423 filed Apr. 14, 2006, in the name of Maahs et al., IDS filed Oct. 16, 2009.
U.S. Appl. No. 10/404,423 filed Apr. 14, 2006, in the name of Maahs et al., Notice of Allowance mailed Nov. 5, 2009.
U.S. Appl. No. 10/404,423 filed Apr. 14, 2006, in the name of Maahs et al., Request for Continued Examination filed Oct. 16, 2009.
U.S. Appl. No. 10/404,423 filed Apr. 14, 2006, in the name of Maahs et al., Response to final Office Action filed Sep. 14, 2009.
U.S. Appl. No. 10/404,423 filed Apr. 14, 2006, in the name of Maahs et al., Response to Non-final Office Action filed Mar. 3, 2009.
U.S. Appl. No. 10/865,243 filed Jun. 9, 2004, in the name of Maahs et al., Response to Non-final Office Action filed Dec. 10, 2009.
U.S. Appl. No. 10/865,243 filed Jun. 9, 2004, in the name of Maahs et al., Response to Non-final Office Action filed Jun. 26, 2008.
U.S. Appl. No. 10/865,243 filed Jun. 9, 2004, in the name of Maahs et al., Supplemental IDS filed Dec. 10, 2009.
U.S. Appl. No. 11/179,082 filed Jul. 11, 2005, in the name of Ewers et al., Response to Non-final Office Action filed Jun. 25, 2008.
U.S. Appl. No. 11/179,082 filed Jul. 11, 2005, in the name of Ewers et al., Response to Non-final Office Action filed Oct. 13, 2009.
U.S. Appl. No. 11/179,082 filed Jul. 11, 2005, in the name of Ewers et al., Supplemental IDS filed Oct. 16, 2009.
U.S. Appl. No. 10/612,170 filed Jul. 1, 2003, in the name of Saadat et al., Final Office Action mailed Oct. 7, 2009.
U.S. Appl. No. 10/840,950 filed May 7, 2004, in the name of Saadat et al., Final Office Action mailed Apr. 21, 2009.
U.S. Appl. No. 10/840,950 filed May 7, 2004, in the name of Saadat et al., Non-final Office Action mailed Dec. 23, 2009.
U.S. Appl. No. 10/840,950 filed May 7, 2004, in the name of Saadat et al., Non-final Office Action mailed Sep. 4, 2008.
U.S. Appl. No. 10/840,951 filed May 7, 2004, in the name of Ewers et al., Final Office Action mailed Dec. 10, 2009.
U.S. Appl. No. 10/869,472 filed Jun. 15, 2004, in the name of Elmer et al., Final Office Action mailed Oct. 28, 2009.
U.S. Appl. No. 10/954,665 filed Sep. 29, 2004, in the name of Ewers et al., Non-final Office Action mailed Aug. 27, 2009.
U.S. Appl. No. 11/036,866 filed Jan. 14, 2005, in the name of Saadat et al., Final Office Action mailed Dec. 22, 2009.
U.S. Appl. No. 11/179,082 filed Jul. 11, 2005, in the name of Ewers et al., Non-final Office Action mailed Feb. 25, 2008.
U.S. Appl. No. 11/179,082 filed Jul. 11, 2005, in the name of Ewers et al., Non-final Office Action mailed Jun. 10, 2009.
U.S. Appl. No. 11/404,423 filed Apr. 14, 2006, in the name of Maahs et al., Final Office Action mailed Jun. 16, 2009.
U.S. Appl. No. 11/404,423 filed Apr. 14, 2006, in the name of Maahs et al., Non-final Office Action mailed Oct. 3, 2008.
U.S. Appl. No. 11/404,423 filed Apr. 14, 2006, in the name of Maahs et al., Notice of Allowance mailed Nov. 5, 2009.

* cited by examiner

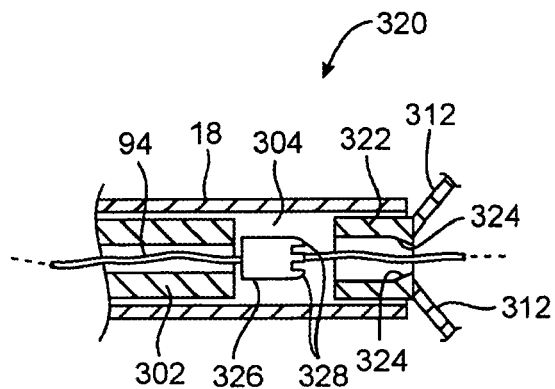
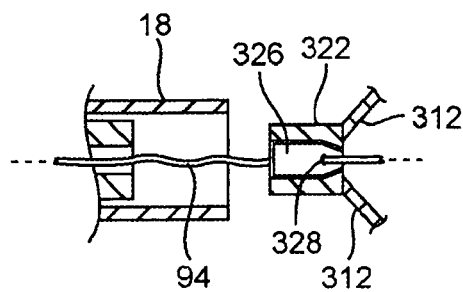
FIG. 14A    FIG. 14B
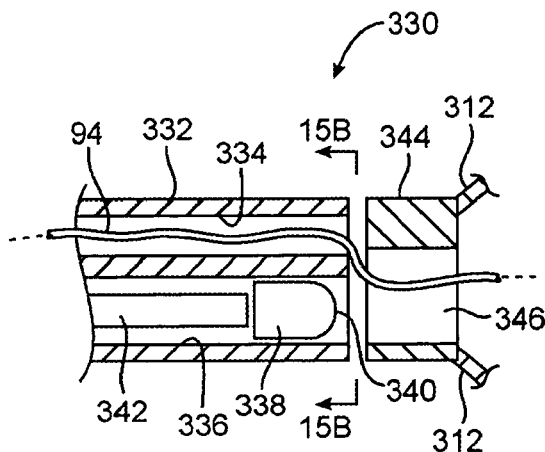
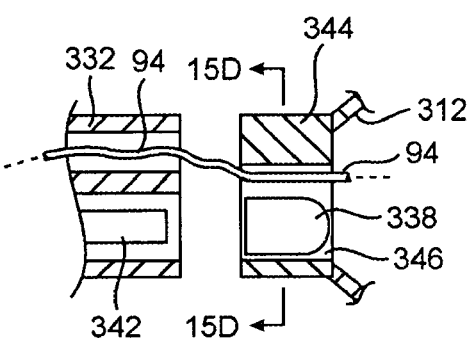
FIG. 15A    FIG. 15C
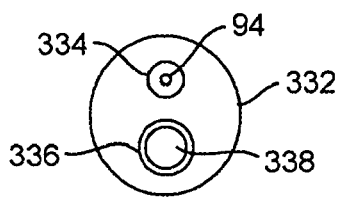
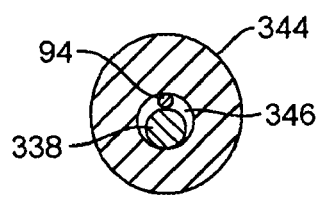
FIG. 15B    FIG. 15D

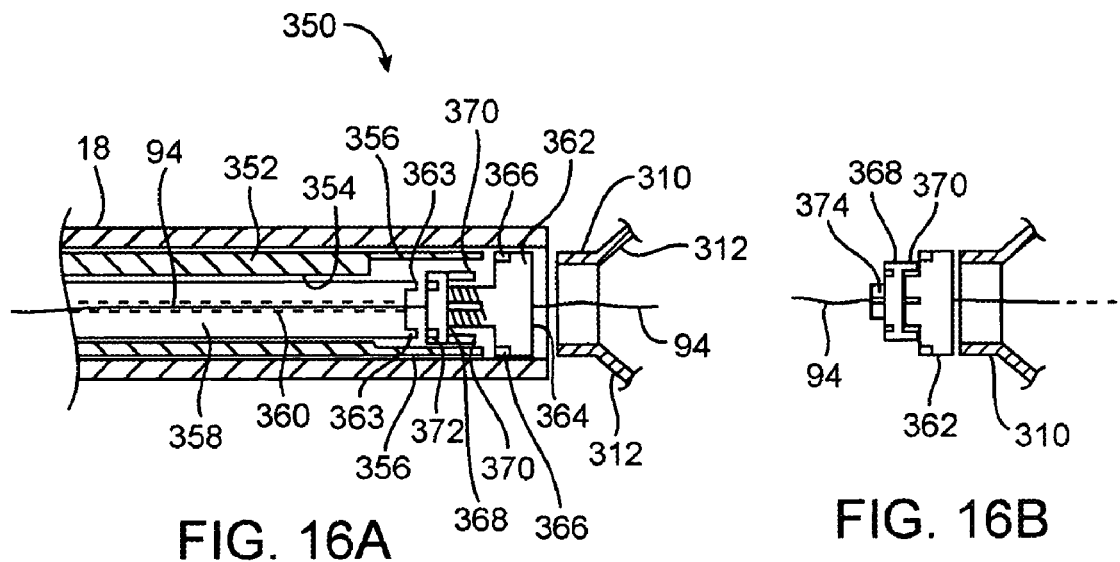
FIG. 16A
FIG. 16B
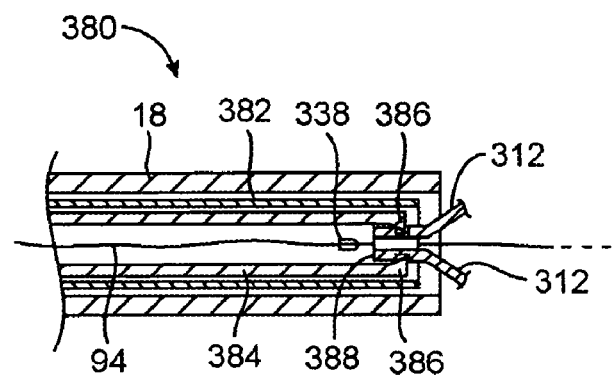
FIG. 17A
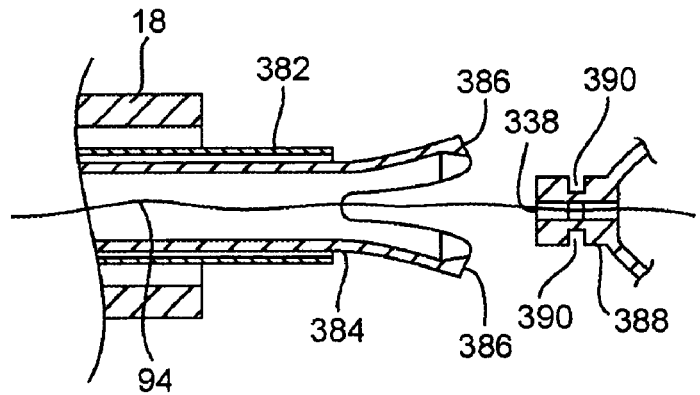
FIG. 17B

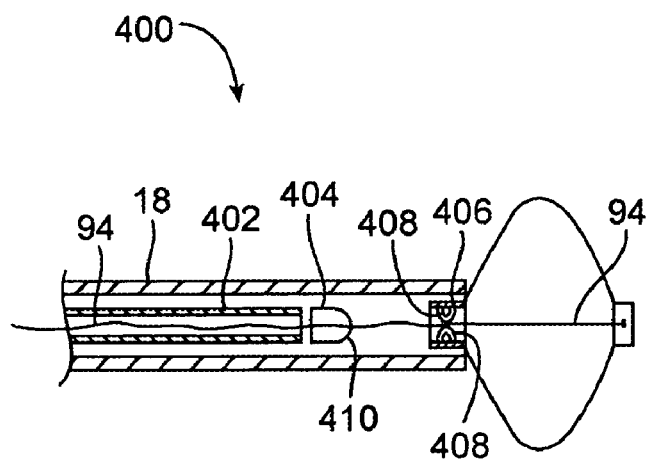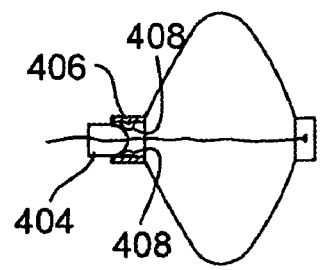
FIG. 18A  FIG. 18B
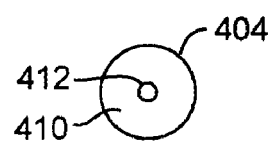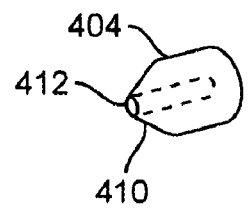
FIG. 18C  FIG. 18D
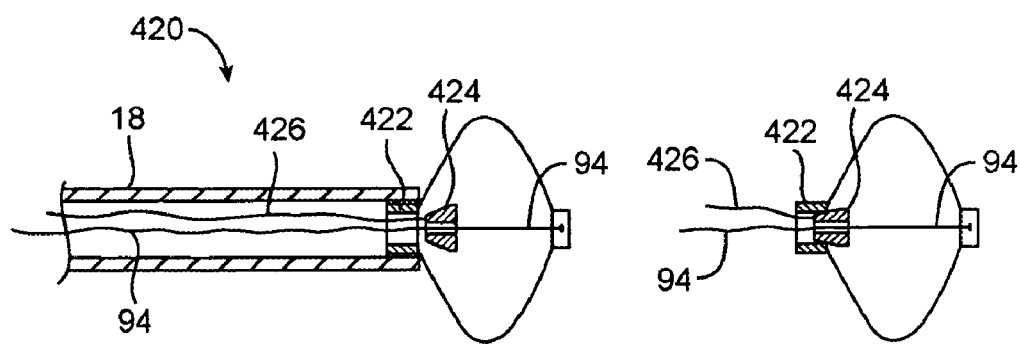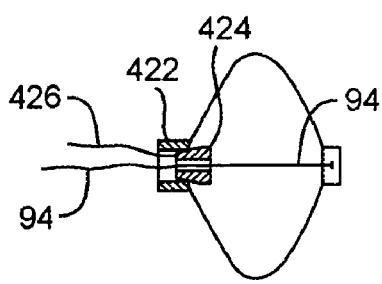
FIG. 19A  FIG. 19B

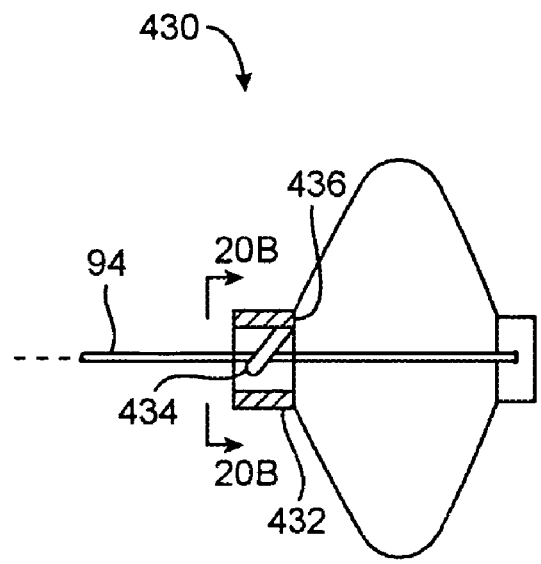
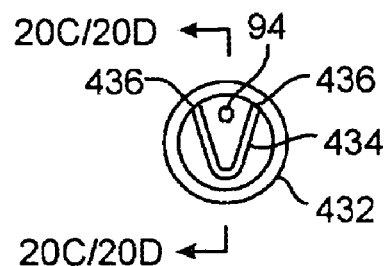
FIG. 20A
FIG. 20B
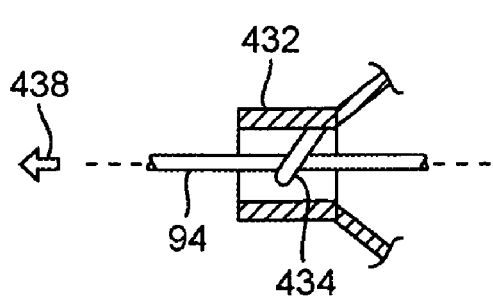
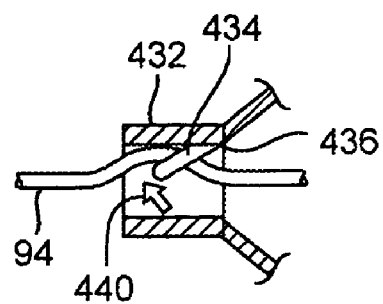
FIG. 20C
FIG. 20D

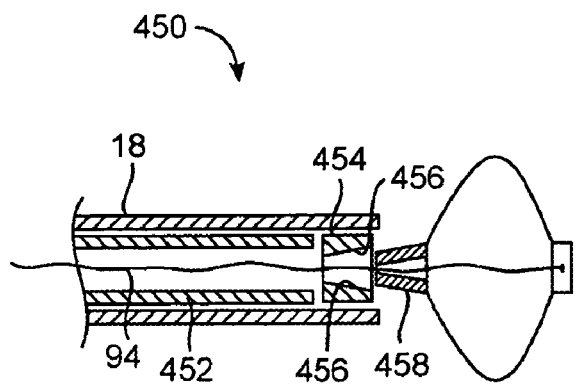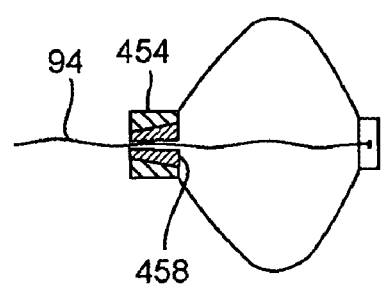
FIG. 21A  FIG. 21B
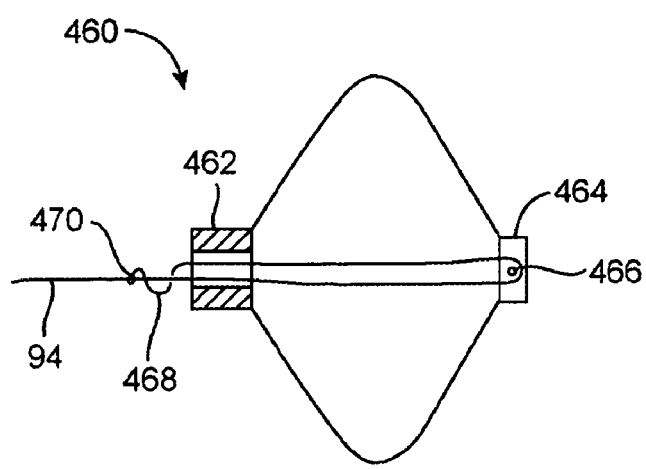
FIG. 22A

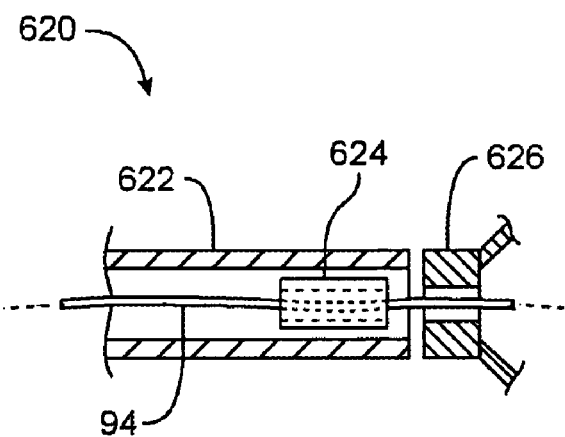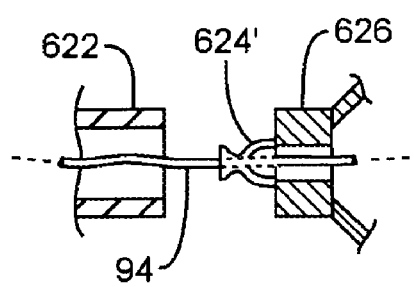
FIG. 29A  FIG. 29B
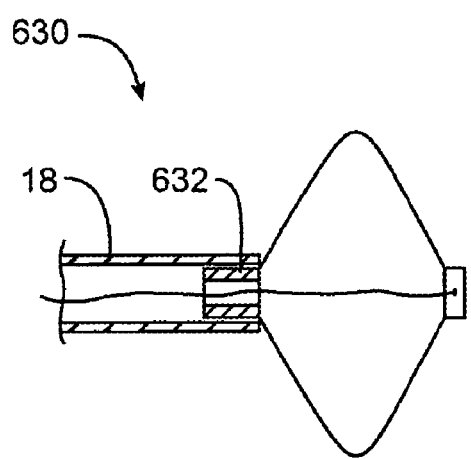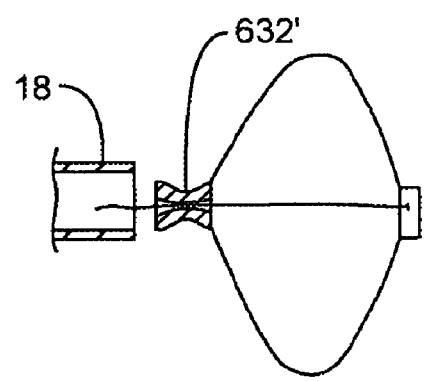
FIG. 30A  FIG. 30B

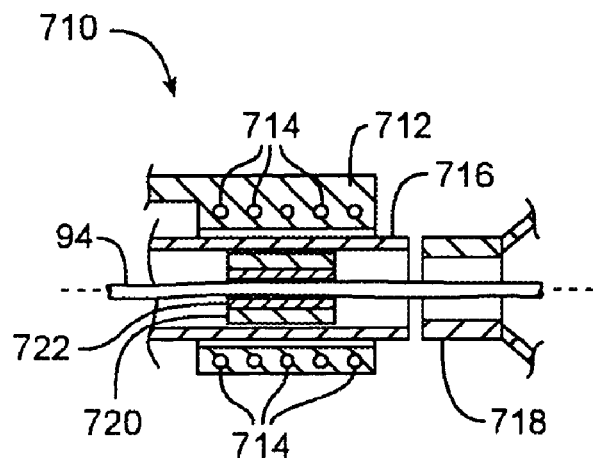
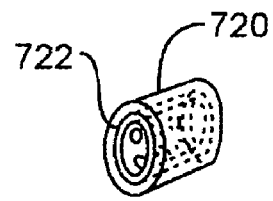
FIG. 35A     FIG. 35B
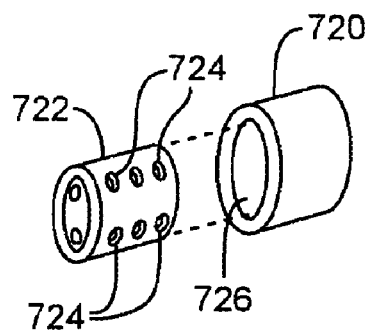
FIG. 35C
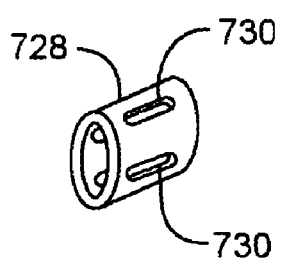 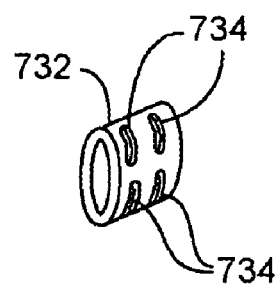
FIG. 35D     FIG. 35E

APPARATUS AND METHODS FOR POSITIONING AND SECURING ANCHORS

CROSS-REFERENCES TO RELATED APPLICATIONS

The subject matter of the present application is related to that of the following applications each of which is being filed on the same day as the present application: Ser. No. 10/840,950, entitled "Apparatus and Methods for Positioning and Securing Anchors"; Ser. No. 10/840,951, entitled "Apparatus and Methods for Positioning and Securing Anchors"; Ser. No. 10/841,411, entitled "Apparatus and Methods for Positioning and Securing Anchors"; the full disclosure of each of these applications are incorporated herein by reference.

BACKGROUND OF THE INVENTION

1. Field of the Invention

The present invention relates to apparatus and methods for positioning and securing anchors within tissue. More particularly, the present invention relates to apparatus and methods for positioning and securing anchors within folds of tissue within a body.

BRIEF SUMMARY OF THE INVENTION

2. Background of the Invention

Morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

A number of surgical techniques have been developed to treat morbid obesity, e.g., bypassing an absorptive surface of the small intestine, or reducing the stomach size. However, many conventional surgical procedures may present numerous life-threatening post-operative complications, and may cause atypical diarrhea, electrolytic imbalance, unpredictable weight loss and reflux of nutritious chyme proximal to the site of the anastomosis.

Furthermore, the sutures or staples that are often used in these surgical procedures typically require extensive training by the clinician to achieve competent use, and may concentrate significant force over a small surface area of the tissue, thereby potentially causing the suture or staple to tear through the tissue. Many of the surgical procedures require regions of tissue within the body to be approximated towards one another and reliably secured. The gastrointestinal lumen includes four tissue layers, wherein the mucosa layer is the inner-most tissue layer followed by connective tissue, the muscularis layer and the serosa layer.

One problem with conventional gastrointestinal reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesopageally rather than intraoperatively, since care must be taken in piercing the tough stomach wall not to inadvertently puncture adjacent tissue or organs.

One conventional method for securing anchors within a body lumen to the tissue is to utilize sewing devices to suture the stomach wall into folds. This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity or for GERD must be performed to completion. Accordingly, the placement and securement of the tissue plication should ideally be relatively quick and performed with a minimal level of confidence.

Another problem with conventional methods involves ensuring that the staple, knotted suture, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally.

Moreover, when grasping or clamping onto or upon the layers of tissue with conventional anchors, sutures, staples, clips, etc., may of these devices are configured to be placed only after the tissue has been plicated and not during the actual plication procedure.

BRIEF DESCRIPTION OF THE DRAWINGS

In securing plications which may be created within a body lumen of a patient, various methods and devices may be implemented. Generally, any number of conventional methods may be utilized for initially creating the plication. One method in particular may involve creating a plication through which a tissue anchor may be disposed within or through. A distal tip of a tissue plication apparatus may engage or grasp the tissue and move the engaged tissue to a proximal position relative to the tip of the device, thereby providing a substantially uniform plication of predetermined size. Examples of tools and methods which are particularly suited for delivering the anchoring and securement devices may be seen in further detail in co-pending U.S. patent application Ser. No. 10/735,030 filed Dec. 12, 2003, which is incorporated herein by reference in its entirety.

In securing these plications, various tissue anchors may be utilized for securing the plications in their configured folds. For example, a plication (or plications) may be secured via a length or lengths of suture extending through the plication and between a distally-positioned tissue anchor located on a distal side of the plication and a proximally-positioned tissue anchor located on a proximal side of the plication. Examples of anchors which may be utilized are disclosed in co-pending U.S. patent application Ser. No. 10/612,170, filed Jul. 1, 2003, which is incorporated herein by reference in its entirety.

Figure 1A:
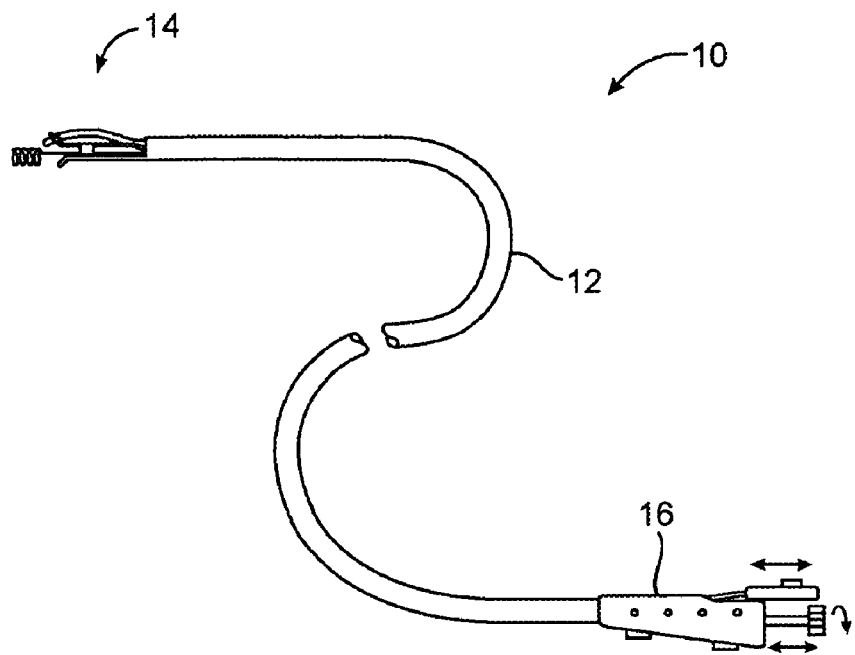

Generally, in securing a tissue plication, a proximally and/or distally located tissue anchor is preferably configured to slide along the connecting suture in a uni-directional manner. For instance, if the proximal anchor is to be slid along the suture, it is preferably configured to translate over the suture such that the tissue plication is cinched between the anchors. In this example, the proximal anchor is preferably configured to utilize a locking mechanism which allows for the free uni-directional translation of the suture therethrough while enabling the anchor to be locked onto the suture if the anchor is pulled, pushed, or otherwise urged in the opposite direction along the suture. This uni-directional anchor locking mechanism facilitates the cinching of the tissue plication between the anchors and it may be utilized in one or several of the anchors in cinching a tissue fold.

Moreover, the types of anchors utilized for the securement of tissue plications are not intended to be limiting. For instance, many of the anchor locking or cinching mechanisms may be utilized with, e.g., "T"-type anchors as well as with reconfigurable "basket"-type anchors, which generally comprise a number of configurable struts or legs extending between at least two collars or support members. Other variations of these or other types of anchors are also contemplated for use in an anchor locking or cinching assembly.

Furthermore, a single type of anchor maybe used exclusively in an anchor locking or cinching assembly; alternatively, a combination of different anchor types each utilizing different anchor locking or cinching mechanisms may be used in a single assembly. Furthermore, the different types of cinching or locking mechanisms are not intended to be limited to any of the particular variations shown and described below but may be utilized in any combinations or varying types of anchors as practicable.

The suture itself may be modified or altered to integrate features or protrusions along its length or a specified portion of its length. Such features may be defined uniformly at regular intervals along the length of suture or intermittently, depending upon the desired locking or cinching effects. Furthermore, the suture may be made from metals such as Nitinol, stainless steels, Titanium, etc., provided that they are formed suitably thin and flexible. Using metallic sutures with the anchoring mechanisms may decrease any possibilities of suture failure and it may also provide a suture better able to withstand the acidic and basic environment of the gastrointestinal system. Also, it may enhance imaging of the suture and anchor assembly if examined under imaging systems. Sutures incorporating the use of features or protrusions along its length as well as sutures fabricated from metallic materials or any other conventional suture type may be utilized with any of the locking or cinching mechanisms described below in various combinations, if so desired.

One variation for utilizing a locking mechanism which allows for free uni-directional translation of the suture through the anchor may include blocks or members which are adapted to slide within or upon an anchor to lock the suture. These blocks or members may include tapered edges which act to cleat the suture depending upon the direction the anchor is translated relative to the suture. Moreover, these blocks may be biased or urged to restrict the movement of the suture using a variety of biasing elements, such as springs, etc. In addition to blocks, one or several locking tabs which are levered to allow uni-directional travel of the suture through an anchor may also be utilized.

Aside from the use of mechanical locking features integrated within or with the anchor bodies, locking mechanisms may also utilize a variety of knotting techniques. Conventional knots, which are typically tied by the practitioner either within the body or outside the body and advanced over the suture length, may be utilized for locking the anchor in place relative to the tissue fold and opposing anchor; however, self-locking knots which enable the uni-directional travel of an anchor body relative to the suture and tissue are desirable. Accordingly, many different types of self-locking knots may be advanced with the anchor over the suture such that translation along a distal direction is possible yet reverse translation of the anchor is inhibited.

Various anchor cinching or locking mechanisms utilizing friction as a primary source for locking may also be implemented. For instance, locking pins may be urged or pushed into a frictional interference fit with portions or areas of the suture against the anchor or portions of the anchor. The use of such pins may effectively wedge the suture and thereby prevent further movement of the anchor along the suture length. In addition to pins, locking collars or collets may also be used to cinch or lock the suture.

In addition to friction-based locking and cinching mechanisms utilizable in tissue anchors, other mechanisms which create tortuous paths for the suture within or through the anchors may also be utilized for creating uni-directional locking. One cinching variation may utilize a pulley or pin contained within the anchor over which a portion of the suture may travel. The looped suture may then be routed proximally and secured with a slip knot. As tension is applied to the suture, the slip knot may prevent the further movement of the anchor relative to the suture.

Another variation on utilizing tortuous paths may comprise collars which are independent from or integrally formed with the anchors. Such cinching collars may generally be formed into tubular structures having obstructions formed within the collar lumen where the obstructions are formed from portions of the cinching collar itself. These obstructions may be adapted to form upon releasing of a constraining force when the anchor is to be locked into position. These obstructions may be used to form a tortuous path through which the suture may be routed to lock the suture within.

Moreover, locking collars which form tortuous paths may be adapted to reconfigure itself from a constrained delivery configuration to a deployed locking configuration when the anchor is to be cinched or locked into position relative to the tissue and suture. The locking collars may be configured to take various configurations, such as a proximally extending "S"-type, or other types, configuration.

Other cinching and locking mechanisms which utilize mechanical clamping or crimping to achieve locking of the suture within or through the anchors may also be used to facilitate uni-directional locking. For instance, a simple mechanical crimp may be fastened upon the suture proximally of the anchor to prevent the reverse motion of the anchor. The crimp may be a simple tubular member or it may be integrally formed onto a proximal portion of the anchor body itself.

Aside from the crimping mechanisms described above, additional measures may be optionally implemented to facilitate the cinching or locking of an anchor. Other measures may also be taken to inhibit any damage from occurring to the suture routed through an anchor. For instance, to ensure that the integrity of the suture is maintained in the presence of metallic basket anchors and to ensure that the suture is not subjected to any nicks or cuts, the portion of the suture passing through basket anchor may be encased in a protective sleeve made, e.g., from polypropylene, PTFE, etc.

Another measure which may optionally be implemented are cinching or locking mechanisms which take advantage of any cold-flow effects of an engaged portion of suture by the tissue anchor. For instance, if a portion of the suture is wedged against the collar of an anchor or cinching member to lock the anchor, the portion of the collar may have multiple holes defined over its surface to allow for portions of the engaged suture to cold-flow at least partially into or through the holes to enhance the locking effects.

Alternatively, the collar may be formed with an electrically conductive inner sleeve surrounded by an outer sleeve capable of flowing at least partially when heated. The inner sleeve may have a number of holes defined over its surface such that when the outer sleeve is heated, either by inductive heating or any other method, the outer sleeve material may flow through the holes and into contact with the suture passing therethrough. This contact may also enhance the locking effects of the collar.

BRIEF DESCRIPTION OF THE DRAWINGS

FIG. 1A shows a side view of one variation of a tissue plication apparatus which may be used to create tissue plications and to deliver cinching or locking anchors into the tissue.

Figure 1B:
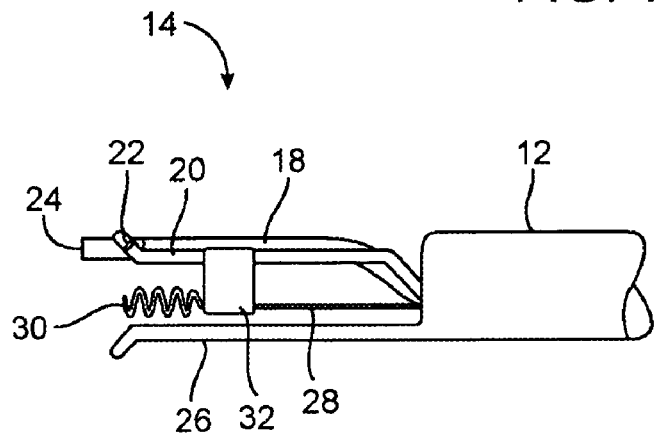
Figure 1C:
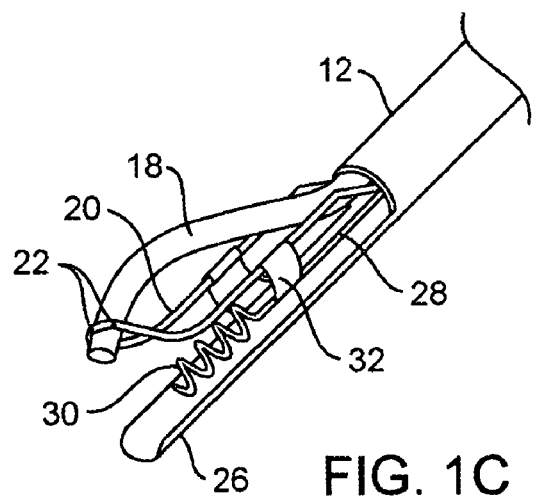

FIGS. 1B and 1C show detail side and perspective views, respectively, of the tissue manipulation assembly of the device of FIG. 1A.

FIGS. 2A to 2D show an example of a tissue plication procedure for the delivery and placement of tissue anchors.

FIGS. 3A to 3G show detail cross-sectional views of an anchor delivery assembly in proximity to a tissue plication and an example of delivering the tissue anchors on distal and proximal sides of the plication.

Figure 4A:
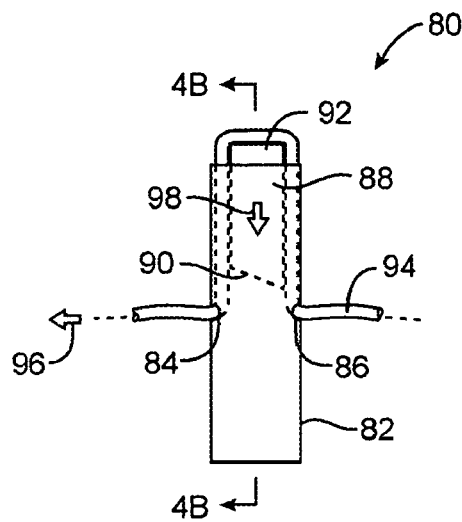
Figure 4B:
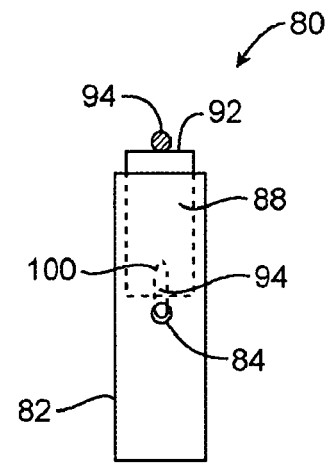

FIGS. 4A and 4B show side and end views, respectively, of one anchor variation which is illustrated in the form of a T-type anchor utilizing locking blocks or members for cinching and locking the suture.

Figure 5:
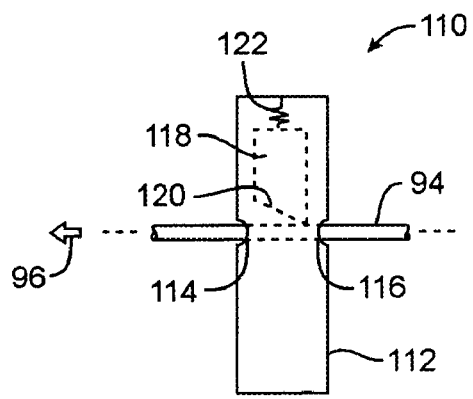

FIG. 5 shows a side view of another cinching anchor variation utilizing locking blocks or members.

Figure 6:
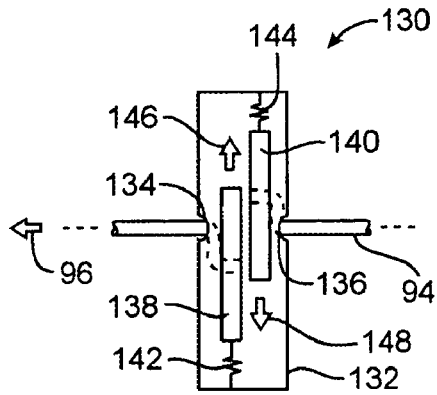

FIG. 6 shows yet another side view of a cinching anchor variation utilizing locking blocks or members.

Figure 7:
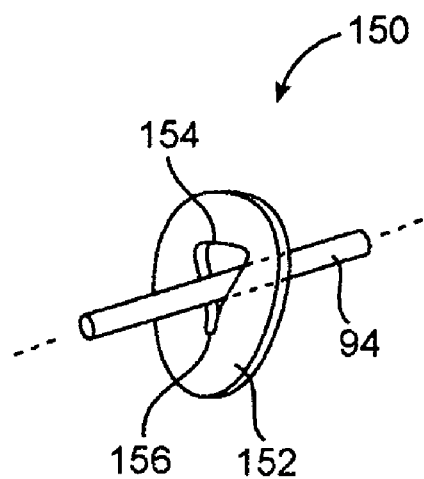

FIG. 7 shows a perspective view of another locking anchor variation in which the anchor body defines an opening having a tapered or grooved portion.

Figures 8A, 8B:
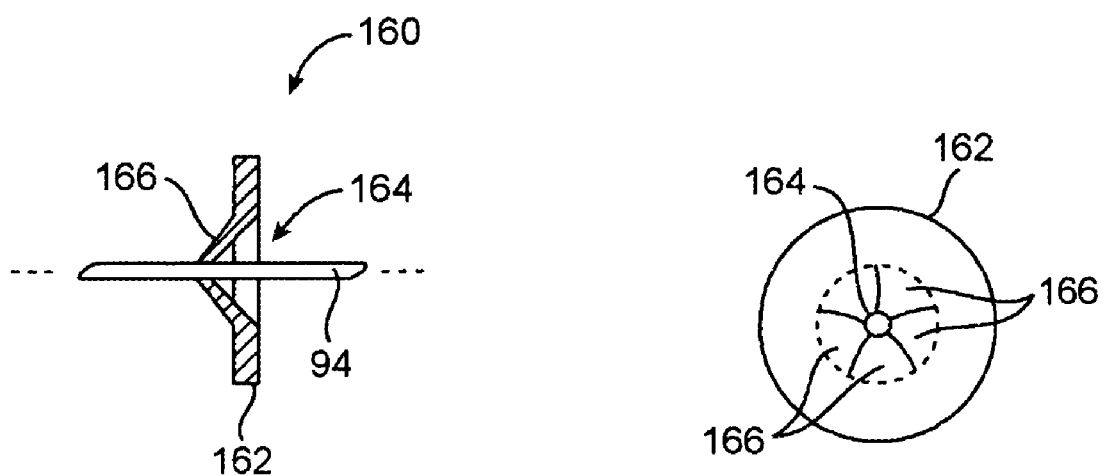

FIGS. 8A and 8B show cross-sectional side and top views, respectively, of another locking anchor variation utilizing a through-hole passage or opening and uni-directional levers or pivots through which the suture may pass.

Figure 8C:
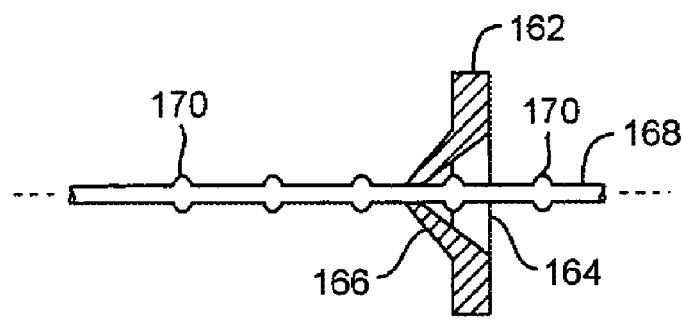

FIG. 8C shows a cross-sectional side view of an anchor body in combination with a modified suture having integrated features or protrusions defined along its length.

Figures 9A, 9B:
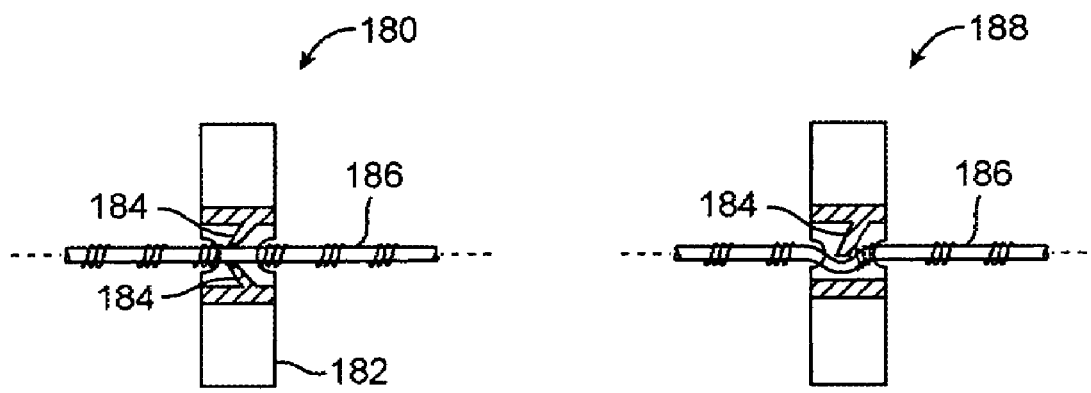

FIGS. 9A and 9B show cross-sectional views of locking anchor variations having biased locking members in combination with a knotted suture.

Figure 9C:
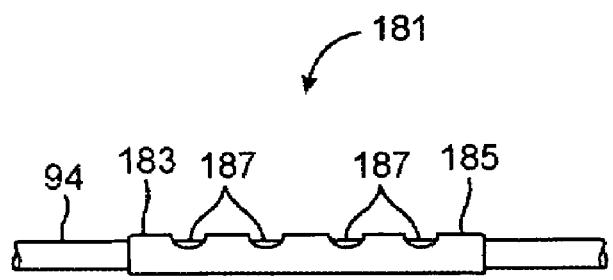

FIG. 9C shows another modification of the suture which may be coated with a metallic covering or slid within a sleeve.

Figure 10:
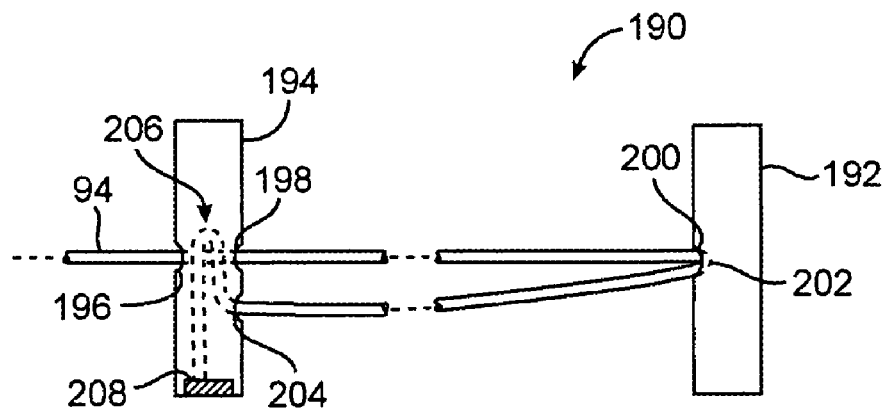

FIG. 10 shows a cross-sectional side view of an anchor assembly which utilizes a choke-type loop for cinching the anchors uni-directionally towards one another.

Figure 11A:
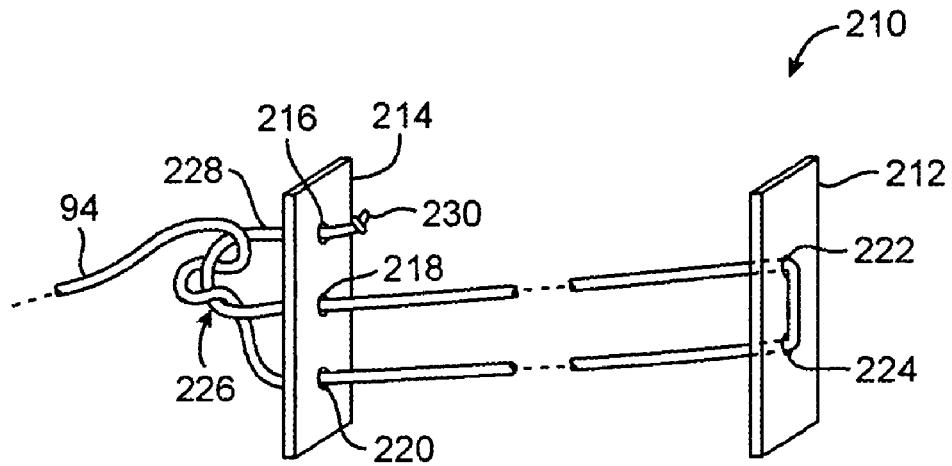

FIG. 11A shows a perspective view of another anchor assembly utilizing a slip knot at the proximal anchor.

Figure 11B:
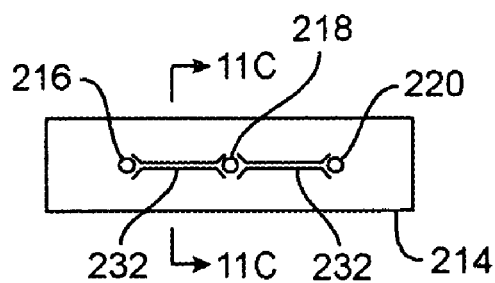
Figure 11C:
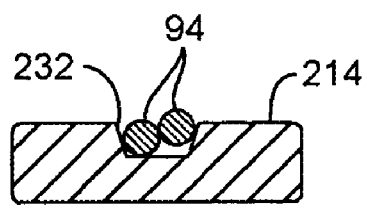

FIGS. 11B and 11C show top and cross-sectional side views, respectively, of an anchor which may optionally define grooves or channels extending at least partially therein to facilitate the cinching or wedging of the sutures within the grooves.

FIGS. 12A to 12G show examples of anchor assemblies utilizing various slip knots and looped sections which provide unidirectional travel for the anchors over the sutures.

Figure 13A:
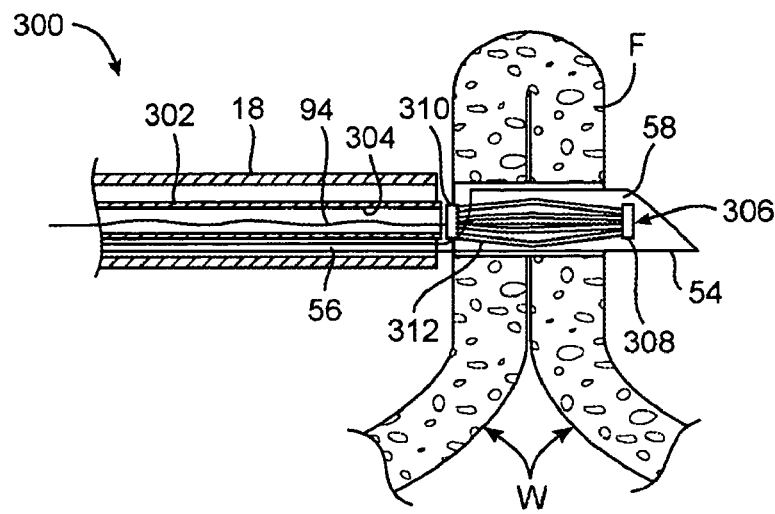

FIG. 13A shows a cross-sectional side view of an anchor delivery system delivering a basket-type anchor into or through a tissue plication.

Figure 13B:
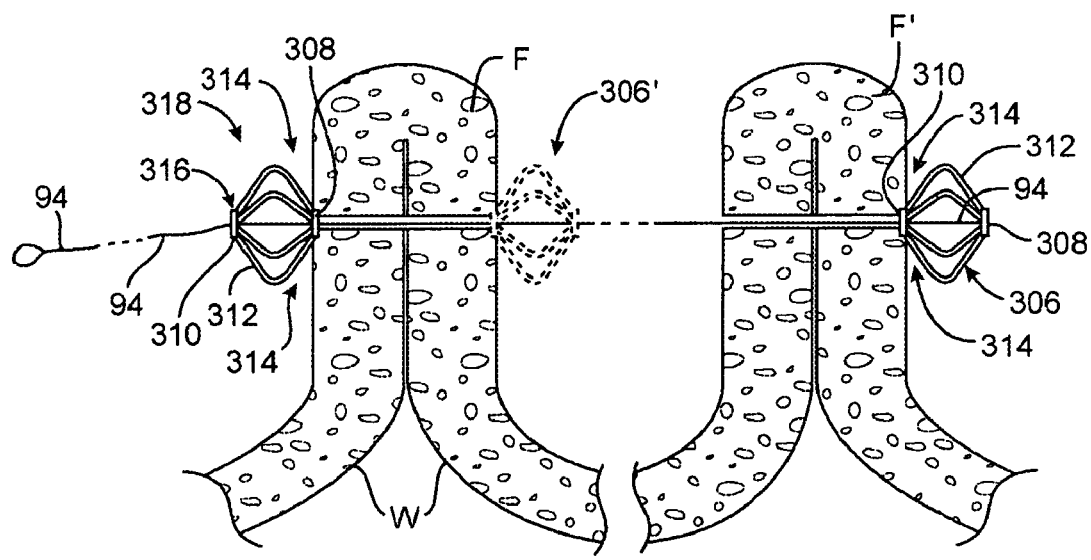

FIG. 13B shows a cross-sectional side view of multiple tissue plications which may be cinched towards one another and basket anchors as being deliverable through one or both tissue plications.

FIGS. 14A and 14B show cross-sectional side views of an anchor cinching assembly utilizing a cinching collar or collet which may be wedged into an anchor collar for clamping upon the suture.

FIGS. 15A and 15C show cross-sectional side views of another anchor cinching assembly utilizing a pin for wedging against a portion of the suture.

FIGS. 15B and 15D show end views of the assembly of FIGS. 15A and 15C, respectively.

Figure 15E:
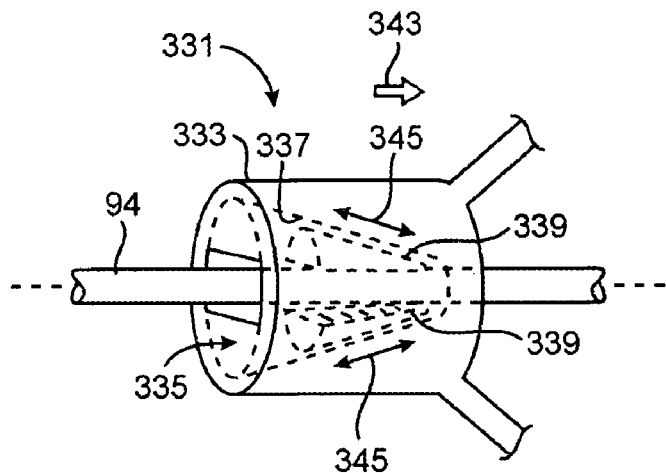

FIG. 15E shows a perspective view of another cinching variation utilizing one or more tapered pins or blocks slidably disposed within a tapered channel defined in a proximal collar of the anchor.

Figure 15F:
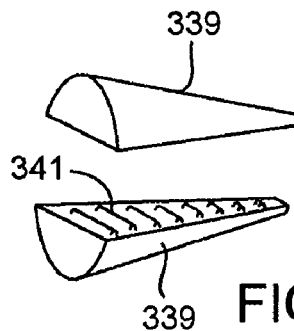

FIG. 15F shows a perspective view of the tapered pins from FIG. 15E.

Figure 15G:
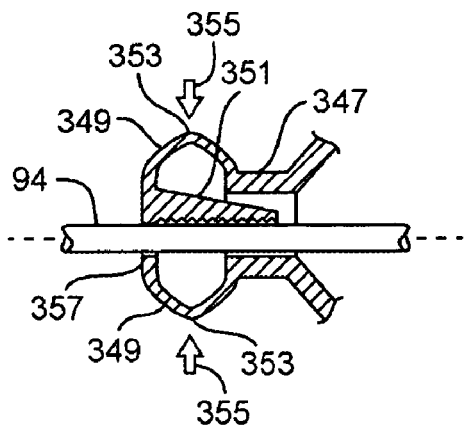
Figure 15H:
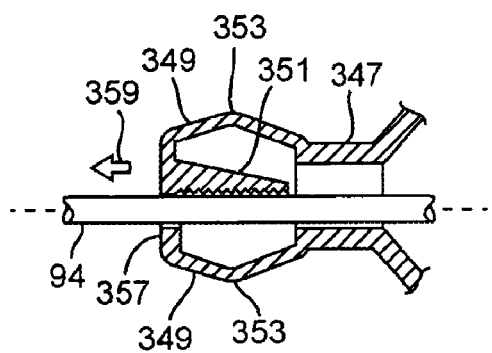

FIGS. 15G and 15H show cross-sectional side views of an alternative cinching assembly having a retractable pin in an engaged and disengaged configuration, respectively.

FIGS. 16A and 16B show cross-sectional side views of another variation of a cinching assembly having a rotatable cinching collar.

FIGS. 17A and 17B show cross-sectional side views of another cinching assembly having a retaining tube for providing a counterforce to stabilize the assembly during cinching or locking.

FIGS. 18A and 18B show cross-sectional side views of another cinching assembly having one or several biasing members or cinching tabs.

FIGS. 18C and 18D show end and perspective views, respectively, of a suture release member which may be used with the assembly of FIGS. 18A and 18B.

FIGS. 19A and 19B show cross-sectional side views of another variation of a cinching assembly utilizing a deformable cinching member positioned within the anchor and distally of the anchor collar.

FIG. 20A shows a cross-sectional side view of another cinching assembly utilizing a pivoting cinching member configured to lock against the suture.

FIGS. 20B, 20C, and 20D show end and cross-sectional side views, respectively, of the pivoting member positioned within the anchor collar.

Figure 20E:
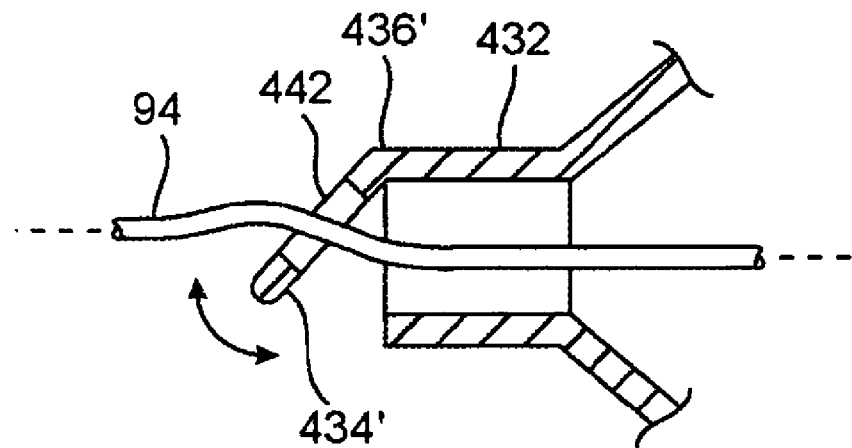
Figure 20F:
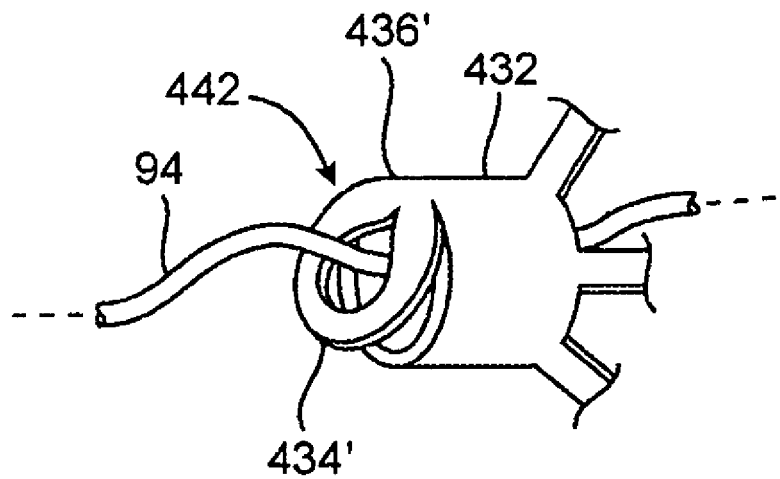

FIGS. 20E and 20F show cross-sectional side and perspective views, respectively, of another cinching assembly having a pivoting cinching member positioned proximally of the anchor collar.

FIGS. 21A and 21B show cross-sectional side views of another cinching assembly configured to cinch or lock the suture with a tapered collar.

FIG. 22A shows a cross-sectional side view of another cinching assembly utilizing a looped suture and a slip knot for cinching the anchor over the suture.

Figure 22B:
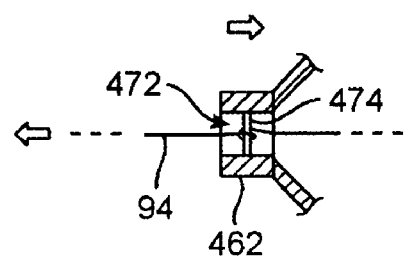
Figure 22C:
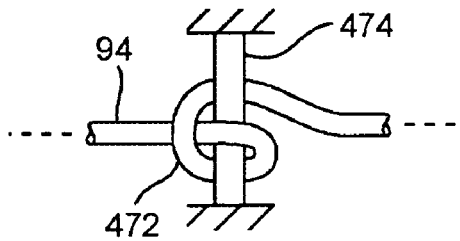
Figure 22D:
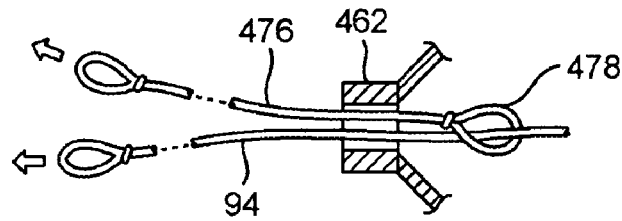
Figure 22E:
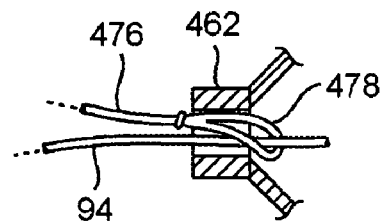

FIGS. 22B and 22C show cross-sectional side and detail views, respectively, of another cinching assembly which may be utilized with a portion of suture wrapped or looped about a pin which enables uni-directional travel of the anchor relative to the suture FIGS. 22D and 22E show cross-sectional side and detail views, respectively, of another cinching assembly utilizing looped suture wedged within the anchor collar.

Figure 23:
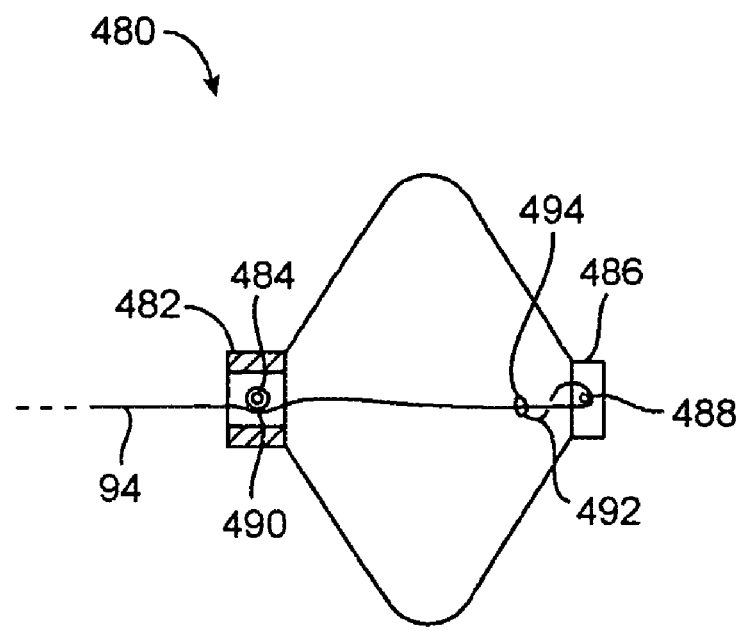

FIG. 23 shows a cross-sectional side view of a cinching assembly variation utilizing a number of pulleys to create the cinching effect.

Figure 24A:
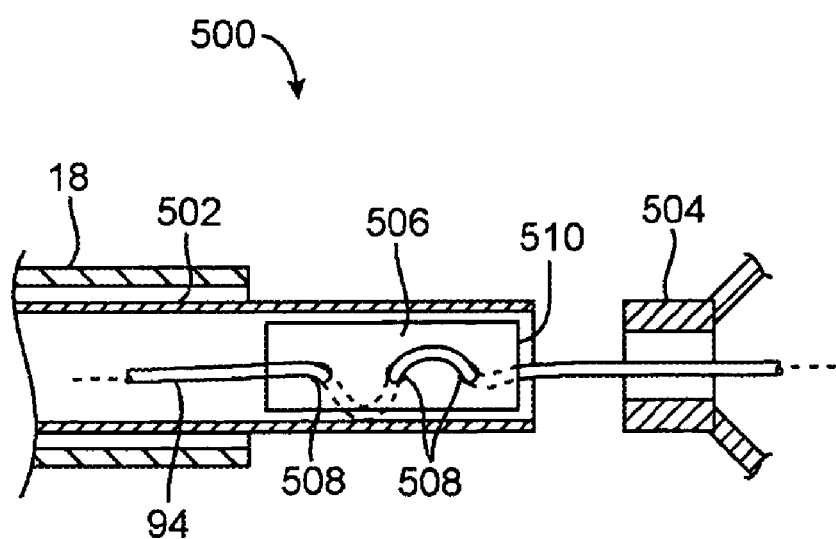

FIG. 24A shows a cross-sectional side view of another cinching assembly variation in which a cinching sleeve may be used to create a tortuous path for the suture.

Figure 24B:
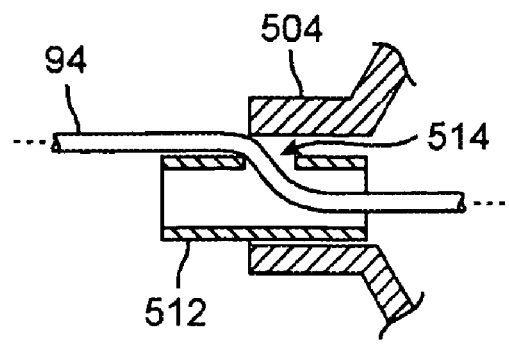
Figure 24C:
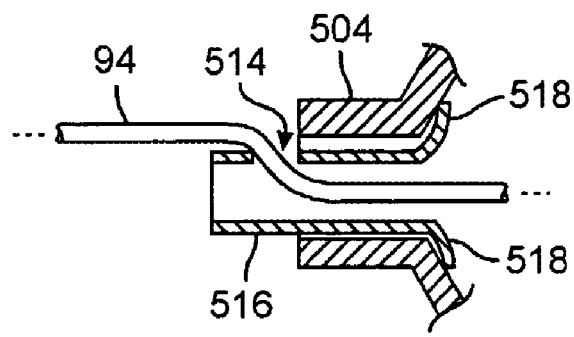

FIGS. 24B and 24C show cross-sectional side views of another cinching assembly variation having a tubular structure, with and without retaining arms, respectively, positioned within the anchor collar through which the suture may pass uni-directionally.

Figure 24D:
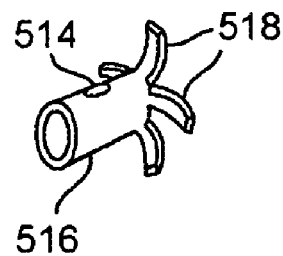

FIG. 24D shows a perspective view of one variation of the tubular structure of FIG. 24C with retaining arms.

Figure 25A:
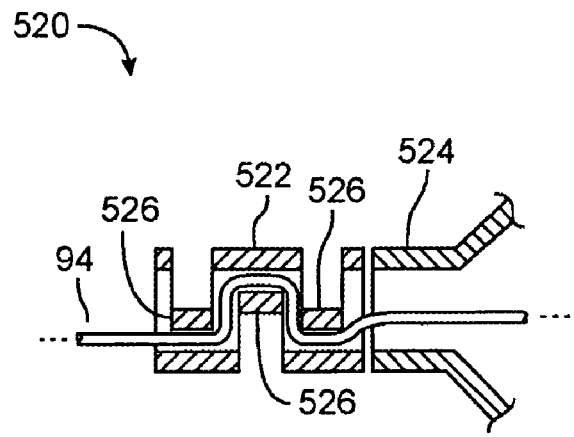
Figure 25B:
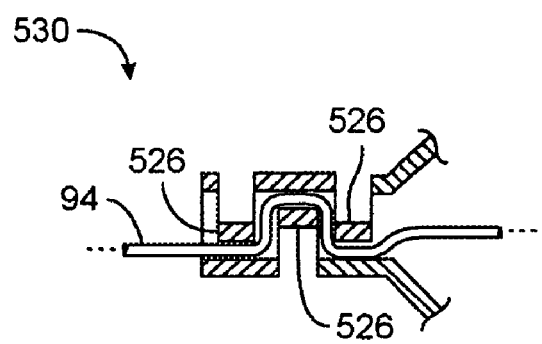

FIGS. 25A and 25B show cross-sectional side views of another cinching assembly variation in which a cinching collar, which may be independent of the anchor or formed integrally with the anchor, respectively, may have a tortuous path formed within the collar.

Figure 25C:
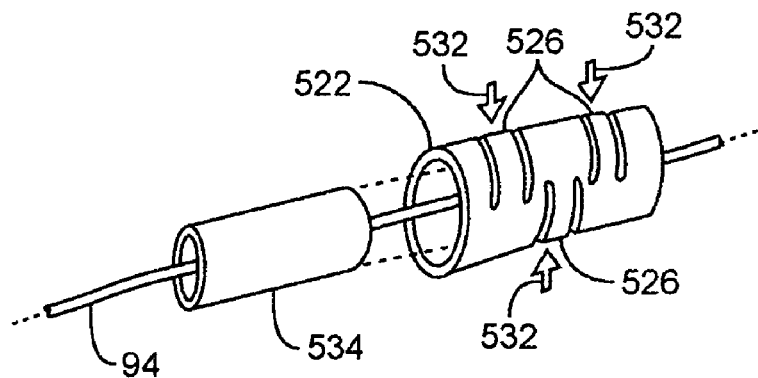

FIG. 25C shows a perspective view of the collar of FIG. 25A in its unobstructed configuration with a constraining sleeve which may be positioned within the collar.

Figure 26A:
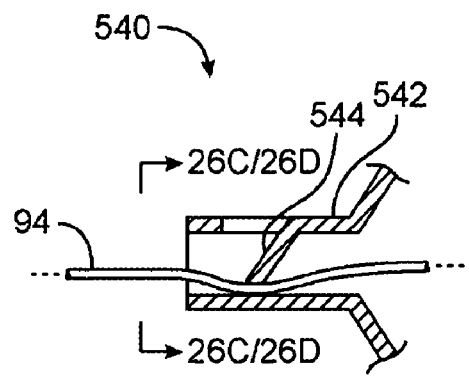
Figure 26B:
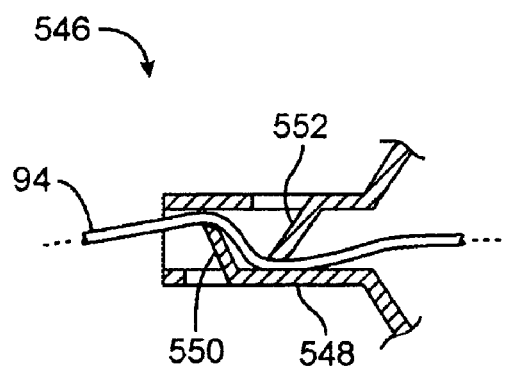

FIGS. 26A and 26B show cross-sectional side views of another cinching assembly variation utilizing one or several pivoting levers which allow uni-directional travel of the suture therethrough.

Figures 26C, 26D:
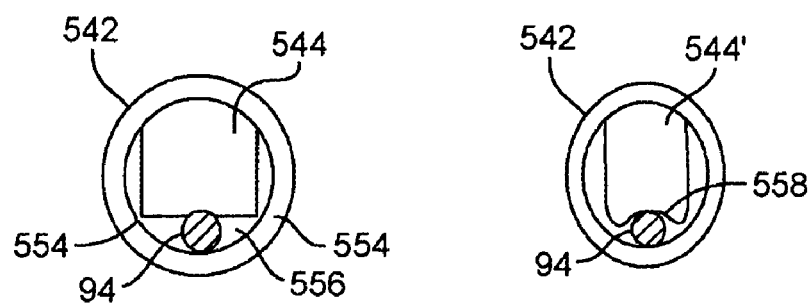

FIGS. 26C and 26D show alternative end views of the assembly of FIG. 26A in which the lever may be configured to prevent over cinching onto the suture.

Figure 26E:
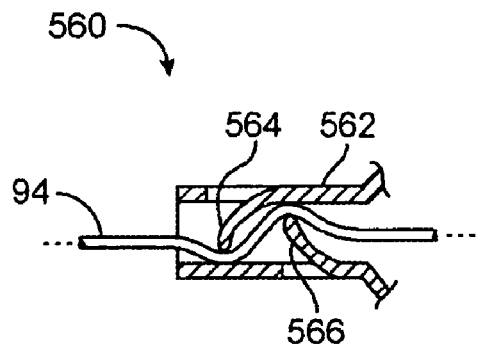
Figure 26F:
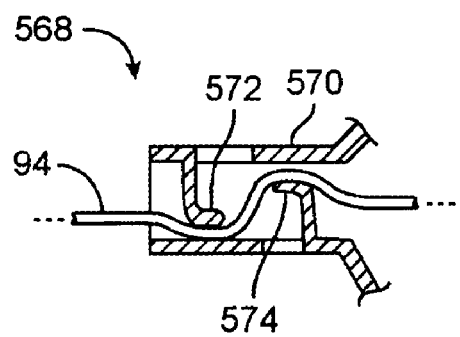
Figure 26G:
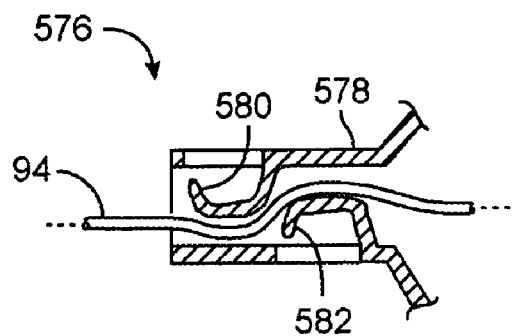

FIGS. 26E to 26G show cross-sectional side views of alternative cinching assemblies in which the levers may be variously configured to create the tortuous path.

Figure 27A:
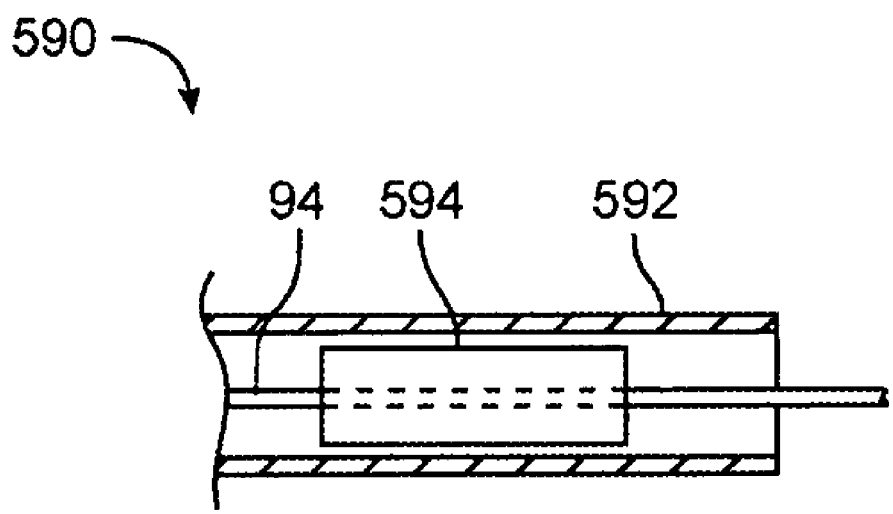
Figure 27B:
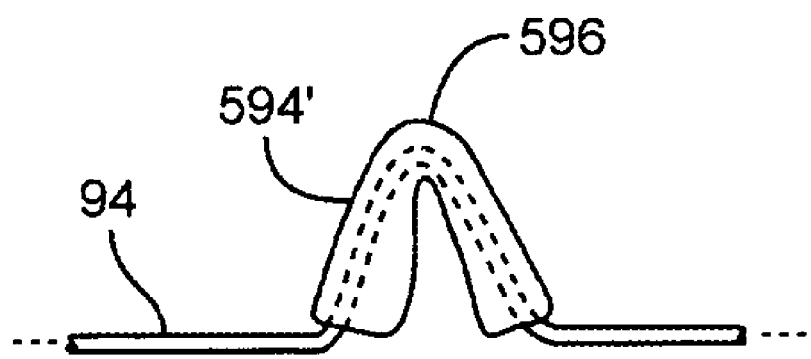

FIGS. 27A and 27B show side views of another cinching assembly variation in a delivery profile and a reconfigured profile, respectively, which utilizes a crimp which may be self-forming.

Figure 28A:
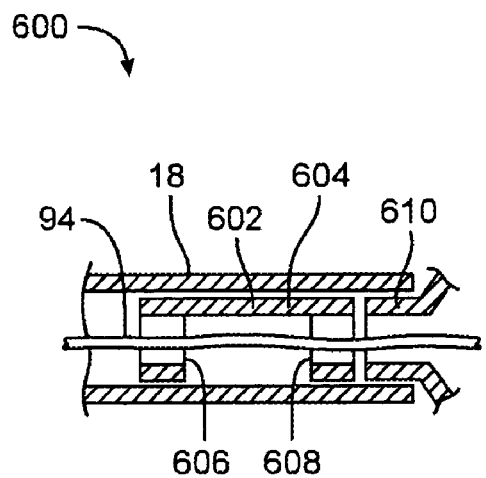
Figure 28B:
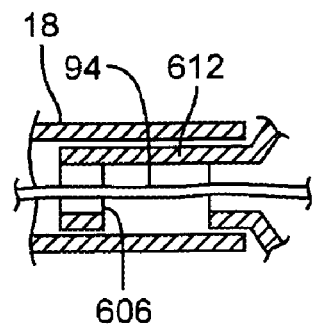

FIGS. 28A and 28B show cross-sectional side views of another cinching assembly variation utilizing either two cinching collars or a single integral cinching collar, respectively.

Figure 28C:
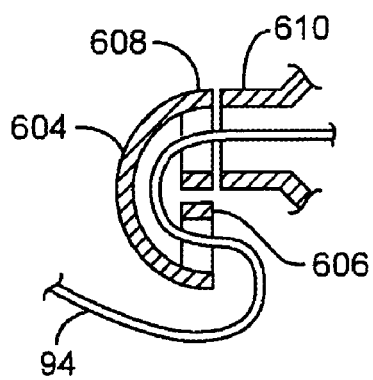

FIG. 28C shows a cross-sectional side view of the cinching collar of FIG. 28A in one configuration for cinching the suture.

Figure 28D:
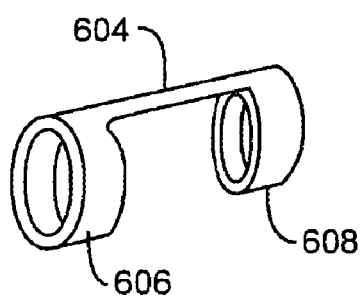
Figure 28E:
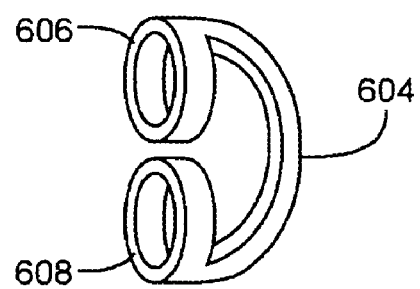

FIGS. 28D and 28E show perspective views of the cinching collar of FIG. 28A in a delivery profile and a reconfigured profile.

Figure 28F:
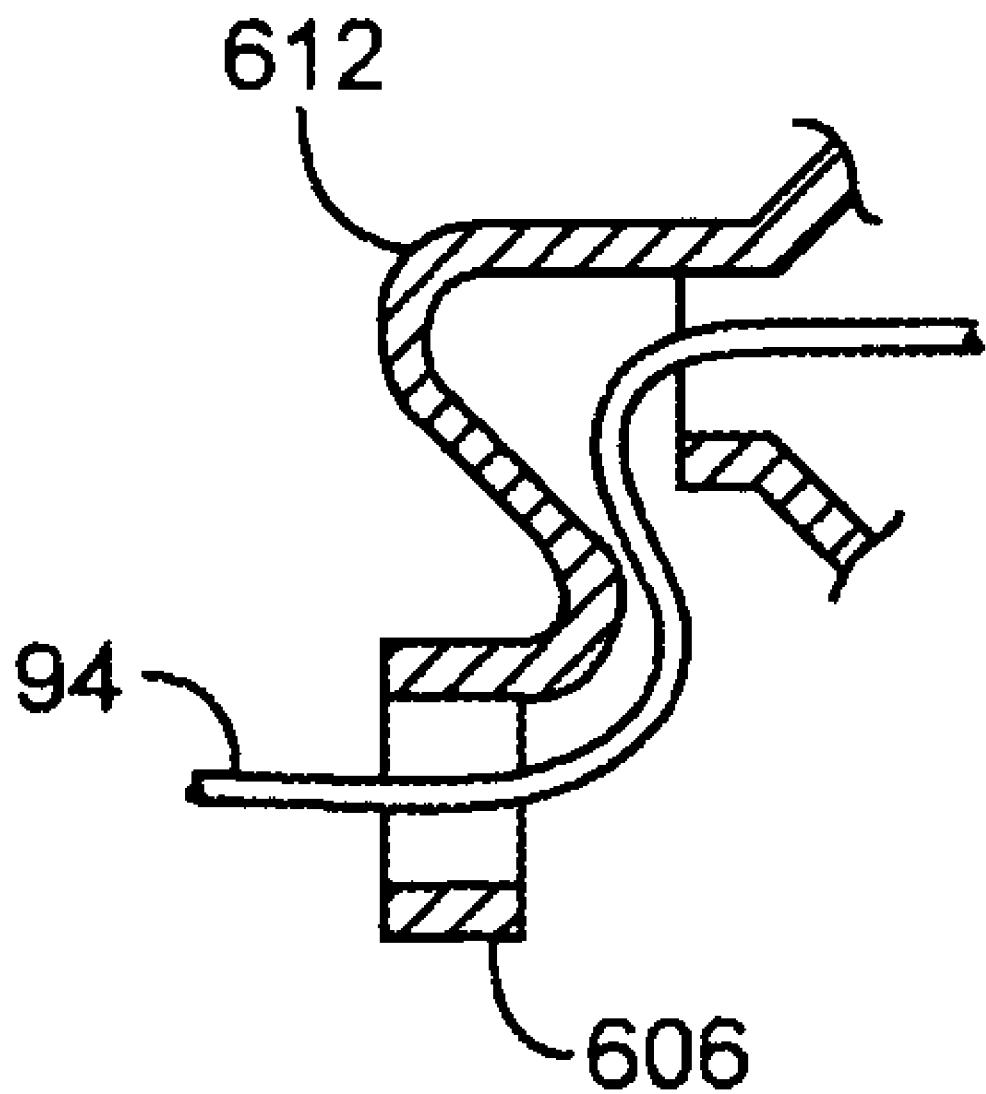

FIG. 28F shows a cross-sectional side view of another variation for a cinching configuration of the cinching collar of FIG. 28B.

Figure 28G:
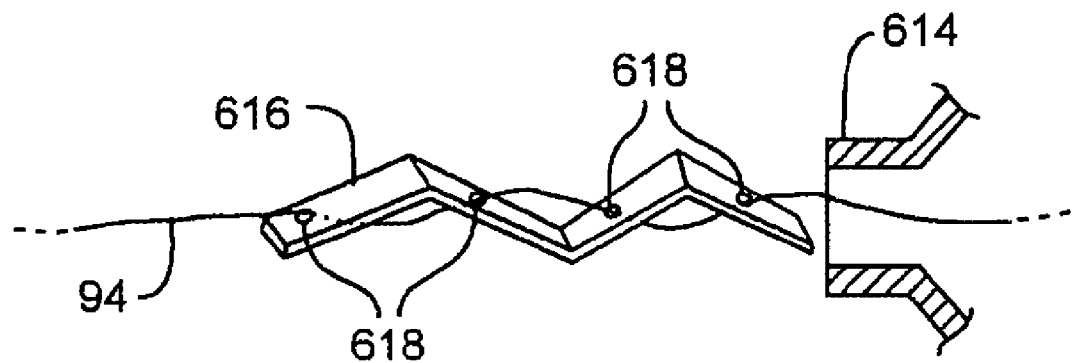
Figure 28H:
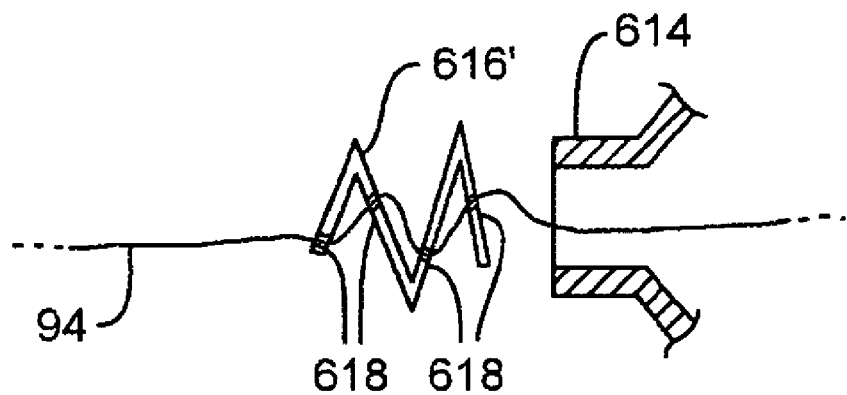

FIGS. 28G and 28H show cross-sectional side views of another cinching assembly variation in a delivery profile and reconfigured profile, respectively, in which an elongate cinching member may reconfigure itself to create a tortuous path for the suture.

FIGS. 29A and 29B show cross-sectional side views of another cinching assembly variation utilizing a mechanical crimp.

FIGS. 30A and 30B show cross-sectional side views of another cinching assembly variation in which a mechanical crimp may be utilized on the proximal collar of the anchor body.

Figure 31A:
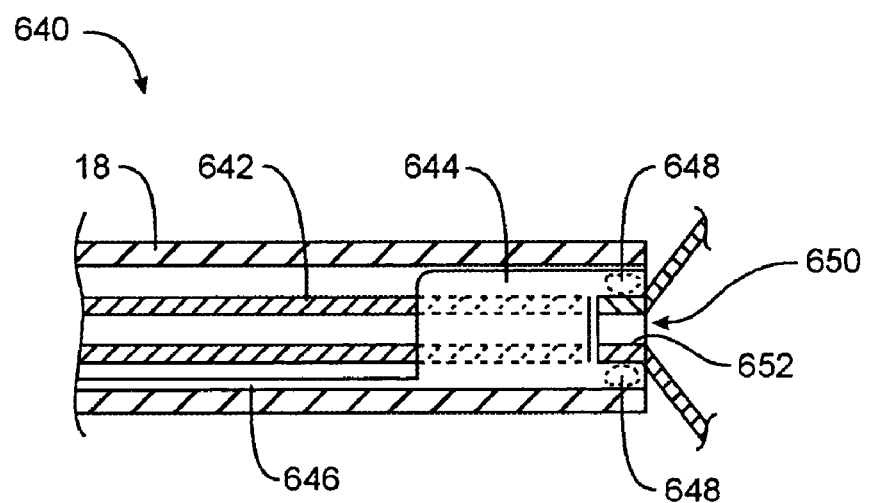

FIG. 31A shows a cross-sectional side view of a variation of a tool assembly which may be adapted to apply a mechanical crimping force upon a crimping collar.

Figure 31B:
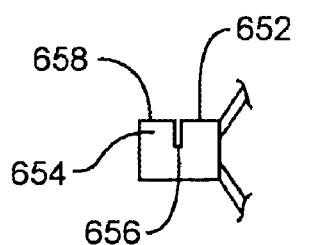
Figure 31C:
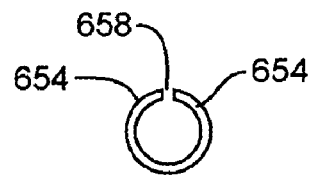
Figure 31D:
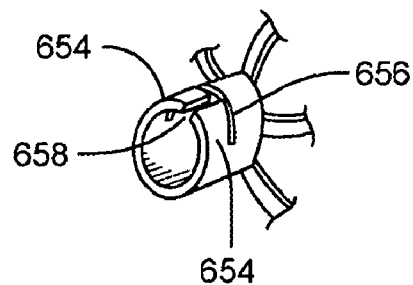

FIGS. 31B to 31D show side, end, and perspective views, respectively, of a variation on a crimping collar which may be utilized as a separate crimping sleeve or as part of the anchor collar.

Figure 32A:
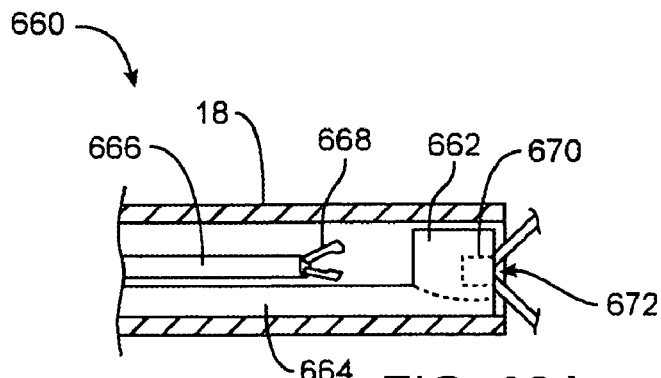
Figure 32B:
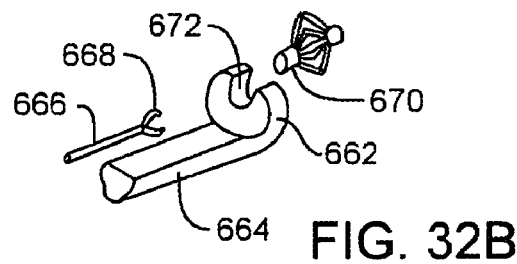

FIGS. 32A and 32B show cross-sectional side and perspective views, respectively, of an alternative crimping tool.

Figure 33A:
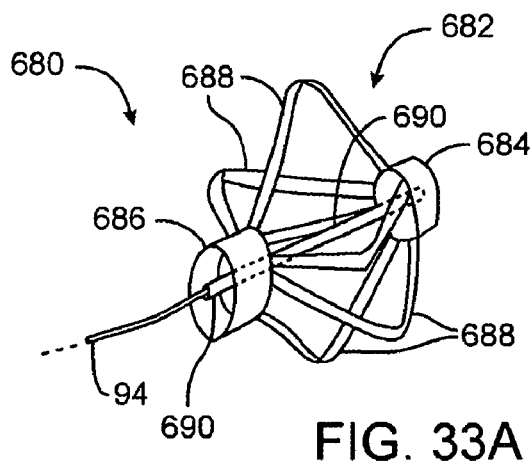
Figure 33B:
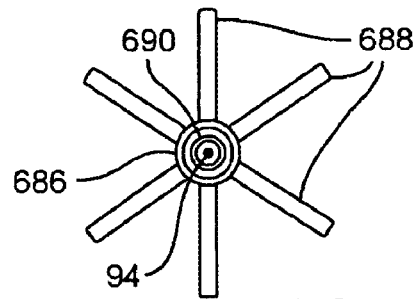

FIGS. 33A and 33B show perspective and end views, respectively, of a representative basket anchor having a protective sleeve encasing the suture disposed within the anchor.

Figure 34A:
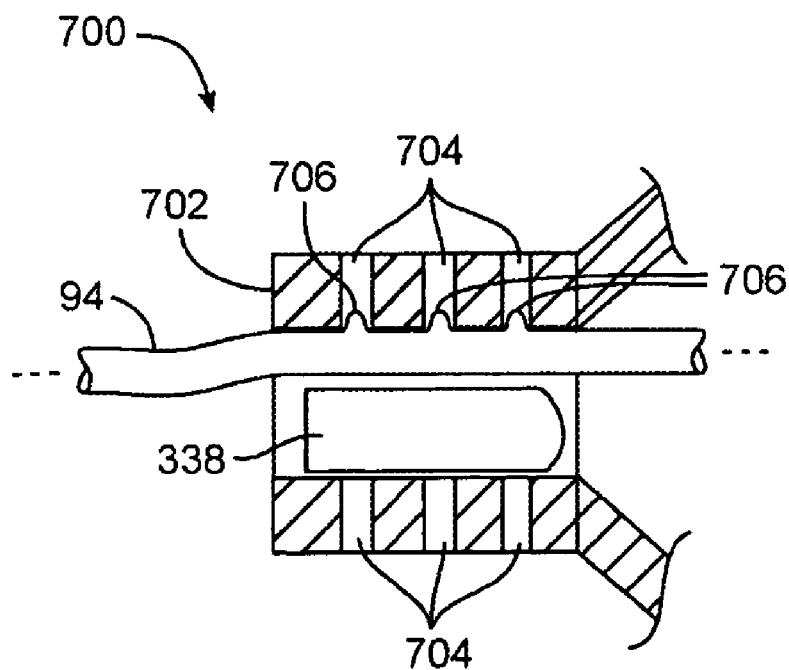
Figure 34B:
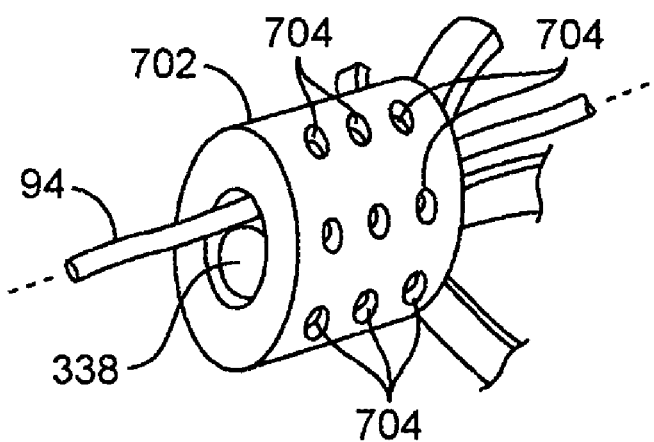

FIGS. 34A and 34B show cross-sectional side and perspective views, respectively, of a cinching collar defining a plurality of holes through the surface of the collar for enhancing the locking effects with the suture.

FIG. 35A shows a cross-sectional side view of a cinching assembly variation which may utilize inductive heating to partially melt a portion of an outer sleeve into contact with the suture to enhance the anchor locking effects.

FIGS. 35B and 35C show perspective assembly and exploded views, respectively, of an electrically conductive inner sleeve contained within the outer sleeve.

FIGS. 35D and 35E show perspective views of alternative inner sleeves which may be utilized with the assembly of FIG. 35A.

DETAILED DESCRIPTION OF THE INVENTION

In order to first create the plication within a body lumen of a patient, various methods and devices may be implemented. The anchoring and securement devices may be delivered and positioned via an endoscopic apparatus that engages a tissue wall of the gastrointestinal lumen, creates one or more tissue folds, and disposes one or more of the anchors through the tissue fold(s). The tissue anchor(s) may be disposed through the muscularis and/or serosa layers of the gastrointestinal lumen.

Generally, in creating a plication through which a tissue anchor may be disposed within or through, a distal tip of a tissue plication apparatus may engage or grasp the tissue and move the engaged tissue to a proximal position relative to the tip of the device, thereby providing a substantially uniform plication of predetermined size.

Formation of a tissue fold may be accomplished using at least two tissue contact areas that are separated by a linear or curvilinear distance, wherein the separation distance between the tissue contact points affects the length and/or depth of the fold. In operation, a tissue grabbing assembly engages or grasps the tissue wall in its normal state (i.e., non-folded and substantially flat), thus providing a first tissue contact area. The first tissue contact area then is moved to a position proximal of a second tissue contact area to form the tissue fold. The tissue anchor assembly then may be extended across the tissue fold at the second tissue contact area. Optionally, a third tissue contact point may be established such that, upon formation of the tissue fold, the second and third tissue contact areas are disposed on opposing sides of the tissue fold, thereby providing backside stabilization during extension of the anchor assembly across the tissue fold from the second tissue contact area.

The first tissue contact area may be utilized to engage and then stretch or rotate the tissue wall over the second tissue contact area to form the tissue fold. The tissue fold may then be articulated to a position where a portion of the tissue fold overlies the second tissue contact area at an orientation that is substantially normal to the tissue fold. A tissue anchor may then be delivered across the tissue fold at or near the second tissue contact area. An apparatus in particular which is particularly suited to deliver the anchoring and securement devices described herein may be seen in further detail in co-pending U.S. patent application Ser. No. 10/735,030 filed Dec. 12, 2003 and entitled "Apparatus And Methods For Forming And Securing Gastrointestinal Tissue Folds", which is incorporated herein by reference in its entirety.

An illustrative side view of a tissue plication assembly 10 which may be utilized with the tissue anchors described herein is shown in FIG. 1A. The plication assembly 10 generally comprises a catheter or tubular body 12 which may be configured to be sufficiently flexible for advancement into a body lumen, e.g., transorally, percutaneously, laparoscopically, etc. Tubular body 12 may be configured to be torqueable through various methods, e.g., utilizing a braided tubular construction, such that when handle 16 is manipulated and rotated by a practitioner from outside the body, the torquing force is transmitted along body 12 such that the distal end of body 12 is rotated in a corresponding manner.

Tissue manipulation assembly 14 is located at the distal end of tubular body 12 and is generally used to contact and form the tissue plication, as mentioned above. FIG. 1B shows an illustrative detail side view of tissue manipulation assembly 14 which shows launch tube 18 extending from the distal end of body 12 and in-between the arms of upper extension member or bail 20. Launch tube 18 may define launch tube opening 24 and may be pivotally connected near or at its distal end via hinge or pivot 22 to the distal end of upper bail 20. Lower extension member or bail 26 may similarly extend from the distal end of body 12 in a longitudinal direction substantially parallel to upper bail 20. Upper bail 20 and lower bail 26 need not be completely parallel so long as an open space between upper bail 20 and lower bail 26 is sufficiently large enough to accommodate the drawing of several layers of tissue between the two members.

Upper bail 20 is shown in the figure as an open looped member and lower bail 26 is shown as a solid member; however, this is intended to be merely illustrative and either or both members may be configured as looped or solid members. Tissue acquisition member 28 may be an elongate member, e.g., a wire, hypotube, etc., which terminates at a tissue grasper 30, in this example a helically-shaped member, configured to be reversibly rotatable for advancement into the tissue for the purpose of grasping or acquiring a region of tissue to be formed into a plication. Tissue acquisition member 28 may extend distally from handle 16 through body 12 and distally between upper bail 20 and lower bail 26. Acquisition member 28 may also be translatable and rotatable within body 12 such that tissue grasper 30 is able to translate longitudinally between upper bail 20 and lower bail 26. To support the longitudinal and rotational movement of acquisition member 28, an optional guide or sled 32 may be connected to upper 20 or lower bail 26 to freely slide thereon. Guide 32 may also be slidably connected to acquisition member 28 such that the longitudinal motion of acquisition member 28 is supported by guide 32.

Figure 2A:
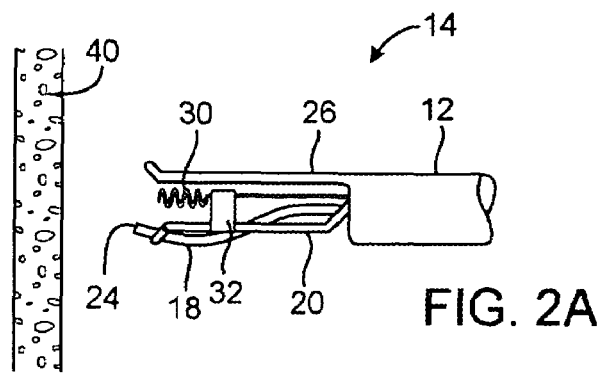

An example of a tissue plication procedure is seen in FIGS. 2A to 2D for delivering and placing a tissue anchor and is disclosed in further detail in co-pending U.S. patent application Ser. No. 10/735,030 filed Dec. 12, 2003, which has been incorporated by reference above. Tissue manipulation assembly 14, as seen in FIG. 2A, may be advanced into a body lumen such as the stomach and positioned adjacent to a region of tissue wall 40 to be plicated. During advancement, launch tube 18 may be configured in a delivery profile such that tube 18 is disposed within or between the arms of upper bail 20 to present a relatively small profile.

Figure 2B:
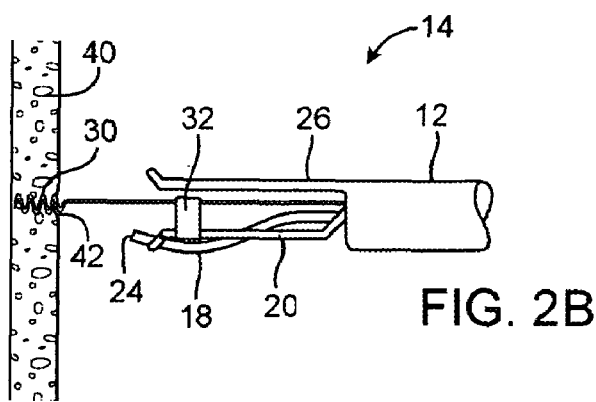

Once tissue manipulation assembly 14 has been desirably positioned relative to tissue wall 40, tissue acquisition member 30 may be advanced distally such that tissue acquisition member 30 comes into contact with tissue wall 40 at acquisition location or point 42. As acquisition member 30 is distally advanced relative to body 12, guide 32, if utilized, may slide distally along with member 30 to aid in stabilizing the grasper. If a helically-shaped acquisition member 30 is utilized, as illustrated in FIG. 2B, it may be rotated from its proximal end at handle 16 and advanced distally until the tissue at point 42 has been firmly engaged by acquisition member 30. This may require advancement of acquisition member 30 through the mucosal layer and at least into or through the underlying muscularis layer and preferably into or through the serosa layer.

Figure 2C:
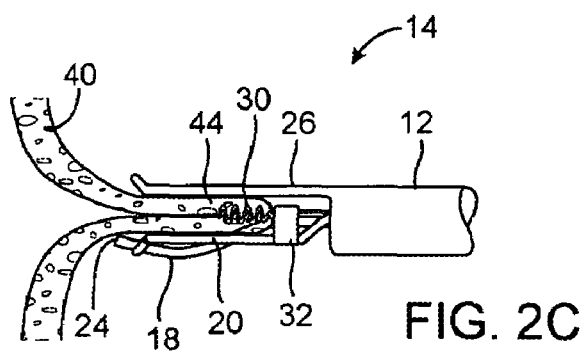

The grasped tissue may then be pulled proximally between upper 20 and lower bails 26 via acquisition member 30 such that the acquired tissue is drawn into a tissue fold 44, as seen in FIG. 2C. As acquisition member 30 is withdrawn proximally relative to body 12, guide 32 may also slide proximally to aid in stabilizing the device especially when drawing the tissue fold 44.

Once the tissue fold 44 has been formed, launch tube 18 may be advanced from its proximal end at handle 16 such that a portion 46 of launch tube 18, which extends distally from body 12, is forced to rotate at hinge or pivot 22 and reconfigure itself such portion 46 forms a curved or arcuate shape that positions launch tube opening 24 perpendicularly relative to a longitudinal axis of body 12 and/or bail members 20, 26. Launch tube 18, or at least portion 46 of launch tube 18, is preferably fabricated from a highly flexible material or it may be fabricated, e.g., from Nitinol tubing material which is adapted to flex, e.g., via circumferential slots, to permit bending. Alternatively, assembly 14 may be configured such that launch tube 18 is reconfigured simultaneously with the proximal withdrawal of acquisition member 30 and acquired tissue 44.

As discussed above, the tissue wall of a body lumen, such as the stomach, typically comprises an inner mucosal layer, connective tissue, the muscularis layer and the serosa layer. To obtain a durable purchase, e.g., in performing a stomach reduction procedure, the staples or anchors used to achieve reduction of the body lumen are preferably engaged at least through or at the muscularis tissue layer, and more preferably, the serosa layer. Advantageously, stretching of tissue fold 44 between bail members 20, 26 permits an anchor to be ejected through both the muscularis and serosa layers, thus enabling durable gastrointestinal tissue approximation.

Figure 2D:
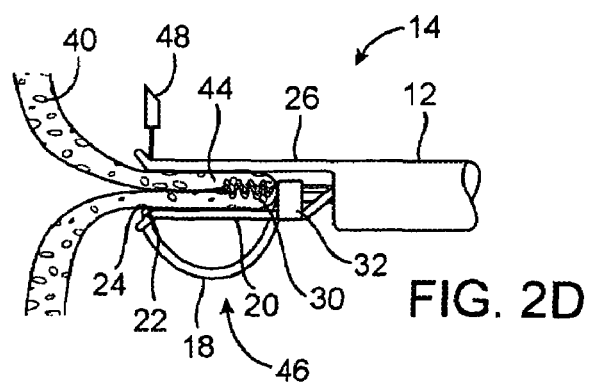

As shown in FIG. 2D, once launch tube opening 24 has been desirably positioned relative to the tissue fold 44, needle assembly 48 may be advanced through launch tube 18 via manipulation from its proximal end at handle 16 to pierce preferably through a dual serosa layer through tissue fold 44. Needle assembly 48 is preferably a hollow tubular needle through which one or several tissue anchors may be delivered through and ejected from in securing the tissue fold 44, as further described below.

Figure 3A:
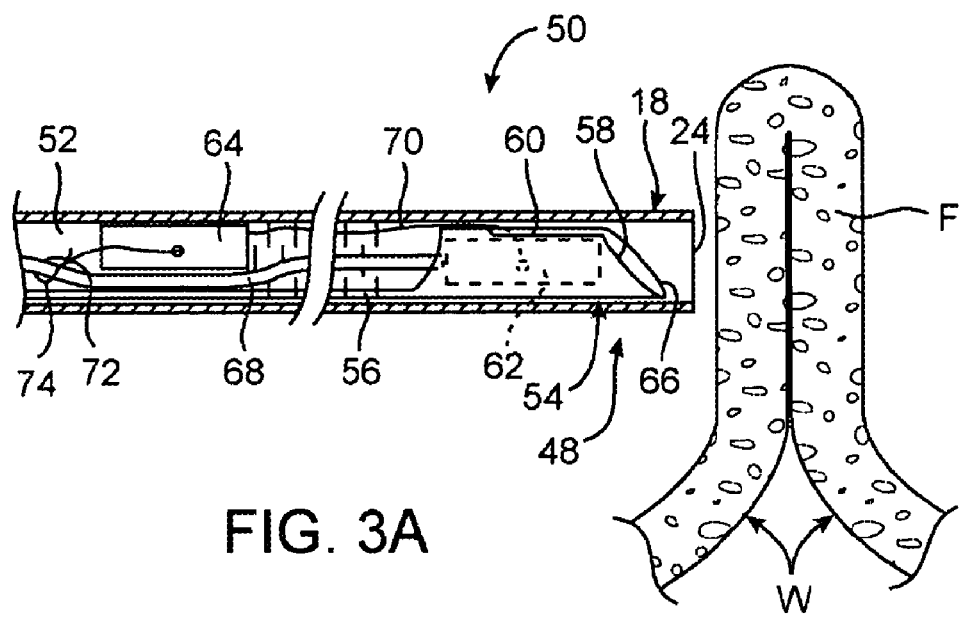

Because needle assembly 48 penetrates the tissue wall twice, it exits within the body lumen, thus reducing the potential for injury to surrounding organs. A detail cross-sectional view is shown in FIG. 3A of anchor delivery assembly 50 in proximity to tissue fold F. In this example, tissue fold F may comprise a plication of tissue created using the apparatus 10 described herein or any other tool configured to create such a tissue plication. Tissue fold F may be disposed within a gastrointestinal lumen, such as the stomach, where tissue wall W may define the outer or serosal layer of the stomach. Anchor delivery assembly may generally comprise launch tube 18 and needle assembly 48 slidingly disposed within launch tube lumen 52. Needle assembly 48 is generally comprised of needle 54, which is preferably a hollow needle having a tapered or sharpened distal end 66 to facilitate its travel into and/or through the tissue. Other parts of the assembly, such as upper and lower bail members 20, 26, respectively, and tissue acquisition member 28 have been omitted from these figures only for clarity.

Once launch tube 18 has been desirably positioned with respect to tissue fold F, needle 54 may be urged or pushed into or through tissue fold F via needle pushrod or member 56 from its proximal end preferably located within handle 16. Needle 54 may define needle lumen 58 within which distal anchor 62 and/or proximal anchor 64 may be situated during deployment and positioning of the assembly. A single suture or flexible element 70 (or multiple suture elements) may connect proximal anchor 64 and distal anchor 62 to one another. For instance, element 70 may comprise various materials such as monofilament, multifilament, or any other conventional suture material, elastic or elastomeric materials, e.g., rubber, etc.

Alternatively, metals which are biocompatible may also be utilized for suture materials. For instance, sutures may be made from metals such as Nitinol, stainless steels, Titanium, etc., provided that they are formed suitably thin and flexible. Using metallic sutures with the anchoring mechanisms described herein may additionally provide several benefits. For example, use of metallic suture material may decrease any possibilities of suture failure due to inadvertent cutting or shearing of the suture, it may provide a suture better able to withstand the acidic and basic environment of the gastrointestinal system, and it may also enhance imaging of the suture and anchor assembly if examined under conventional imaging systems such as X-rays, fluoroscopes, MRI, etc. As used herein, suture 70 may encompass any of these materials or any other suitable material which is also biocompatible.

Needle 54 may optionally define needle slot 60 along its length to allow suture 70 to pass freely within and out of needle 54 when distal anchor 62 is ejected from needle lumen 58. Alternatively, rather than utilizing needle slot 60, needle 54 may define a solid structure with suture 70 being passed into needle lumen 58 via the distal opening of needle 54.

The proximal end of suture 70 may pass slidingly through proximal anchor 64 to terminate in suture loop 74 via cinching knot 72. Suture loop 74 may be omitted and the proximal end of suture 70 may terminate proximally of the apparatus 10 within control handle 16, proximally of control handle 16, or at some point distally of control handle 16. In this variation, suture loop 74 may be provided to allow for a grasping or hooking tool to temporarily hold suture loop 74 for facilitating the cinching of proximal 64 and distal 62 anchors towards one another for retaining a configuration of tissue fold F, as described in further detail below. Cinching knot 72 may also comprise a slidable knot which may be slid distally along suture 70 to lock or hold against proximal anchor 64 once the tissue fold F and anchors 62, 64 have been desirably positioned and tensioned, as also described below in further detail.

Figure 3B:
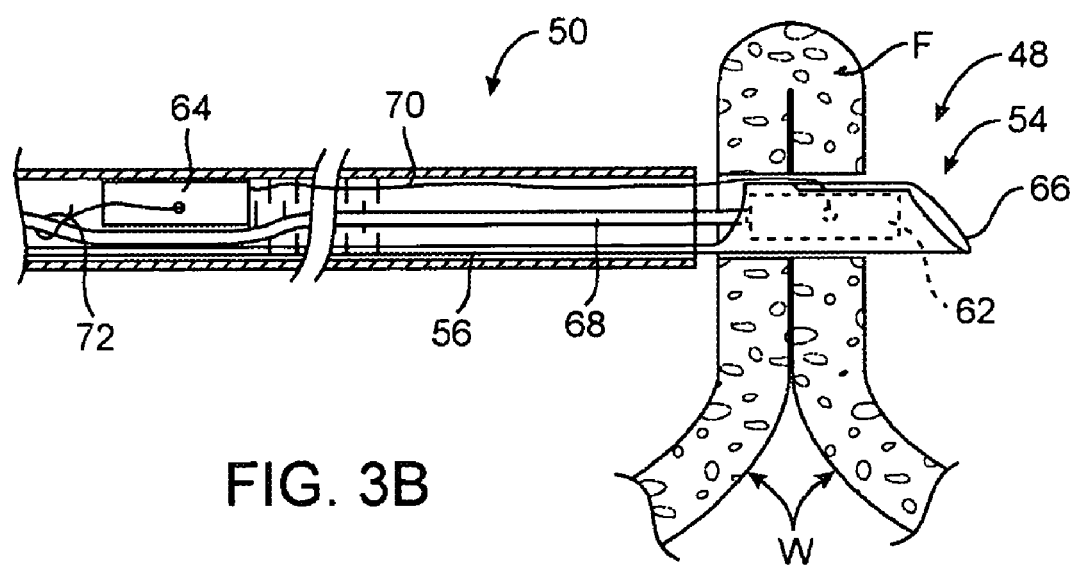
Figure 3C:
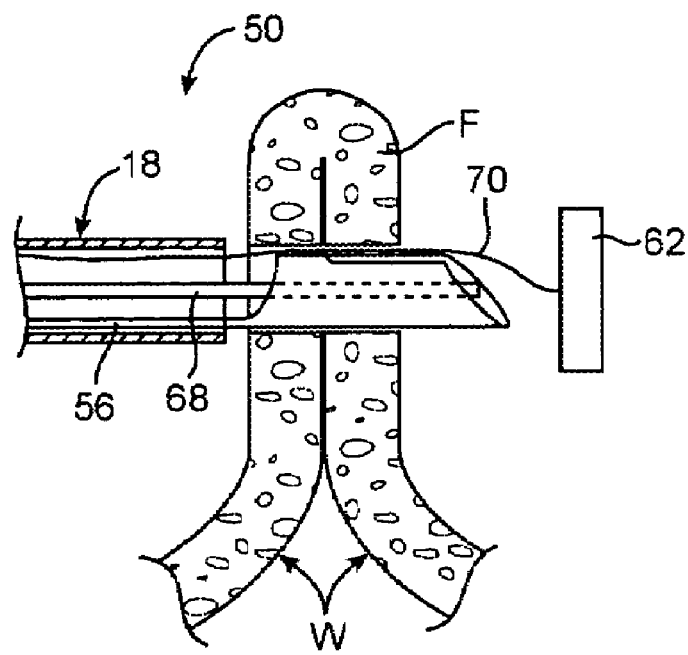
Figure 3D:
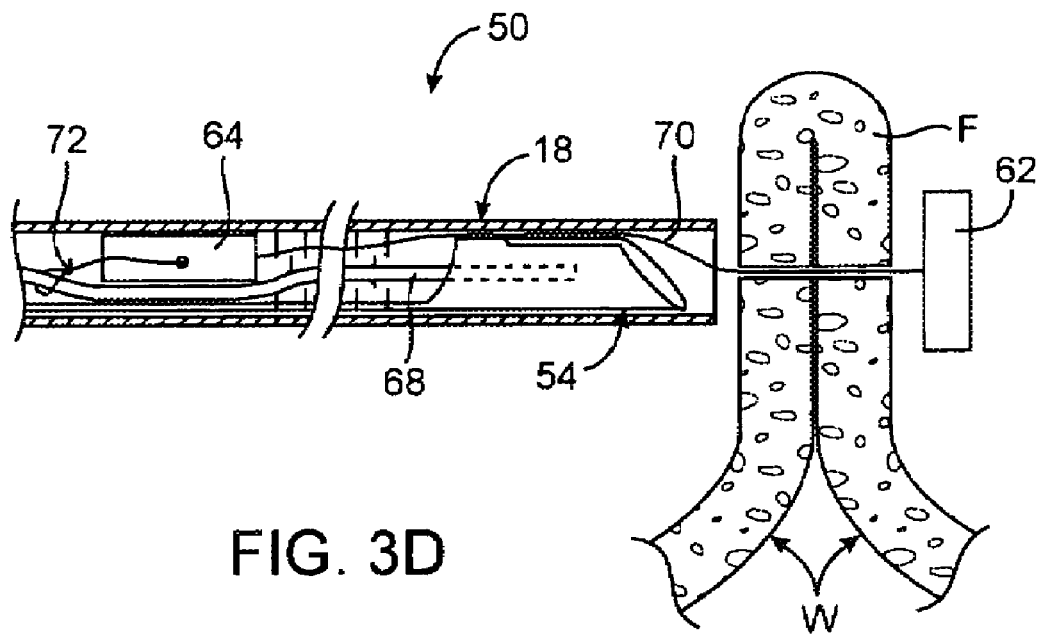

After needle assembly 48 has been pushed distally out through launch tube opening 24 and penetrated into and/or through tissue fold F, as shown in FIG. 3B, anchor pushrod or member 68 may be actuated also via its proximal end to eject distal anchor 62, as shown in FIG. 3C. Once distal anchor 62 has been ejected distally of tissue fold F, FIG. 3D shows how needle 54 may be retracted back through tissue fold F by either retracting needle 54 back within launch tube lumen 52 or by withdrawing the entire anchor delivery assembly 50 proximally relative to tissue fold F.

Figure 3E:
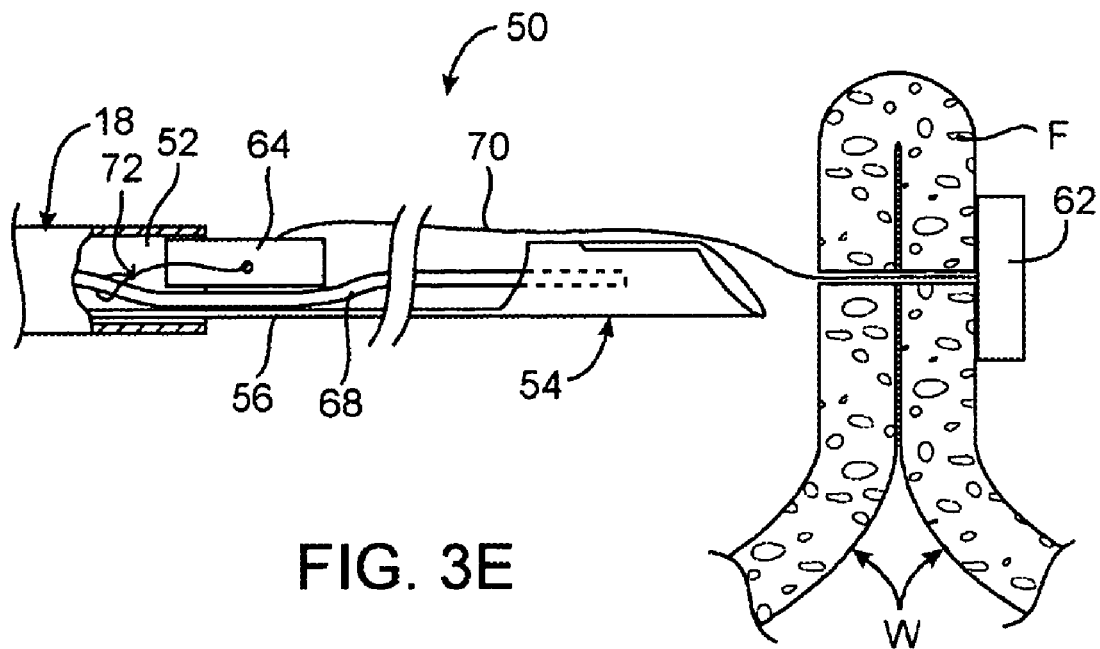
Figure 3F:
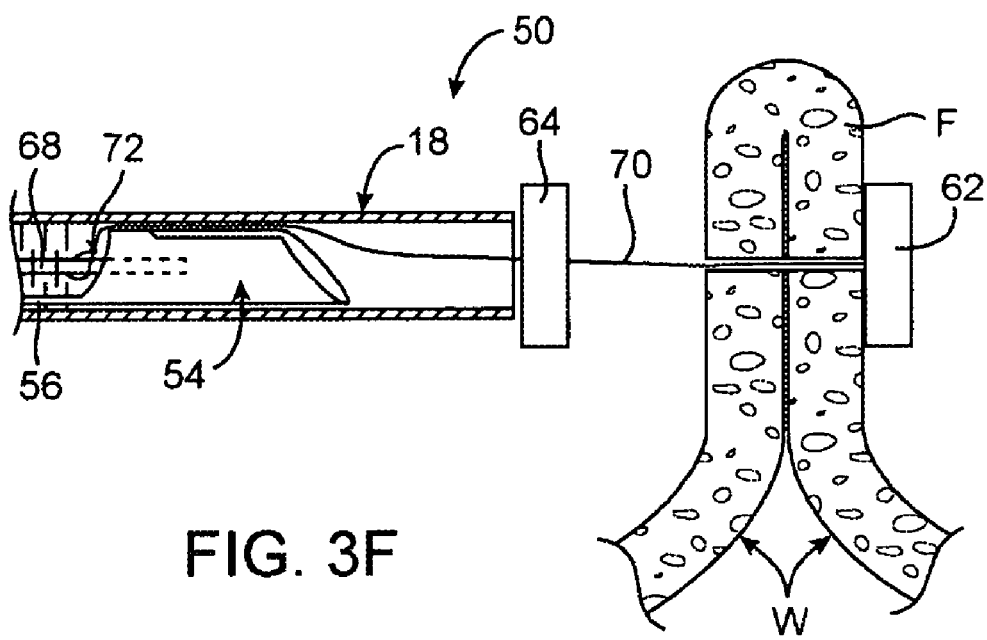
Figure 3G:
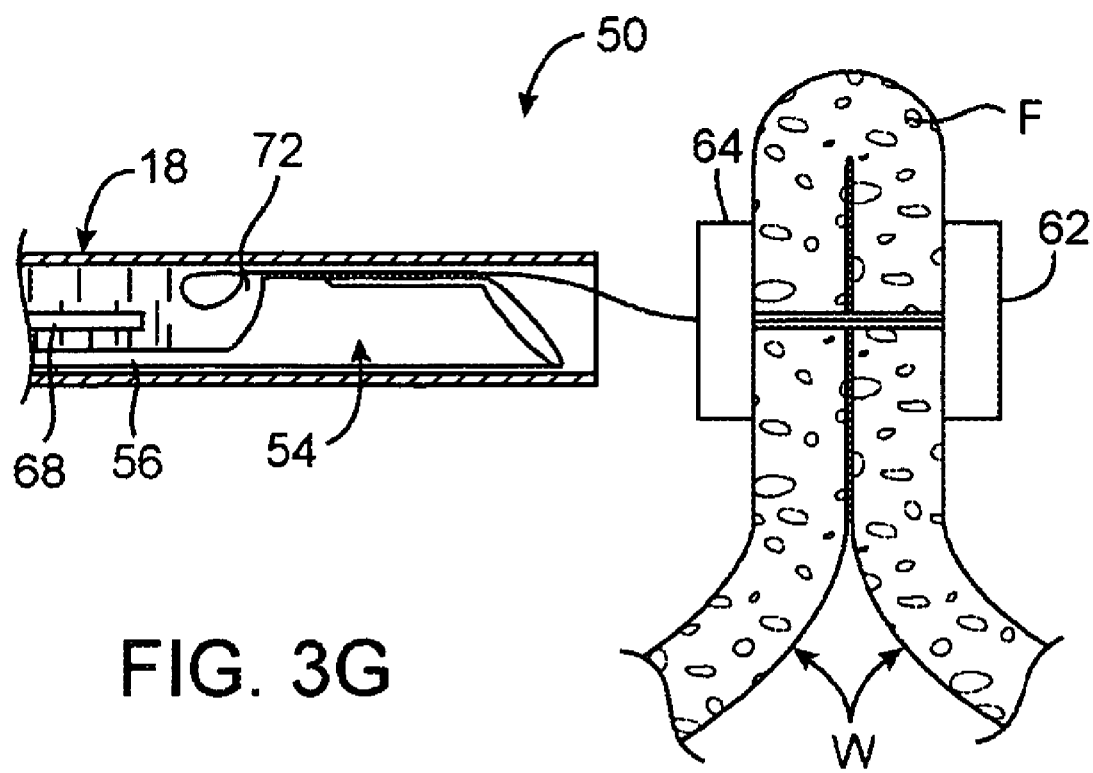

FIG. 3E shows that once needle 54 has been retracted, proximal anchor 64 may then be ejected from launch tube 18 on a proximal side of tissue fold F. With both anchors 62, 64 disposed externally of launch tube 18 and suture 70 connecting the two, proximal anchor 64 may be held against the distal end of launch tube 18 and urged into contact against tissue fold F, as shown in FIGS. 3F and 3G, respectively. As proximal anchor 64 is urged against tissue fold F, proximal anchor 64 or a portion of suture 70 may be configured to provide any number of directionally translatable locking mechanisms which provide for movement of an anchor along suture 70 in a first direction and preferably locks, inhibits, or prevents the reverse movement of the anchor back along suture 70. In other alternatives, the anchors may simply be delivered through various elongate hollow tubular members, e.g., a catheter, trocars, etc.

With respect to the anchor assemblies described herein, the types of anchors shown and described are intended to be illustrative and are not limited to the variations shown. For instance, several of the tissue anchor variations are shown as "T"-type anchors while other variations are shown as reconfigurable "basket"-type anchors, which may generally comprise a number of configurable struts or legs extending between at least two collars or support members. Other variations of these or other types of anchors are also contemplated for use in an anchor assembly. Examples of anchors which may be utilized are disclosed in co-pending U.S. patent application Ser. No. 10/612,170, filed Jul. 1, 2003, which is incorporated herein by reference in its entirety. Moreover, a single type of anchor may be used exclusively in an anchor assembly; alternatively, a combination of different anchor types may be used in an anchor assembly. Furthermore, the different types of cinching or locking mechanisms are not intended to be limited to any of the particular variations shown and described but may be utilized in any of the combinations or varying types of anchors as practicable.

To accomplish the secure placement of anchors having uni-directional anchor movement over the suture in a self-locking manner, various devices and methods may be utilized. FIGS. 4A and 4B show side and end views, respectively, of one anchor variation 80 which is illustrated in the form of a T-type anchor. Although a T-type anchor is shown, the methods and devices used to cinch the anchor may be utilized in other types of anchors, which will be described below. Variation 80 may generally comprise an anchor body 82 having a circular, rectangular, square, etc., cross-section which defines openings 84 and 86 on opposing sides of the anchor 80. Locking block or member 88 may be slidably disposed within anchor body 82 and define a tapered face 90 on the side of block 88 which tapers to at least one of the openings, in this case opening 86. Openings 84, 86 are preferably aligned with one another although this is not necessary.

Suture 94 may be routed through opening 84, around locking block 88, and back out through opening 86 such that when anchor body 82 is translated in the direction of arrow 96, anchor body 82 may slide freely over suture 94 due to the manner of tapered face 90 contacting suture 84 within opening 84. However, if anchor body 82 were translated in the opposite direction, tension within suture 94 may pull locking block 88 via suture 94 placed over contact surface 92 such that when block 88 translates in the direction of arrow 98, suture 94 at opening 86 is forced into groove 100 defined along the leading edge of block 88, as shown in FIG. 4B. This cleating action may effectively inhibit or prevent any further movement of anchor body 82 over suture 94. Accordingly, anchor body 82 may be moved uni-directionally relative to suture 94 and a distally located anchor to effectively cinch tissue therebetween.

FIG. 5 illustrates another cinching anchor in the side view of anchor variation 110. In this variation, anchor body 112 similarly defines openings 114 and 116 through which suture 96 may be routed. Locking block or member 118, which may similarly also define tapered face 120 may be slidably disposed within anchor body 112. Locking block 118 may be urged via a biasing member, for instance spring 122, to maintain a biasing force against suture 94 passing through anchor body 112. As anchor body 112 is translated over suture 94 in the direction of arrow 96, tapered face 120 may allow suture 94 to pass freely between openings 114, 116. However, if anchor body 112 were to be moved in the opposite direction, biasing member 122 may force locking block 118 to exert a force at its leading edge against suture 94, thereby preventing its movement and allowing only uni-directional movement.

Yet another locking anchor variation 130 is shown in the side view in FIG. 6. In this variation, anchor body 132 also defines openings 134, 136 through which suture 94 may pass. Within anchor body 132, multiple locking blocks or members 138, 140 may be configured to become biased in opposing directions via biasing members or springs 142, 144, respectively. Each of locking blocks 138, 140 may define an opening through which suture 94 may pass. Thus, when anchor body 132 is slowly moved over suture 94 in a first direction, the anchor may translate freely. However, when moved quickly in the opposite direction, the biasing members 142, 144 may urge their respective locking blocks 138, 140 in directions 146, 148 to create a tortuous path through the blocks and inhibit or prevent the reverse movement of anchor body 132 relative to suture 94.

FIG. 7 shows a perspective view of another locking anchor variation 150 in which anchor body 152 defines an opening 154 having a tapered or grooved portion 156. Opening 154 may be sized to allow suture 94 to pass through opening 154 such that anchor body 152 may be translated freely relative to suture 94. Once anchor body 152 has been desirably positioned relative to the tissue fold or to the opposing anchor, suture 94 may be manipulated to slide into tapered or grooved portion 156, which preferably defines a diameter which is less than a diameter of suture 94. Sliding suture 94 into tapered or grooved portion 156 may lock a position of anchor body 152 relative to suture 94 due to the cleating effect of grooved portion 156 on suture 94.

FIGS. 8A and 8B show cross-sectional side and top views, respectively, of another locking anchor variation 160 in which anchor body 162 may define a through-hole passage or opening 164 through which suture 94 may pass. Anchor body 162 may have one or several levered, flapped, or biased locking members 166 which may be integrally formed with anchor body 162. These locking members 166 may be formed radially about opening 164 such that when suture 94 is absent, the resting configuration of locking members 166 define an opening 164 having a diameter less than that of the suture 94 passed through. Locking members 166 may be biased to protrude in a single direction, as shown in FIG. 8A, such that when anchor body 162 is moved in a first direction over suture 94, the anchor 162 passes freely. However, when anchor body 162 is moved in the opposing direction over suture 94, locking members 166 engage onto suture 94 and prevent any reverse translation, thereby enabling uni-directional movement and locking of anchor body 162. Although five locking members 166 are shown, any number of members may be utilized as practicable and as desired to effect a desired degree to locking.

FIG. 8C shows a cross-sectional side view of anchor body 162 in combination with a modified suture 168 having integrated features or protrusions 170 defined along its length. Features or protrusions 170 may be defined uniformly at regular intervals along the length of suture 168 or intermittently, depending upon the desired effects, to enhance the locking ability of the anchor body onto the suture. Moreover, the features or protrusions 170 may be integrally formed protrusions or they may simply comprise knotted sections of suture. Sutures which are modified or knotted may be optionally utilized in any of the locking anchor variations as described herein in place of conventional sutures, depending upon the desired degree of locking and locking effects.

As shown in the cross-sectional views of FIGS. 9A and 9B of locking anchor variations 180 and 188, respectively, anchor body 182 may also comprise biased locking members 184, contained within the anchor body 182. The number and configuration of locking members 184 may be varied as desired and may optionally be apposed, as shown in FIG. 9A, or utilize a single member 184, as shown in anchor variation 188 in FIG. 9B. The figures show knotted suture 186 used with anchor variation 180; however, conventional sutures may also be utilized.

FIG. 9C shows another modification of suture 94 which may be utilized with any of the anchor locking variations shown herein. The portions of suture 94 which come into contact with the anchor locking mechanisms may be coated with a material having a relatively higher frictional coefficient, i.e., a coefficient of friction that is higher than the underlying suture material. For example, the portion of suture 94 may be coated with a metallic covering or slid within sleeve 181, which may be made of a metallic material such as Titanium, Nitinol, stainless steel, etc. to enhance the locking force between suture 94 and the anchor. As shown in the figure, if sleeve 181 is utilized, the ends 183, 185 of sleeve 181 may be crimped onto suture 94. One or several openings 187 may also be defined along sleeve 181 to further enhance the locking capability between suture 94 and the locking mechanism.

Aside from the use of mechanical locking features integrated within or with the anchor bodies, locking mechanisms may also utilize a variety of knotting techniques. Conventional knots, which are typically tied by the practitioner either within the body or outside the body and advanced over the suture length, may be utilized for locking the anchor in place relative to the tissue fold and opposing anchor; however, self-locking knots which enable the uni-directional travel of an anchor body relative to the suture and tissue are desirable.

FIG. 10 shows locking anchor assembly 190 with distal anchor 192, which may be positioned distally of a tissue fold, and proximal anchor 194, which may be positioned proximally of a tissue fold or folds. In this variation, suture 94 may be routed through proximal anchor 194 via openings 196, 198 and extended to distal anchor 192. At distal anchor 192, suture 94 may be routed through opening 200 and over pin 202 positioned within distal anchor 192. Pin 202 may function as a pulley over which suture 94 may travel during anchor locking adjustments. Suture 94 may then be routed back towards proximal anchor 194 through opening 204 and define loop 206 through which the proximal portion of suture 94 passes to thereby create a choke-type loop. The terminal end of suture 94 may then be anchored at fixed end 208 within the body of proximal anchor 194.

In operation, when tension is applied to suture 94 or when proximal anchor 94 is advanced distally, proximal anchor 194 and distal anchor 192 may be freely drawn towards one another to secure any tissue fold or folds (not shown for clarity) disposed therebetween. However, if proximal anchor 194 were pulled or urged in the opposite direction away from the tissue or from distal anchor 192, loop 206 would "choke" suture 94 and prevent any reverse movement of proximal anchor 194.

FIG. 11A shows a perspective view of locking anchor assembly 210 having distal anchor 212 and proximal anchor 214 with suture 94 extending between the two anchors. Terminal end 230 of suture 94 may be knotted or otherwise retained by proximal anchor 214 and routed through opening 216 and back through opening 218 to create looped portion 228, both openings 216, 218 being defined in proximal anchor 214. Suture 94 may be routed from opening 218 and through distal anchor 212 via openings 222, 224. Suture 94 may then be routed back to proximal anchor 214 through an opening 220 and wrapped 226 about looped portion 228 to continue on proximally. This knotted configuration facilitates advancement of proximal anchor 214 towards distal anchor 212 but chokes suture 94 when proximal anchor 214 is moved in an opposing direction.

FIGS. 11B and 11C show top and cross-sectional side views of an alternative variation on proximal anchor 214 (and distal anchor 212, if desired). As shown, anchor 214 may optionally define grooves or channels 232 which extend at least partially between openings 216, 218, and 220. These grooves or channels 232, as seen in FIG. 11C, may be sized such that any of the overlying suture 94 are cinched or wedged into grooves 232 to facilitate the cinching action of anchor 214 with respect to suture 94.

Figure 12A:
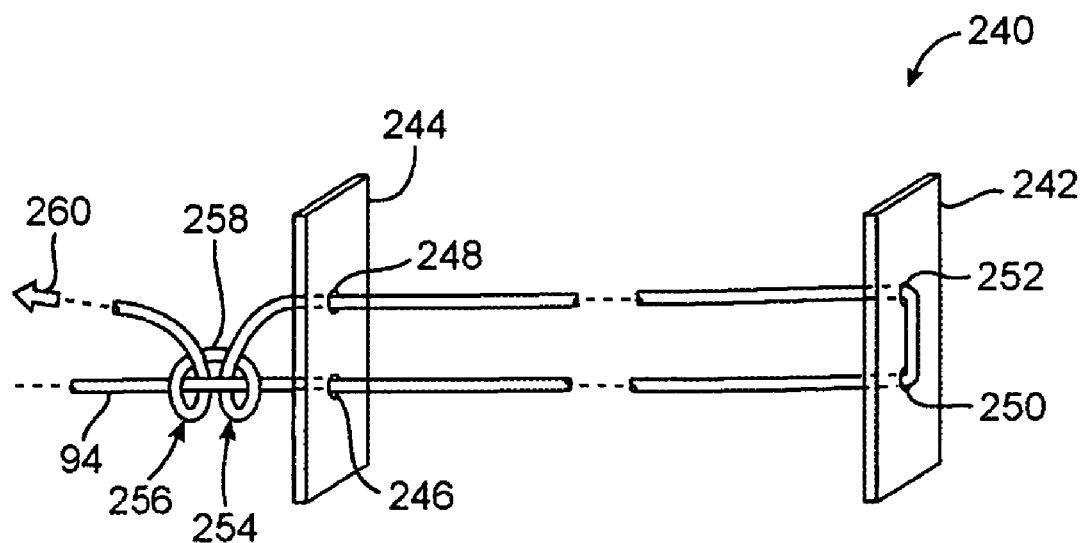

Another locking anchor assembly 240 is shown in the perspective view of FIG. 12A, which shows distal anchor 242 and proximal anchor 244 with suture 94 extending between the two anchors. Suture 94 may be routed through opening 246 defined through proximal anchor 244 and passed through distal anchor 242 via openings 250, 252. Suture 94 may then be routed back towards proximal anchor 244 and passed through opening 248 to create at least two adjacent loops (half hitch knots) 254, 256 with looped section 258. During cinching of proximal anchor 244 against the tissue, the knotted suture may be slid distally with proximal anchor 244. Once proximal anchor 244 has been desirably positioned along suture 94, the terminal end of suture 94 may be pulled, as shown by arrow 260, to alter the knot configuration, commonly called changing the dressing of the knot, such that the knot becomes locked onto suture 94 and prevents any reverse movement of proximal anchor 244.

Figure 12B:
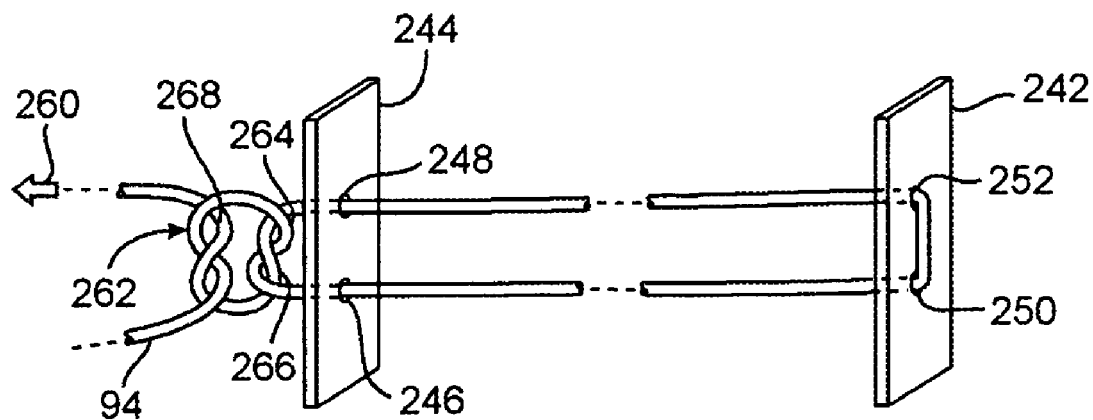

FIG. 12B also shows a perspective view of another locking anchor variation similar to that shown in FIG. 12A. In this variation, suture 94 may be wrapped into two intertwined loops 264, 266 and further wrapped again into adjacent intertwined loops 262, 268. Distal advancement of the knotted configuration along with proximal anchor 244 may be accomplished until the terminal end of suture 94 is placed under tension, as shown by arrow 260. Tension may be applied once proximal anchor 244 has been desirably positioned along suture 94 to lock the knot into position and prevent any reverse movement of proximal anchor 244 along suture 94.

Figure 12C:
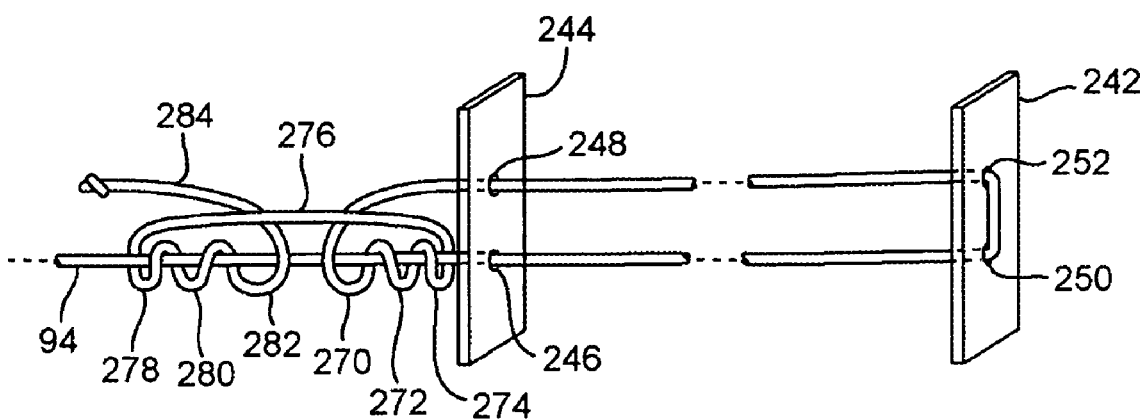
Figure 12D:
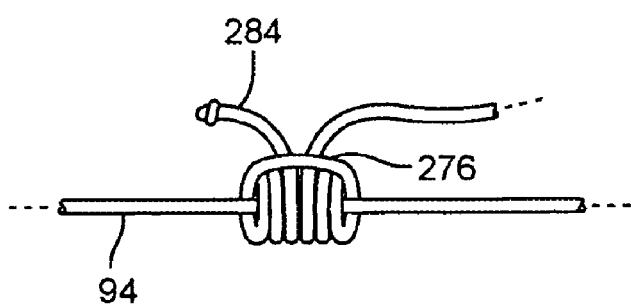

FIG. 12C shows a perspective view of another anchor locking assembly similar to the variations above. The knot may be modified by wrapping suture 94 into a first set of several loops, shown as three loops 270, 272, 274, although in other variations, any number of loops may be utilized depending upon the desired locking effects. Suture 94 may then be wrapped in a second set of several additional loops in a proximally adjacent position about suture 94, shown as loops 278, 280, 282 joined by looped section 276. Likewise, any number of loops in the second set may be utilized either independent of the number of loops in the first set or to mirror the first set of loops. In either situation, once suture terminal end 284 is tightened, a knotted configuration, as shown in FIG. 12D, is formed which may be freely slid along suture 94 provided the knotted configuration itself is pushed along suture 94, e.g., via a pusher tube, knot pusher, etc. However, once tension is applied along suture 94 by proximal anchor 244 pushing against the knot and by the tension created in the suture extending between anchors 242, 244, the knot locks against suture 94 and prevents reverse movement of proximal anchor 244 along suture 94.

Figure 12E:
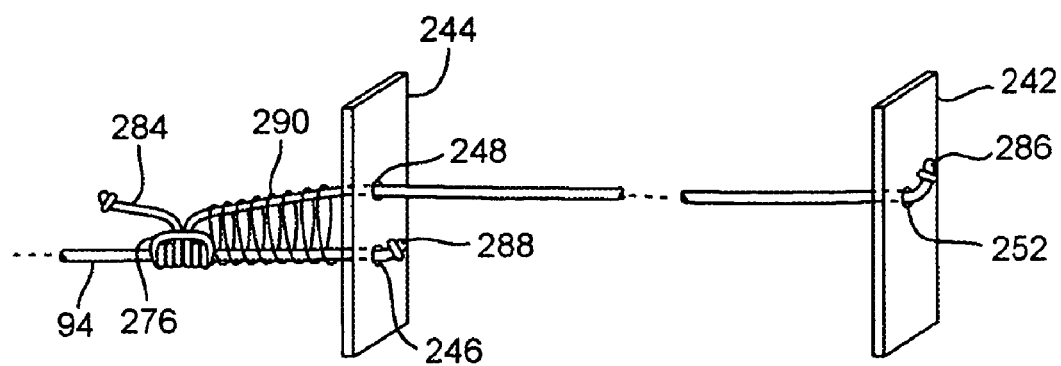

FIG. 12E shows a perspective view of another locking anchor variation similar to the variation shown in FIG. 12D yet having a single suture traverse between anchors 242, 244. In this variation, suture 94 may have terminal end 286 anchored or retained by distal anchor 242 at opening 252 and have a single suture traverse to proximal anchor 244. A second terminal end 288 may also be anchored or retained by proximal anchor 244 at opening 246. The portions of suture 94 extending between proximal anchor 244 and the knot may have a biasing member, e.g., spring 290, disposed over one or both lengths of suture to maintain proximal anchor 244 and the knot under a constant force to ensure that the knot is maintained under a locking force to prevent the reverse travel of proximal anchor 244.

Figure 12F:
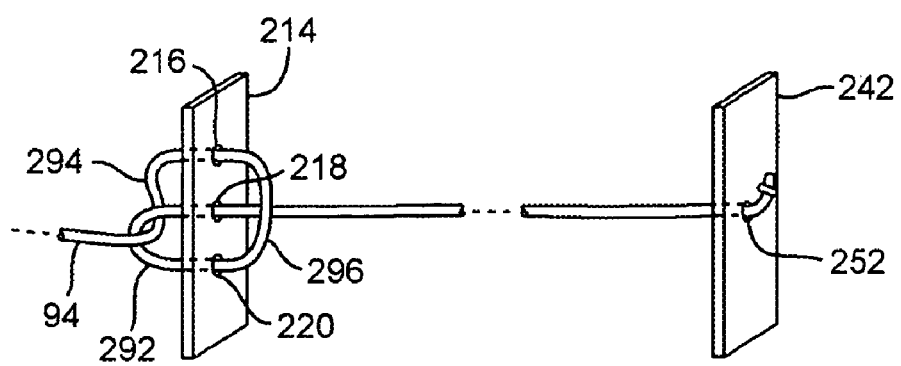

Yet another variation of a locking anchor variation having a single suture traversing the anchors is shown in the perspective view of FIG. 12F. A terminal end 252 of suture 94 may be anchored or retained at distal anchor 242 and routed to proximal anchor 214 through opening 218. The length of suture 94 may form loop 292 on a first side of proximal anchor 214 and a second loop 296 on the opposite side of proximal anchor 214 between openings 216, 220. Suture 94 may then be wrapped about loop 292 via loop 294 on the first side to form an interlocking suture loop. This variation is also effective in allowing proximal anchor 214 to translate over suture 94 towards the tissue and distal anchor 242 yet prevent reverse movement of proximal anchor 214 due to a choking action by the intertwined suture loops on the proximal side of proximal anchor 214.

Figure 12G:
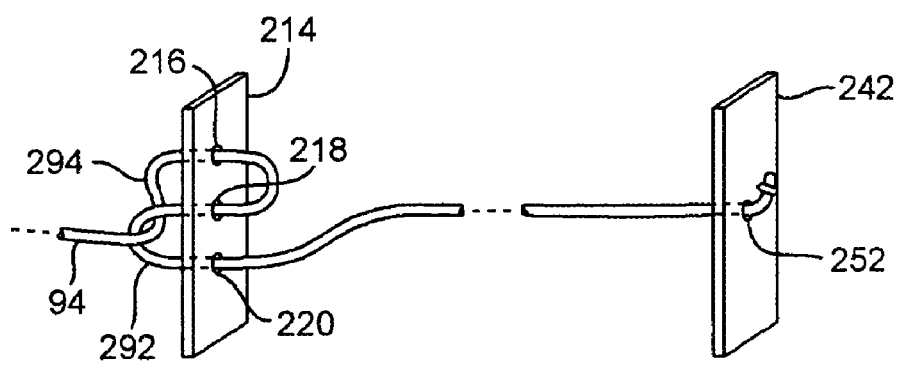

FIG. 12G shows a perspective view of another locking anchor variation similar to that shown in FIG. 12F. Here, suture 94 may be routed through opening 220 in proximal anchor 214 to form loop 292 before being passed through openings 218 and 216 and intertwining loop 294 through loop 292. Likewise, this variation is also effective in allowing proximal anchor 214 to translate over suture 94 towards the tissue and distal anchor 242 yet prevent reverse movement of proximal anchor 214.

As mentioned above, the locking and cinching mechanisms described herein may be utilized with a variety of different anchor types. For instance, the cinching mechanisms described above may be used not only with T-type anchors but also with reconfigurable basket-type anchors. Described hereinafter are basket-type anchors configured for implantation or placement against tissue in a similar manner as described previously and examples of how cinching mechanisms may be utilized in securing tissue plications. Moreover, additional cinching mechanisms which are preferably utilizable with basket-type anchors are also described below.

When cinching or locking basket-type anchors, the baskets may be delivered into or through the tissue in the same or similar manner as described above, particularly as shown in FIGS. 3A-3G. For example, FIG. 13A shows anchor delivery system 300 in proximity to tissue fold F. Again, tissue fold F may be disposed within a gastrointestinal lumen, such as the stomach, where tissue wall W may define the outer or serosal layer of the stomach. Delivery push tube or catheter 302 may be disposed within launch tube 18 proximally of basket anchor 306, which is shown in a compressed delivery configuration with a relatively low profile when disposed within needle lumen 58 of needle 54. A single basket anchor 306 is shown disposed within needle 54 only for illustrative purposes and is not intended to be limited by the number of basket anchors; rather, any number of basket anchors may be disposed within needle lumen 58 as practicable depending upon the desired procedure and anchoring results.

Suture 94 may be routed through or externally of push tube lumen 304 and further routed within and/or through proximal collar 310 of anchor 306. The terminal end of suture 94 may be routed within anchor 306 and affixed to distal collar 308 in one variation. Alternatively, suture 94 may be affixed or anchored within anchor 306 or at proximal collar 310 depending upon the desired effect and procedure being performed. Moreover, if multiple anchors are utilized in a tissue plication procedure, suture 94 may be routed through anchor 306 such that the anchor 306 may freely slide along or over suture 94.

The basket anchors may comprise various configurations suitable for implantation within a body lumen. Basket anchors are preferably reconfigurable from a low profile delivery configuration to a radially expanded deployment configuration in which a number of struts, arms, or mesh elements may radially extend once released from launch tube 18 or needle 54. Materials having shape memory or super-elastic characteristics or which are biased to reconfigure when unconstrained are preferably used, e.g., spring stainless steels, Ni—Ti alloys such as Nitinol, etc. The basket anchor 306 is illustrated as having a number of reconfigurable struts or arm members 312 extending between distal collar 306 and proximal collar 310; however, this is intended only to be illustrative and suitable basket anchors are not intended to be limited to baskets only having struts or arms. Examples of suitable anchors are further described in detail in U.S. patent application Ser. No. 10/612,170, which has already been incorporated herein above.

FIG. 13A shows basket anchor 306 delivered through tissue fold F via needle 54 and launch tube 18. As above, the other parts of the plication assembly, such as upper and lower bail members 20, 26, respectively, and tissue acquisition member 28 have been omitted from these figures only for clarity.

FIG. 13B shows one variation where a single fold F may be secured using basket anchor 306'. As seen, basket anchor 306' has been urged or ejected from needle 54 and is shown in its radially expanded profile for placement against the tissue surface. In such a case, a terminal end of suture 94 may be anchored within the distal collar of anchor 306' and routed through tissue fold F and through, or at least partially through, proximal anchor 318, where suture 94 may be cinched or locked proximally of, within, or at proximal anchor 318 via any number of cinching mechanisms 316 described herein. Proximal anchor 318 is also shown in a radially expanded profile contacting tissue fold F along tissue contact region 314. Locking or cinching of suture 94 proximally of proximal anchor 318 enables the adequate securement of tissue fold F.

If additional tissue folds are plicated for securement, distal basket anchor 306 may be disposed distally of at least one additional tissue fold F', as shown in FIG. 13B, while proximal anchor 318 may be disposed proximally of tissue fold F. As above, suture 94 may be similarly affixed within distal anchor 306 and routed through proximal anchor 318, where suture 94 may be cinched or locked via proximal anchor 318, as necessary. If tissue folds F and F' are to be positioned into apposition with one another, distal basket anchor 306 and proximal anchor 318 may be approximated towards one another. As described above, proximal anchor 318 is preferably configured to allow suture 94 to pass freely therethrough during the anchor approximation. However, proximal anchor 318 is also preferably configured to prevent or inhibit the reverse translation of suture 94 through proximal anchor 318 by enabling uni-directional travel of anchor 318 over suture 94. This cinching feature thereby allows for the automated locking of anchors 306, 318 relative to one another during anchor approximation.

Aside from the anchor cinching or locking mechanisms utilizing looped and knotted sutures for facilitating uni-directional locking, various mechanisms utilizing friction may also be implemented. FIGS. 14A and 14B show cross-sectional side views of one variation in cinching assembly 320. Proximal collar 322, proximal portions of struts 312, and distal portions of launch tube 18 are shown and other features of the assembly and tissue fold F have been omitted from the figure only for clarity.

A locking or cinching collar or collet 326 may be positioned within launch tube 18 proximally of anchor collar 322. Cinching collet 326 may comprise a cylindrically shaped member defining a lumen therethrough for passage of suture 94. A distal end of cinching collet 326 may have at least one and preferably several clamping arms or teeth 328 which are configured to cinch or clamp down upon suture 94 passing through. Proximal anchor collar 322 may be sized to correspondingly receive cinching collet 326 therewithin to create an interference fit. relative to an outer diameter of cinching collet 326. A distal portion of anchor collar 322 may also define a tapered or angled portion 324 such that when cinching collet 326 is advanced within anchor collar 322, angled portion 324 may effectively force clamping arms or teeth 328 to cinch radially inward upon suture 94.

In operation, once proximal anchor 318 has been desirably positioned relative to tissue fold F and/or the distal anchor and with proximal collar 322 positioned within launch tube 18, delivery push tube 302 may be advanced distally to urge cinching collet 326 into anchor collar 322 such that clamping arms or teeth 328 are clamped onto suture 94 and cinching collet 326 is friction-fitted within anchor collar 322. Anchor collar 322 may then be urged out of launch tube 18 and the anchor left against the tissue surface.

Another cinching assembly variation 330 is shown in the cross-section view of FIGS. 15A and 15C. Launch tube 18 has been omitted from these figures for clarity only. Delivery push tube 332 is shown as defining suture lumen 334 and locking member or pin lumen 336 therethrough. Although two separate lumens are shown, a single common lumen may be utilized in alternative variations. With proximal anchor collar 344 positioned distally of push tube 332, suture 94 may be routed through suture lumen 334 and through collar lumen 346. Locking member or pin 338 may be positioned within lumen 336 proximally of collar lumen 326. FIG. 15B shows an end view of push tube 332 with locking pin 338 and suture 94 positioned within prior to cinching of the anchor.

Once the anchor has been desirably positioned relative to the tissue, suture 94 may be pulled proximally such that anchor collar 344 rests against the distal end of push tube 332. Locking pin 338, which may define a tapered or radiused end 340 to facilitate its insertion into collar lumen 346, may be urged distally via push rod 342 to force locking pin 338 into anchor collar 344 such that the portion of suture 94 within anchor collar 344 becomes effectively wedged and thereby prevents further movement of the anchor along suture 94. FIG. 15C shows a cross-sectional side view of locking pin 388 having been urged into anchor collar 344 in a frictional engagement with suture 94. FIG. 15D shows a cross-sectional end view of collar 344 with locking pin 388 and suture 94 positioned within.

FIG. 15E shows a perspective view of another cinching variation 331 which is similar to the variation described above. One or more tapered pins or blocks 339 may be slidably disposed within tapered channel 335 defined in proximal collar 333. The figure shows two tapered pins 339, although a single pin may be utilized or more than two pins may also be used. If two or more pins 339 are utilized, suture 94 may be passed between the pins 339. Pins 339 may be free to slide along inner surface 337 of channel 335 in the direction of arrows 345 depending upon the direction of travel of suture 94 through channel 335. FIG. 15F shows a perspective view of only pins 339 for clarity; as seen, pins 339 may be tapered distally from a larger diameter to a smaller diameter and although pins 339 are shown as semi-circularly shaped members, contact surface 341 may be curved or arcuate to better contact suture 94. Moreover, contact surface 341, which contacts suture 94 passing through channel 335, may define a roughened surface or it may alternatively define a plurality of serrations, teeth, projections, etc., to facilitate contact against suture 94.

In use, as proximal collar 333 is translated in the direction of arrow 343, pins 339 may be forced proximally such that suture 94 may pass freely through channel 335. However, if proximal collar 333 were to be translated in the opposing direction, pins 339 may be forced in the opposite direction to cinch down upon suture 94 within channel 335 and thereby inhibit any further motion.

An alternative variation of the assembly is shown in the cross-sectional views of FIGS. 15G and 15H, which show a cinching anchor having a retractable pin. FIG. 15G shows proximal collar 347 with one or more retracting arms 349 extending proximally from collar 347. Retracting arms 349 may be configured to pivot at bend 353 when urged via a compression force applied at bend 353 in the direction of arrows 355. The application of this compression force may urge pin support collar 357 which is defined at a proximal portion of arms 349, to move in the direction of arrow 359. This in turn may move pin 351, which extends from pin support collar 357, proximally out of proximal collar 347 to thereby release suture 94 from its locked position. In one variation, retracting arms 349 may be biased to retain pin 351 within proximal collar 347 unless a compression force is applied at bend 353.

FIGS. 16A and 16B show cross-sectional side views of another variation of cinching assembly 350. Cinching assembly 350 may generally comprise outer tubing 352 and inner tubing 358 rotatingly positioned within outer tubing lumen 354. Cinching member 362 may be positioned distally of outer tubing 352 and may generally comprise a collar base 364 and cinching collar 374 projecting proximally from collar base 364. Cinching collar 374 is preferably tapered and threaded and may also be longitudinally slotted such that rotatable collar 368 may be rotatingly disposed upon slotted cinching collar 374. A distal end of outer tubing 352 may define one or several engaging members 356 which are adapted to engagingly contact detents or keyed engagement interfaces 366 located on collar base 364. Inner tubing 358 may also define one or several engaging members 363 which are also adapted to engagingly contact detents or keyed engagement interfaces 372 located on the rotatable cinching collar 374. Suture 94 may be routed through inner tubing lumen 360, through cinching collar 374, and through proximal anchor collar 310.

In operation, suture 94 may pass freely through assembly 350. Once the anchor has been desirably positioned, engaging members 356 on outer tubing 352 may be correspondingly engaged against interface 366 and engaging members 363 on inner tubing 358 may be engaged against interface 372. With suture 94 tensioned appropriately, outer tubing 352 may be held stationary while inner tubing 358 is rotated to torque rotatable collar 368 about threaded cinching collar 374. As rotatable collar 368 is torqued onto cinching collar 374, the tapered shape may urge the slotted members to cinch upon suture 94 passing therethrough. Stand-offs 370, which may protrude from rotatable collar 368, may be adjusted in height to control how far rotatable collar 368 may be torqued onto collar base 364 such that the degree to which rotatable collar 368 is torqued about cinching collar 374 may be desirably adjusted. Once the cinching collar 374 has been desirably cinched onto suture 94, proximal anchor collar 310 may be ejected from launch tube 18 along with the cinching assembly, as shown in FIG. 16B.

Another variation on cinching assembly 380 may be seen in the cross-sectional views of FIGS. 17A and 17B. Assembly 380 is similar to cinching assembly 330 shown above in FIGS. 15A to 15D. Delivery push tube 332 and push rod 342 have been omitted from these figures only for clarity. In this variation, when locking pin 338 is pushed distally into proximal collar 388, a retaining tube member 384 may be utilized to provide a counterforce to stabilize proximal collar 388 during cinching. Retaining tube member 384 may generally comprise one or several collar engaging arms 386 for engaging proximal anchor collar 388 at collar detents 390 defined along anchor collar 388. During the insertion of locking pin 338 into collar 388, collar engaging arms 386 may be positioned within launch tube 18 or within retractable sleeve 382. After locking pin 338 has been inserted within anchor collar 388, engaging arms 386 may be advanced distally out of launch tube 18 or retractable sleeve 382 may be withdrawn proximally to expose engaging arms 386. Once free of any constraining forces, engaging arms 386 may be biased to spring or open radially to then release proximal anchor collar 388 in a cinched configuration.

Another variation on cinching assembly 400 is shown in FIGS. 18A to 18D, in which proximal anchor collar 406 may comprise one or several biasing members or cinching tabs 408 within collar 406. Each of the tabs 406 may be biased to project inwardly such that suture 94 passing through is automatically cinched and locked in position, as shown in FIG. 18A. A suture release member 404, which may generally comprise a cylindrically shaped tube or member having a tapered surface 410 and a suture lumen 412 defined therethrough, may be positioned within anchor collar 406 during anchor positioning to allow free passage of suture 94 through the anchor, as shown in FIG. 18B. FIG. 18C shows an end view of release member 404 defining suture lumen 412 extending therethrough. FIG. 18D shows a perspective view of release member 404 to show tapered surface 410 and suture lumen 412 in better detail. Tapered surface 410 may be omitted but is preferably to facilitate the insertion and removal of release member 404 from anchor collar 406. When the anchor has been desirably positioned and is ready to be locked in place over suture 94, tubular member 402 may engage suture release member 404 for withdrawal from anchor collar 406. The removal of release member 404 may cause cinching tabs 408 to lock upon suture 94 and prevent the further movement of the anchor relative to suture 94.

FIGS. 19A and 19B show another variation of cinching assembly 420 in which a deformable cinching member 424 may be positioned within the anchor distally of anchor collar 422. Cinching member 424 may define a tapered outer surface such that when the anchor is ready to be secured to suture 94, the insertion of cinching member 424 into collar 422 may compress cinching member 424 about suture 94 such that any further movement of the anchor is prevented. Cinching member 424 may be pulled into anchor collar 422 via pull wire 426, which may be manipulated at its proximal end by the surgeon or user when desired.

FIGS. 20A to 20D show cross-sectional views of another variation in cinching assembly 430. As shown in FIG. 20A, proximal anchor collar 432 may comprise a pivotable locking member 434 contained either within anchor collar 432 or proximally of collar 432. This example illustrates locking member 434 contained within collar 432. Suture 94 may pass through locking member 434, which is shown in the end view of collar 432 in FIG. 20B, as having two pivots 436. Moreover, locking member 434 and pivots 436 may be integrally formed from proximal collar 432. Pivoting locking member 434 may be biased to rotate about pivot 436 such that a resting position of locking member 434 is against an inner surface of collar 432. During distal anchor translation over suture 94, tension as represented by 20 arrow 438, on suture 94 may force pivot 434 into an open position where suture 94 may pass freely through. Upon having desirably positioned the anchor against tissue, locking member 436 may be biased to pivot in direction 440 to lock suture 94 against the inner surface of collar 432. Opposite movement of the anchor relative to suture 94 may act to further cinch locking member 434 against suture 94 and thereby further inhibit the movement of the anchor in the reverse direction.

A similar variation is shown in the cross-sectional side and perspective views of FIGS. 20E and 20F, respectively. In this variation, locking member 434' may extend proximally of proximal collar 432 at an angle relative to collar 432. Locking member 434' may be pivotable via pivot 436' such that locking member 434' may pivot in the direction of the arrows shown depending upon the direction which the tissue anchor is translated relative to suture 94. If proximal collar 432 is translated distally over suture 94, it may travel freely; however, if proximal collar 432 is translated proximally in the opposite direction, suture 94 may become wedged in a tapered portion of opening 442 through which suture 94 passes. Once suture 94 is wedged in tapered opening 442, locking member 434' may pivot towards proximal collar 432, where it is stopped from further motion, thereby locking the tissue anchor onto suture 94 and preventing its reverse motion.

FIGS. 21A and 21B show another cinching assembly variation 450 as seen in the cross-sectional side views. In this variation, delivery push tube 452 may be disposed proximally of locking collar 454 and proximal tapered anchor collar 458. Once the anchor has been desirably positioned relative to the tissue fold F, with suture 94 under tension, locking collar 454 may be urged distally via push tube 452 such that locking collar 454 slides over proximal anchor collar 458. An inner surface of locking collar 454 may be tapered and anchor collar 458 may also be tapered in a correspondingly opposed manner such that when locking collar 454 is mated with anchor collar 458, anchor collar 458 may cinch locking collar 454 upon suture 94 to thereby prevent any further movement of the anchor over suture 94. Both collars may be made from any of the same or similar materials, as described above.

In addition to friction-based locking and cinching mechanisms utilizable in tissue anchors, other mechanisms which create tortuous paths for the suture within or through the anchors may also be utilized for creating uni-directional locking.

One cinching anchor variation 460 is shown in the cross-sectional side view in FIG. 22A. As shown, suture 94 may be routed through anchor proximal collar 462 and looped over pulley or pin 466 contained within distal collar 464. Suture 94 may then be routed back through and looped 468 about suture 94 and tied with slip knot 470. As tension is applied to suture 94, slip knot 470 may prevent further movement of the anchor relative to suture 94.

FIGS. 22B and 22C show a variation which may be used in combination with cinching anchor variation 460 or alone. Pin 474 may optionally be positioned within proximal collar 462 and suture 94 may be wrapped or looped about itself around pin 474 in a manner as shown in the detail view of FIG. 22C. The configuration of loop 472 may allow for the uninhibited translation of the anchor in the direction of the arrow as shown; however, when the anchor is moved in the opposite direction, loop 472 may effectively cinch upon itself to thus prevent or inhibit the reverse motion of the anchor relative to suture 94.

Another cinching variation is shown FIGS. 22D and 22E. Suture 94 may be routed through proximal collar 462 with an additional length of cinching suture 476. The distal end of cinching suture 476 may form loop 478 which is wrapped about suture 94 and free to slide over suture 94. After the anchor has been desirably positioned relative to the tissue and with suture 94 preferably under tension, cinching suture 476 may be pulled proximally such that loop 478 is pulled into proximal collar 462 and becomes wedged against suture 94. The multiple lengths of suturing material utilized for loop 478 and suture 94 preferably form a cross-sectional area which is larger than an inner diameter of proximal collar 462 such that positioning loop 478 and suture 94 within collar 462 ensures a frictional lock which prevents further movement of the suture 94 relative to the anchor. Suture 94 and cinching suture 476 are preferably made from the same or similar materials although differing suture materials may also be used.

FIG. 23 shows a cross-sectional view of cinching assembly variation 480 in which proximal collar 482 may comprise pulley or pin 484 about which suture 94 may be looped once or several times 490. Distal collar 486 may also comprise pulley or pin 488 about which suture 94 may also be looped once or several times before being wrapped or looped 492 back about suture 94. The terminal end of loop 492 may be secured about suture 94 via slip knot 494. This configuration of looping allows for the anchor to be advanced uni-directionally relative to the suture and tissue, yet prevents or inhibits the reverse movement of the anchor and thus effectively enables the tissue to be cinched via the anchors.

Another cinching or locking anchor variation 500 is shown in the cross-sectional view of FIG. 24A. In creating a tortuous path for suture 94, cinching sleeve 506 may be positioned proximally of proximal collar 504 within or distally of delivery push tube 502. Cinching sleeve 506 may generally comprise a tubular structure having sleeve lumen 510 defined therethrough and a number of openings 508 defined along the length of sleeve 506. Openings 508 may be uniformly patterned along sleeve 506 or they may be randomly positioned. Moreover, any number of openings 508 may be utilized as practicable. In either case, suture 94 may be routed in various patterns throughout openings 508 and through sleeve lumen 510 before being routed through proximal collar 504. Once the anchor is to be locked, cinching sleeve 506 may be urged distally via delivery push tube 502. When urged or pushed distally, this may be done slowly so as to allow suture 94 to pass through the tortuous path created by suture 94 passing through openings 508. However, once cinching sleeve 506 has been advanced proximally adjacent to proximal collar 504, cinching sleeve 506 may become locked with proximal collar 504 pressing against sleeve 506.

FIG. 24B shows another variation of a cinching mechanism which utilizes a tortuous path. Cinching sleeve 512 may comprise a tubular structure having an opening 514 defined along a surface of sleeve 512 through which suture 94 may pass. Cinching sleeve 512 may be disposed within proximal collar 504 with suture 94 routed from outside of sleeve 512 and passing to within sleeve 512 through opening 514. In operation, because of the manner in which suture 94 is routed through sleeve 512 and into the anchor, distal translation of the anchor relative to the tissue and suture 94 is uninhibited. But when the anchor is reversed in direction relative to suture 94, suture 94 and cinching sleeve 512 may be drawn into the anchor and become locked due to the interference between suture 94, cinching sleeve 512, and proximal collar 504. Accordingly, an outer diameter of cinching sleeve 512 is preferably sized to be slightly less than an inner diameter of proximal collar 504 such that when suture 94 is passed through opening 514, cinching sleeve 512 becomes wedged against collar 504. Cinching sleeve 512 may be made from any of the same or similar materials as the anchors, as described above.

FIGS. 24C and 24D show another variation similar to cinching sleeve 512 described above. Cinching sleeve variation 516 may be similarly sized as sleeve 512 and may also similarly define an opening 514; however, sleeve 516 includes one or several retaining arms 518 defined on a distal end of sleeve 516. Any number of retaining arms 518 may be utilized provided that they extend radially and reside distally of proximal collar 504 such that they prevent sleeve 516 from sliding proximally out of collar 504. FIG. 24D shows a perspective view of cinching sleeve 516 with retaining arms 518 radially extended from the body of sleeve 516. Cinching sleeve 516 may also be made from the same or similar material as the anchor; for example, sleeve 516 may be fabricated from a material having superelastic characteristics, such as Nitinol. Accordingly, when cinching sleeve 516 is initially inserted through collar 504 and/or during anchor delivery through launch tube 18 into or through the tissue, retaining arm or arms 518 may be configured into a low profile with arm or arms 518 constrained into a tubular shape. Upon anchor release or upon being inserted through collar 504, retaining arms 518 may be released to extend radially.

Yet another variation 520 on cinching assembly is shown in FIG. 25A. Generally, assembly variation 520 may comprise cinching collar 522 located proximally of anchor proximal collar 524. Cinching collar 522 may be a tubular structure having superelastic material characteristics, such as those found in Nitinol. Obstructing members 526, which may be formed from portions of cinching collar 522, may be pressed or formed to extend into a lumen of cinching collar 522 such that a tortuous path is created for the passage of suture 94. Although three obstructing members 526 are shown in the figure, any number of obstructions as practicable may be created depending upon the desired tortuous path to be created.

Assembly 520 shows cinching collar 522 as a separate collar located proximally of anchor collar 524; however, the cinching collar may be integrated with the anchor collar such that a singular integral structure is formed, as shown in anchor variation 530 in the cross-sectional view of FIG. 25B. In either alternative during anchor placement relative to the tissue fold, retaining sleeve 534 may be inserted within cinching collar 522 to maintain obstructing members 526 in an open position for allowing suture 94 to pass freely through sleeve 534. Once the anchor has been desirably positioned, retaining sleeve 534 may be withdrawn, as shown in the perspective view of FIG. 25C, using any number of methods. Removal of retaining sleeve 534 will allow for obstructing members 526 to reconfigure inwardly in the direction of arrows 532 to thus reconfigure cinching collar 522 into a tortuous path.

Cinching assembly 540 may also utilize a single or any number of tabs or levers to aid in capturing suture 94 and/or creating a tortuous path for suture 94 to traverse. As shown in the cross-sectional view of FIG. 26A, proximal collar 542 may have a pivoting lever 544 formed integrally from a side wall of proximal collar 542. Alternatively, lever 544 may be included in a cinching collar separate from proximal collar 542. Lever 544 may be biased to spring inwardly into proximal collar 542 upon suture 94 passing therethrough. During translation of the anchor in a first direction, suture 94 may be allowed to freely pass through proximal collar 542 and past lever 544 due to its pivoting motion. When the anchor is moved or urged in the reverse direction, lever 544 may act to cinch down upon suture 54 against an inner surface of proximal collar 542, as shown in the figure.

Another variation 546 of assembly 540 is shown in the cross-sectional view of FIG. 26B in which proximal collar 548 is shown as having at least two levers 550, 552 both biased in opposing directions to create a tortuous path for suture 94 to traverse. In either variation, the cinching levers may be configured to prevent or inhibit the over-cinching or cutting of suture 94. FIGS. 26C and 26D show alternative end views of FIG. 26A. Uni-directional lever 544, as seen in FIG. 26C, may be formed from the side wall of proximal collar 542 such that when lever 544 cinches down upon suture 94, the corners or ends of lever 544 contact an inner surface of proximal collar 542 at contact points 554. The contact which occurs may ensure that an open space 556 is preserved and that lever 544 is prevented from over cinching onto suture 94 within space 556 and cutting suture 94. FIG. 26D shows an alternative uni-directional lever 544' which defines a curved or arcuate edge 558 which contacts suture 94. The arcuate edge 558 may prevent the over cinching onto suture 94 and cutting of suture 94.

FIGS. 26E, 26F, and 26G show alternative variations of cinching assembly 546 with uni-directional levers having various configurations. FIG. 26E shows a cross-sectional side view of cinching assembly 560 in which proximal collar 562 may have levers 564, 566 directed and biased in opposing directions to create a tortuous path. Each of the levers 564, 566 in this variation may be curved inwardly towards proximal collar 562. FIG. 26F shows a cross-sectional side view of cinching assembly 568 in which proximal collar 570 has uni-directional levers 572, 574 angled towards on another when biased inwardly. And FIG. 26G shows a cross-sectional side view of cinching assembly 576 in which proximal collar 578 has uni-directional levers 580, 582 curved outwardly relative to one another when the levers are biased within collar 578.

FIGS. 27A and 27B shows yet another variation of cinching assembly 590 which utilizes a reconfigurable hollow member for cinching suture 94. As shown in FIG. 27A, hollow member 594 may be constrained within tubular delivery member 592 to retain an elongate shape with suture 94 passing uninhibited therethrough. When the anchor is to be cinched, hollow member 594 may be advanced distally from tubular member 592 and when hollow member 594 has been ejected, it may adapted to reconfigure itself into a crimped configuration 594' having a non-linear passageway. Suture 94 passing through the crimped configuration 594' may be inhibited from passing freely therethrough by crimp 596 created within the hollow member. Hollow member 594 may have a variety of cross-sectional shapes, e.g., circular, rectangular, square, hexagonal, etc., and it is preferably made from a material having shape memory characteristics, e.g., Nitinol, such that when hollow member 594 is unconstrained, it may automatically reconfigure into its crimped configuration 594'.

Another variation of cinching assembly 600 which is configured to reconfigure itself upon being unconstrained is shown in the cross-sectional views of FIGS. 28A to 28C. In this variation shown in FIG. 28A, cinching collar 602 may comprise at least two circular members, first collar 606 and second collar 608, connected by an elongate bridging member 604. Cinching collar 602 may be positioned within launch tube 18 proximally adjacent to proximal collar 610 and adapted to reconfigure itself once released from launch tube 18 such that a tortuous path is created for suture 94. FIG. 28B shows an alternative variation in the cinching collar which may be an integrated variation with the proximal collar such that first collar 606 is connected directly to the anchor via joining member 612. In either variation, once the cinching collar has been ejected from launch tube 18, the collar may configure itself such that first collar 606 and second collar 608 are biased towards one another to form, e.g., a "C"-shape as shown in FIG. 28C. The tortuous path which is created by cinching collar 602 for suture 94 to follow may be sufficient to prevent the further translation of the anchor relative to suture 94. FIGS. 28D and 28E, respectively, show perspective views of cinching collar 602 in a constrained delivery configuration and an unconstrained cinching configuration.

FIG. 28F shows a cross-sectional side view of another cinching assembly which is similar to the variation shown in FIG. 28B. Rather than having first collar 606 and joining member 612 reconfigure itself into a semi-circular shape relative to the anchor, first collar 606 may reconfigure itself to maintain its orientation relative to the anchor while joining member 612 may be formed to curve appropriately or approximately in an "S"-type configuration. The reconfigured cinching member may act to lock suture 94 relative to the anchor when the anchor is moved in a reverse direction.

Another configuration for a cinching assembly is shown in the side view of FIG. 28G, which shows cinching member 616 located proximally of proximal collar 614. Cinching member 616 may be fabricated from a variety of materials, e.g., Nitinol, spring stainless steel, etc., which exhibit shape memory or superelastic characteristics, or aspects thereof. In use, cinching member 616 may be configured into an elongate delivery configuration. When the tissue anchor is to be cinched or locked relative to the tissue, cinching member 616 may be released from a constraining force such that cinching member 616 reconfigures itself into an expanded or extended configuration which creates a tortuous path for suture 94 which sufficiently locks suture 94 within cinching member 616.

Cinching member 616 may be comprised generally of an elongate bar, ribbon, cylinder, etc., or any elongate member having a diameter or cross-sectional area in its delivery configuration which is sufficiently small to be disposed and/or translated within launch tube 18. Cinching member 616 may define a plurality of openings 618 along the length of cinching member 616 such that when cinching member 616 is in its elongate delivery configuration, as shown in FIG. 28G, suture 94 may be interwoven through openings 618 along a relatively straightened path. Openings 618 may be located along cinching member 616 at uniform locations or they may be randomly positioned along the length of cinching member 616. When released, cinching member 616 may reconfigure itself into an expanded suture-locking configuration 616' which is sufficiently large to prohibit its passage into or through proximal collar 614, as shown in FIG. 28H. Expanded configuration 616' may comprise any reconfigured shape so long as the expanded shape is adapted to create the tortuous path for suture 94 and is large enough so that passage through proximal collar 614 is not possible.

Other cinching and locking mechanisms which utilize mechanical clamping or crimping to achieve locking of the suture within or through the anchors may also be used to facilitate uni-directional locking.

For instance, cinching assembly 620 may be seen in the cross-sectional view of FIGS. 29A and 29B. FIG. 29A shows delivery tube member 622 having crimping collar 624 disposed therewithin proximally of anchor proximal collar 626. Suture 94 may be passed through both crimping collar 624 and proximal collar 626. Once the anchor has been desirably positioned, crimping collar 624 may be advanced distally adjacent to proximal collar 624 and mechanically crimped 624' down upon suture 94 to create a lock and prevent the reverse movement of the anchor over suture 94, as shown in FIG. 29B. The crimping may be accomplished via mechanical graspers or pinchers configured to clamp down upon collar 624. Similarly, FIG. 30A shows cinching assembly 630 in which the crimping collar 632 may be integral with the anchor rather than being a separate member. FIG. 30B shows a mechanically crimped collar 632' which eliminates the need for a separate collar.

To accomplish mechanical crimping upon a cinching collar, various methods may be utilized. FIG. 31A shows one variation of a tool assembly 640 which may be adapted to apply a mechanical crimping force upon a crimping collar. As seen, launch tube 18 may have delivery push tube 642 located therewithin and positioned proximally of proximal collar 652 of the tissue anchor. Push tube 642 may be used to hold and/or eject proximal collar 652 from launch tube 18. Crimping device 644 may be advanced within launch tube 18 via crimping control member 646, which may be manipulated from its proximal end.

A collar retaining channel 650 may be defined in a distal end of crimping device 644 and adapted to receive and securely hold proximal collar 652 within during a clamping or crimping process. Crimping members or arms 648 may be positioned within crimping device 644 on either side of retaining channel 650. When proximal collar 652 or crimping sleeve is to be clamped or crimped, crimping members or arms 648 may be driven into contact with proximal collar 652 to crimp the collar. Moreover, crimping arms 648 may be actuated through a variety of methods, e.g., hydraulically, pneumatically, via mechanical leverage, etc.

An alternative crimping assembly 660 is shown in the cross-sectional view of FIG. 32A. Crimping device 662 may be seen within launch tube 18 extending from crimping control member 664. Collar retaining channel 672 may be likewise defined within crimping device 662 for retaining proximal collar 670 during a crimping procedure. This variation may utilize a separate elongate crimping member 666 having actuatable crimping arms 668 positioned at a distal end of elongate member 666. In use, with proximal anchor collar 670 positioned within retaining channel 672, elongate member 666 may be advanced distally until crimping arms 668 are positioned over proximal collar 670 and crimped down. FIG. 32B shows an exploded perspective view of the crimping assembly.

FIGS. 31B to 31D show side, end, and perspective views, respectively, of one variation of an anchor proximal collar 652 which is adapted for crimping upon a suture passing therethrough. To facilitate crimping of the collar 652, a circumferential slot 656 may be defined through collar 652 partially around its circumference. Another longitudinal slot 658 may be defined through collar 652 extending longitudinally from a proximal edge of collar 652 to circumferential slot 656. These slots 656, 658 may define at least two crimping arms 654 which may be crimped down upon a length of suture passing through collar 652.

Aside from the crimping mechanisms described above, additional measures may be optionally implemented to facilitate the cinching or locking of an anchor. Other measures may also be taken to inhibit any damage from occurring to the suture routed through an anchor.

To ensure that the integrity of suture 94 is maintained in the presence of metallic basket anchors 682 and to ensure that suture 94 is not subjected to any nicks or cuts, the portion of suture 94 passing through basket anchor 682 may be encased in a protective sleeve 690, as shown in the perspective view of FIG. 33A of anchor-sleeve assembly 680. The basket anchor 682 is shown in this variation as having anchor struts or arms 688 in a partially deployed configuration. Sleeve 690 may extend between distal collar 684 and proximal collar 686 to prevent excessive contact between suture 94 and elements of basket anchor 682. FIG. 33B shows an end view of the anchor-sleeve assembly 680 showing the relative positioning of sleeve 690 relative to suture 94 and anchor collar 686. Sleeve 690 may be made from a variety of polymeric materials, e.g., polypropylene, PTFE, etc., provided that the material is suitably soft.

FIG. 34A shows a cross-sectional view of cinching assembly 700 which may be implemented with any of the cinching and locking mechanisms described above. This particular variation utilizes the partial cold-flowing of the engaged suture 94 to enhance the locking or cinching effect of the tissue anchor. The cinching collar, or in this variation proximal collar 702, against which suture 94 is wedged may have multiple through-holes 704 defined over the surface of collar 702. The cross-sectional side view shows suture 94 wedged within collar 702 against locking pin 338. The portion of suture 94 which is adjacent to through-holes 704 may have regions which cold-flow partially into through-holes 704, as shown by cold-flowed suture material 706. These portions of suture material 706 may enhance the locking aspects of suture 94 against collar 702. FIG. 34B shows a perspective view of collar 702 with multiple through-holes 704 defined over the body of collar 702. Through-holes 704 may be defined in a uniform pattern; alternatively, they may be randomly defined over collar 702 or only over portions of collar 702.

FIGS. 35A to 35E show an alternative variation 710 for locking a tissue anchor relative to suture 94. An outer sleeve 720 which is preferably comprised of a polymeric material capable of at least partially flowing when heated, e.g., PTFE, may be disposed circumferentially about an electrically conductive inner sleeve 722. As shown in the perspective views of FIGS. 35B and 35C, inner sleeve 722 may be disposed within lumen 726 of outer sleeve 720. Inner sleeve 722 may randomly or uniformly define a plurality of openings or through-holes 724 over the surface of inner sleeve 722.

In operation, outer and inner sleeves 720, 722, respectively, may be positioned within delivery push tube 716 proximally of proximal collar 718 with suture 94 passing therethrough. When the tissue anchor has been desirably positioned and suture 94 has also been desirably tensioned, an induction unit 712 having one or more induction coils 714 therewithin may be positioned circumferentially (or at least partially circumferentially) about outer and inner sleeves 720, 722. Induction unit 712 may be configured to be disposed within the launch tube 18 or it may be configured to be advanced over or positioned upon launch tube 18. Thermal energy or electrical energy in various forms, e.g., RF, microwave, etc., may be delivered to induction coils 714 such that the energy heats inner sleeve 722, which may be positioned within induction coils 714, as shown in FIG. 35A. As inner sleeve 722 is heated via induction, the inner surface of outer sleeve 720 may be partially melted or deformed such that the material flows at least partially through or within through-hole 724 and contacts suture 94 positioned within inner sleeve 722. The flowed material may cool and act to lock outer and inner sleeves 720, 722 onto suture 94. Induction unit 712 may then be removed from the area leaving outer and inner sleeves 720, 722 locked relative to the tissue anchor.

Although inner sleeve 722 shows through-holes 724 as circularly defined openings, other shapes may be utilized. For example, FIG. 35D shows a perspective view of one inner sleeve variation 728 having longitudinally defined slots 730. Alternatively, FIG. 35E shows a perspective view of another inner sleeve variation 732 having circumferentially defined slots 734. Any variety of opening shapes may be utilized so long as the opening or openings allow for material from the outer sleeve 720 to flow through into contact with the suture positioned within.

Although a number of illustrative variations are described above, it will be apparent to those skilled in the art that various changes and modifications may be made thereto without departing from the scope of the invention. Moreover, although specific locking or cinching configurations may be shown with various types of anchors, it is intended that the various locking or cinching configurations be utilized with the various types of anchors in various combinations as practicable. It is intended in the appended claims to cover all such changes and modifications that fall within the true spirit and scope of the invention.

What is claimed is:

1. An anchor assembly for implantation in a body, comprising:
   an anchor body adapted to be delivered through a hollow member for placement against a tissue surface;
   a locking mechanism comprising a substantially cylindrical body having a proximal end and a distal end and defining a lumen for passage of a flexible member therethrough, and
   a flexible member extending through at least a portion of said anchor body and through the lumen of said locking mechanism;
   wherein substantially all of the locking mechanism is positioned proximally of and is separate from the anchor body and is slidably disposed on the flexible member, and wherein the locking mechanism has at least two arms biased to project in substantially opposing directions into the lumen for contact against the flexible member, with a first of the two arms being nearer to the proximal end of the cylindrical body and the second of the two arms being nearer to the distal end of the cylindrical body, such that the flexible member is uni-directionally advancable through the lumen relative to the anchor body.

2. The anchor of claim 1 wherein the anchor body comprises a T-anchor.

3. The anchor of claim 2 wherein the T-anchor has a cross-sectional shape selected from the group consisting of circles, rectangles, and squares.

4. The anchor of claim 1 wherein the anchor body comprises a basket anchor.

5. The anchor of claim 4 wherein the basket anchor is reconfigurable from a delivery configuration within the hollow member to an expanded configuration outside the hollow member.

6. The anchor of claim 1 wherein the hollow member is selected from the group consisting of tubular members, catheters, needles, and trocars.

7. The anchor of claim 1 wherein the flexible member comprises a length of suture.

8. The anchor of claim 7 wherein the length of suture comprises a monofilament, multifilament, elastic, or elastomeric material.

9. The anchor of claim 7 wherein the length of suture comprises a metallic material.

10. The anchor of claim 9 wherein the metallic material is selected from the group consisting of Nitinol, stainless steel, and Titanium.

11. The anchor of claim 1 wherein the at least two arms are each adapted to pivot about a base into an open position when the anchor body is advanced distally relative to the flexible member.

12. The anchor of claim 1 wherein the at least two arms are each adapted to pivot about a base into a closed position when the anchor body is advanced proximally relative to the flexible member.

13. The anchor of claim 1 wherein the locking mechanism is adapted to automatically impart the locking force upon the flexible member.

14. The anchor of claim 1 wherein the biased arms are adapted to cinch the flexible member against a surface of the lumen.

15. The anchor of claim 1 wherein the biased arms project at an angle proximally of the anchor body.

16. The anchor of claim 1 further comprising a plurality of additional arms each biased to project into the lumen.

17. The anchor of claim 16 wherein the plurality of additional arms are positioned in apposition to one another.

18. The anchor of claim 1 wherein the biased arms are adapted to project partially into the lumen.

19. An anchor assembly for implantation in a body, comprising:
an anchor body adapted to be delivered through a hollow member for placement against a tissue surface;
a locking mechanism comprising a substantially cylindrical body having a proximal end and a distal end, substantially all of which is positioned proximally of and which is separate from the anchor body, the substantially cylindrical body having at least two arms biased to project in substantially opposing directions at an angle relative to the anchor body, with a first of the two arms being nearer to the proximal end of the cylindrical body and the second of the two arms being nearer to the distal end of the cylindrical body, the locking mechanism defining a lumen therethrough, and
a flexible member extending through at least a portion of said anchor body and through the lumen of said locking mechanism;
wherein the arms define an opening for passage of the flexible member therethrough such that the flexible member is uni-directionally advancable through the opening relative to the anchor body.

20. The anchor of claim 19 wherein the anchor body comprises a T-anchor.

21. The anchor of claim 20 wherein the T-anchor has a cross-sectional shape selected from the group consisting of circles, rectangles, and squares.

22. The anchor of claim 19 wherein the anchor body comprises a basket anchor.

23. The anchor of claim 22 wherein the basket anchor is reconfigurable from a delivery configuration within the hollow member to an expanded configuration outside the hollow member.

24. The anchor of claim 19 wherein the hollow member is selected from the group consisting of tubular members, catheters, needles, and trocars.

25. The anchor of claim 19 wherein the flexible member comprises a length of suture.

26. The anchor of claim 25 wherein the length of suture comprises a monofilament, multifilament, elastic, or elastomeric material.

27. The anchor of claim 25 wherein the length of suture comprises a metallic material.

28. The anchor of claim 27 wherein the metallic material is selected from the group consisting of Nitinol, stainless steel, and Titanium.

29. The anchor of claim 19 wherein the at least two arms are each adapted to pivot about a base into an open position when the anchor body is advanced distally relative to the flexible member.

30. The anchor of claim 19 wherein the at least two arms are each adapted to pivot about a base into a closed position when the anchor body is advanced proximally relative to the flexible member.

31. The anchor of claim 19 wherein the locking mechanism is adapted to automatically impart the locking force upon the flexible member.

32. The anchor of claim 19 wherein the biased arms each project at an angle proximally of the anchor body.

33. The anchor of claim 19 wherein the opening is tapered.

* * * * *